(12) United States Patent
Baumhof et al.

(10) Patent No.: US 8,968,746 B2
(45) Date of Patent: Mar. 3, 2015

(54) COMPLEXATION OF NUCLEIC ACIDS WITH DISULFIDE-CROSSLINKED CATIONIC COMPONENTS FOR TRANSFECTION AND IMMUNOSTIMULATION

(75) Inventors: Patrick Baumhof, Dusslingen (DE); Söhnke Voss, Dossenheim (DE); Thomas Kramps, Tübingen (DE); Karl-Josef Kallen, Bad Homburg (DE)

(73) Assignee: CureVac GmbH, Tübingen (DE)

( * ) Notice: Subject to any disclaimer, the term of this patent is extended or adjusted under 35 U.S.C. 154(b) by 0 days.

(21) Appl. No.: 13/203,653

(22) PCT Filed: Jul. 25, 2011

(86) PCT No.: PCT/EP2011/003719
§ 371 (c)(1),
(2), (4) Date: Feb. 14, 2013

(87) PCT Pub. No.: WO2012/013326
PCT Pub. Date: Feb. 2, 2012

(65) Prior Publication Data
US 2013/0142818 A1    Jun. 6, 2013

Related U.S. Application Data

(60) Provisional application No. 61/369,549, filed on Jul. 30, 2010.

(51) Int. Cl.
| | | |
|---|---|---|
| A61K 39/385 | (2006.01) | |
| A61K 45/00 | (2006.01) | |
| A61K 47/00 | (2006.01) | |
| A61K 48/00 | (2006.01) | |
| A61K 39/39 | (2006.01) | |
| C12N 15/87 | (2006.01) | |
| A61K 39/00 | (2006.01) | |

(52) U.S. Cl.
CPC ............. *A61K 48/0041* (2013.01); *A61K 39/39* (2013.01); *C12N 15/87* (2013.01); *A61K 39/00* (2013.01); *A61K 2039/55516* (2013.01); *A61K 2039/55561* (2013.01)
USPC .................................... 424/193.1; 424/278.1

(58) Field of Classification Search
CPC ... A61K 48/0041; A61K 39/39; A61K 39/00; A61K 2039/55516; A61K 2039/55561; C12N 15/87
See application file for complete search history.

(56) References Cited

U.S. PATENT DOCUMENTS

| | | |
|---|---|---|
| 3,906,092 A | 9/1975 | Hilleman et al. |
| 4,373,071 A | 2/1983 | Itakura |
| 4,401,796 A | 8/1983 | Itakura |
| 4,415,732 A | 11/1983 | Caruthers et al. |
| 4,578,399 A | 3/1986 | Schorlemmer et al. |
| 5,516,652 A | 5/1996 | Abramovitz et al. |
| 5,663,153 A | 9/1997 | Hutcherson et al. |
| 5,663,163 A | 9/1997 | Takaya et al. |
| 5,844,075 A | 12/1998 | Kawakami et al. |
| 5,965,720 A | 10/1999 | Gryaznov et al. |
| 6,096,307 A | 8/2000 | Braswell et al. |
| 6,218,371 B1 | 4/2001 | Krieg et al. |
| 6,239,116 B1 | 5/2001 | Krieg et al. |
| 6,322,967 B1 | 11/2001 | Parkin |
| 6,406,705 B1 | 6/2002 | Davis et al. |
| 6,498,148 B1 | 12/2002 | Raz |
| 6,514,948 B1 | 2/2003 | Raz et al. |
| 6,552,006 B2 | 4/2003 | Raz et al. |

(Continued)

FOREIGN PATENT DOCUMENTS

| | | |
|---|---|---|
| AU | 776268 | 12/2000 |
| DE | 102004035227 | 2/2002 |

(Continued)

OTHER PUBLICATIONS

Eliyahu et al "Polymers for DNA Delivery" Molecules 10:34-64. Published Jan. 31, 2005.*
Xiong et al., "pH-responsive multi-PEGylated dual cationic nanoparticles enable charge modulations for safe gene delivery," *Chem Med Chem*, 2:1321-1327, 2007.
Adams Ad et al., Preparation and hybridization properties of oligonucleotides containing 1-alpha-D-arabinofuranosylthymine, Nucleic Acids Res. Jul. 11, 1991; 19(13):3647-51.
Agrawal, 1996; Antisense oligonucleotides: towards clinical trails; Trends in Biotechnology; vol. 14; No. 10; pp. 376-387.
Ara et al., 2001; Zymosan enhances the immune response to DNA vaccine for human immunodeficiency virus type-1 through the activation of complement system; Immunology; vol. 103, pp. 98-105.
Bayard et al.; 1985; Antiviral activity in L1210 cells of liposome-encapsulated (2'-5')oligo(adenylate)analogues; Eur. J. Biochem., vol. 151, No. 2, pp. 319-326.

(Continued)

*Primary Examiner* — Maury Audet
*Assistant Examiner* — Zachary J Miknis
(74) *Attorney, Agent, or Firm* — Parker Highlander PLLC

(57) ABSTRACT

The present invention is directed to a polymeric carrier cargo complex, comprising as a cargo at least one nucleic acid (molecule) and disulfide-crosslinked cationic components as a (preferably non-toxic and non-immunogenic) polymeric carrier. The inventive polymeric carrier cargo complex allows for both efficient transfection of nucleic acids into cells in vivo and in vitro and/or for induction of an (innate and/or adaptive) immune response, preferably dependent on the nucleic acid to be transported as a cargo. The present invention also provides, pharmaceutical compositions, particularly vaccines and adjuvants, comprising the inventive polymeric carrier cargo complex and optionally an antigen, as well as the use of such the inventive polymeric carrier cargo complex and optionally an antigen for transfecting a cell, a tissue or an organism, for (gene-)therapeutic purposes as disclosed herein, and/or as an immunostimulating agent or adjuvant, e.g. for eliciting an immune response for the treatment or prophylaxis of diseases as mentioned above. Finally, the invention relates to kits containing the inventive polymeric carrier cargo complex and/or the inventive pharmaceutical composition, adjuvant or vaccine in one or more parts of the kit.

16 Claims, 15 Drawing Sheets

(56) References Cited

U.S. PATENT DOCUMENTS

Figure 1:
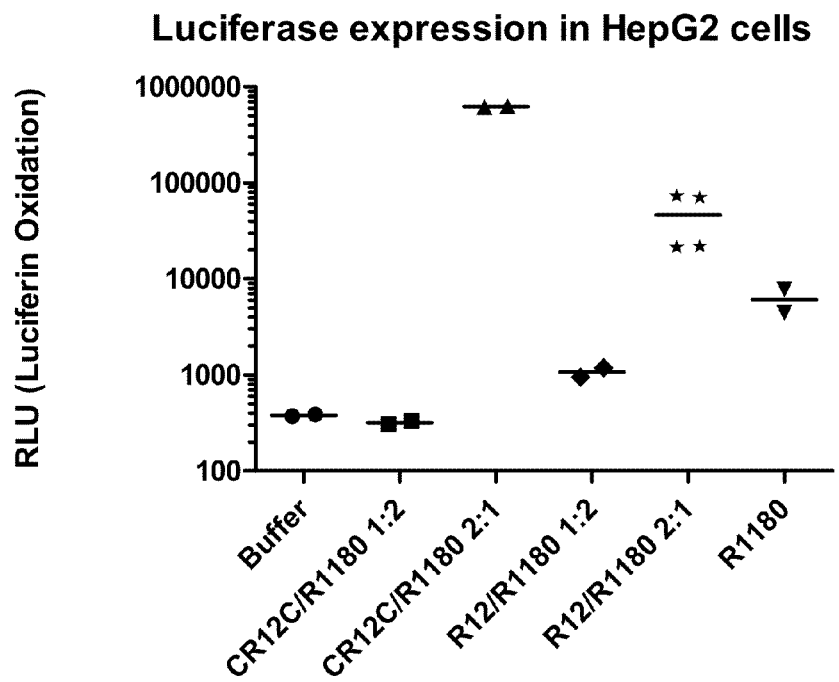

| | | |
|---|---|---|
| 6,589,940 B1 | 7/2003 | Raz et al. |
| 6,610,661 B1 | 8/2003 | Carson et al. |
| 6,689,757 B1 | 2/2004 | Craig |
| 6,716,434 B1 | 4/2004 | Ansley et al. |
| 7,001,890 B1 | 2/2006 | Wagner et al. |
| 7,208,478 B2 | 4/2007 | Carson et al. |
| 7,407,944 B2 | 8/2008 | Agrawal et al. |
| 7,470,674 B2 | 12/2008 | Agrawal et al. |
| 7,517,862 B2 | 4/2009 | Agrawal et al. |
| 2003/0225016 A1 | 12/2003 | Fearon et al. |
| 2004/0006010 A1 | 1/2004 | Carson et al. |
| 2004/0006034 A1 | 1/2004 | Raz et al. |
| 2004/0047869 A1 | 3/2004 | Garcon et al. |
| 2004/0052763 A1 | 3/2004 | Mond et al. |
| 2005/0032730 A1 | 2/2005 | Von Der Mulbe et al. |
| 2005/0037494 A1 | 2/2005 | Hecker et al. |
| 2005/0059624 A1 | 3/2005 | Hoerr et al. |
| 2005/0130918 A1 | 6/2005 | Agrawal et al. |
| 2005/0250723 A1 | 11/2005 | Hoerr et al. |
| 2006/0172966 A1 | 8/2006 | Lipford et al. |
| 2006/0188490 A1 | 8/2006 | Hoerr et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1* | 8/2010 | Fotin-Mleczek et al. .. 424/193.1 |
| 2010/0291156 A1 | 11/2010 | Barner et al. |
| 2010/0305196 A1 | 12/2010 | Probst et al. |
| 2011/0053829 A1* | 3/2011 | Baumhof et al. ............. 514/1.2 |
| 2011/0250225 A1 | 10/2011 | Fotin-Mleczek et al. |
| 2011/0311472 A1 | 12/2011 | Hoerr et al. |
| 2012/0021043 A1 | 1/2012 | Kramps et al. |
| 2012/0258046 A1 | 10/2012 | Mutzke |

FOREIGN PATENT DOCUMENTS

| | | |
|---|---|---|
| DE | 10148886 | 4/2003 |
| DE | 69819150 | 7/2004 |
| DE | 102006007433 | 8/2007 |
| EP | 0347501 | 12/1989 |
| EP | 0772619 | 5/1997 |
| EP | 0839912 | 5/1998 |
| EP | 1063232 | 3/2001 |
| EP | 1167379 | 1/2002 |
| EP | 1374894 | 1/2004 |
| EP | 1393745 | 3/2004 |
| EP | 1564291 | 8/2005 |
| EP | 1905844 | 4/2008 |
| JP | 2008-542500 | 11/2008 |
| KR | 10-1003622 | 9/2003 |
| KR | 10-1051785 | 1/2005 |
| KR | 10-1032853 | 4/2005 |
| WO | WO91/05560 | 5/1991 |
| WO | WO94/17093 | 8/1994 |
| WO | WO94/17792 | 8/1994 |
| WO | WO 98/19710 | 5/1998 |
| WO | WO 98/47913 | 10/1998 |
| WO | WO99/53961 | 10/1999 |
| WO | WO00/75304 | 12/2000 |
| WO | WO01/04135 | 1/2001 |
| WO | WO01/75164 | 10/2001 |
| WO | WO01/93902 | 12/2001 |
| WO | WO01/97843 | 12/2001 |
| WO | WO02/00594 | 1/2002 |
| WO | WO02/00694 | 1/2002 |
| WO | WO02/078614 | 10/2002 |
| WO | WO02/098443 | 12/2002 |
| WO | WO03/028656 | 4/2003 |
| WO | WO03/057822 | 7/2003 |
| WO | WO 03/059381 | 7/2003 |
| WO | WO03/066649 | 8/2003 |
| WO | WO 03/068942 | 8/2003 |
| WO | WO03/066280 | 10/2003 |
| WO | WO2004/004743 | 1/2004 |
| WO | WO2004/058159 | 7/2004 |
| WO | WO2004/064782 | 8/2004 |
| WO | WO2004/092329 | 10/2004 |
| WO | WO2005/001022 | 1/2005 |
| WO | WO2005/030259 | 4/2005 |
| WO | WO 2005-062947 | 7/2005 |
| WO | WO2005/097993 | 10/2005 |
| WO | WO2006/029223 | 3/2006 |
| WO | WO 2006/046978 | 5/2006 |
| WO | WO2006/116458 | 11/2006 |
| WO | WO 2007-008300 | 1/2007 |
| WO | WO 2007/031319 | 3/2007 |
| WO | WO2007/031322 | 3/2007 |
| WO | WO2007/042554 | 4/2007 |
| WO | WO2007/051303 | 5/2007 |
| WO | WO 2007/069068 | 6/2007 |
| WO | WO2007/124755 | 11/2007 |
| WO | WO2008/014979 | 2/2008 |
| WO | WO 2009/030254 | 3/2009 |
| WO | WO2009/030481 | 3/2009 |
| WO | WO 2009030481 A1 * | 3/2009 |
| WO | WO2009/053700 | 4/2009 |
| WO | WO2009/086640 | 7/2009 |
| WO | WO2010/037408 | 4/2010 |
| WO | WO 2010/037539 | 4/2010 |
| WO | WO 2011/026641 | 3/2011 |
| WO | WO 2013/113501 | 8/2013 |

OTHER PUBLICATIONS

Bettinger T. et al., Peptide-mediated RNA delivery: a novel approach for enhanced transfection of primary and Post-mitotic cells, Nucleic Acids Research, 2001, vol. 29, No. 18, 3882-3891.

Blaxter et al., 2002; The *Brugia malayi* genome project: expressed sequence tags and gene discovery; Transactions of the Royal Society of Tropical Medicine and Hygiene, vol. 96, No. 1, pp. 1-17.

Bocchia et al., 2000; Antitumor vaccination: where we stand: Heamatologica, vol. 85, No. 11, pp. 1172-1206.

Buteau et al., 2002; Challenges in the Development of Effective Peptide Vaccines for Cancer; Mayo Clin Proc, vol. 77. pp. 339/349.

Diebold et al., 2004; Innate Antiviral Responses by Means of TLR7-Mediated Recognition of Single-Stranded RNA; Science; vol. 303; pp. 1529-1531.

EBI Database accession No. CZ193289; PST12107-M1CB1 *Mus musculus* genomic clone PST12107-NR; Database EMBL; 2005.

EBI Database accession No. DN868844; NEIBank analysis of a Dog lens; Wistow, F. Database EMBL; 2005.

EMBL accession No. AA430815; *Brugia malayi* strain TRS Labs clone RRAMCA1537 EST; Database EMBL; 2000.

Feroze-Merzoug et al., 2001; Molecular profiling in prostate cancer, Cancer and Metastasis Reviews, vol. 20, pp. 165-171.

Fre et al., 1998; Potent and specific genetic interference by double-stranded RNA in *Caenorhabditis elegans*; Nature; vol. 391; pp. 806-811.

Fotin-Mleczek, Mariola et al: Messenger RNA-based vaccines with dual activity induce balanced TLR-7 dependent adaptive immune responses and provide antitumor activity, Journal of Immunotheraphy, Raven Press, NY, US, vol. 34, No. 1, Jan. 1, 2011, pp. 1-15.

Galbraith et al., 1994; Complement Activation and Hemodynamic Changes Following Intravenous Administration of Phosphorothioate Oligonucleotides in the Monkey; Antisense Research and Development: vol. 4, pp. 201-206.

Gao et al., 2007; Nonviral gene delivery: what we know and what is next; The AAPS Journal, vol. 9, No. 1, pp. E92-104, XP02609380.

GENBANK Accession No. JK489756.1, GI: , 346421249, pubically available Sep. 2011.

Georgieva et al., Comparative study on the changes in photosynthetic activity of the homoiochlorophyllous desiccation and rehydration, Photosythesis Research, vol. 85, pp. 191-203, Aug. 2005.

Gryaznov, 1999; Oligonucleotide N3'→P5' phosphoramidates as potential therapeutic agents; Biochimica et Biophysica Acta; vol. 1489, pp. 131-140.

(56) References Cited

OTHER PUBLICATIONS

Hardy et al., 2009; Synergistic effects on gene delivery—co-formulation of small disulfide-linked dendritic polycations with Lipofectamine 2000; Organic & Biomolecular Chemistry, vol. 7, No. 4, pp. 789-793, XP1002609381.
Hausch et al.; 1998; A novel carboxy-functionalized photocleavable dinucleotide analog for the selection for RNA catalysts; Tetrahedron Letters, vol. 39, No. 34, pp. 6157-6158.
Heidenreich et al., 1993, Chemically modified RNA: approaches and applications; FASEB Journal; vol. 7 No. 1, pp. 90-96.
Heil et al., 2004; Species-specific recognition of single stranded RNA via Toll-like receptor 7 and 8; Science, vol. 303, pp. 1526-1529.
Herbert et al., The Dictionary of Immunology, Academic Press, $4^{th}$ edition, 1995.
Herbert et al., 2005; Lipid modification of GRN163, an N3'→P5' thio-phosphoramidate oligonucleotide, enhances the potency of telomerase inhibition; Oncogene; vol. 24; pp. 5262-5268.
Heymann, 1990; The immune complex: possible ways of regulating the antibody response; Immunology Today; vol. 11, No. 9, pp. 310-313.
Hoerr et al., 2000; In vivo application of RNA leads to induction of specific cytotoxic T lymphocytes and antibodies; Eur. J. Immunol., vol. 30, No. 1, pp. 1-7.
Janssen et al., 2003; Role of Toll-Like Receptors in Pathogen Recognition; Clinical Microbiology Reviews, vol. 16, No. 4; pp. 637-646.
Kim et al., 2009; VeGF siRNA delivery system using arginine-grafted bioreducible poly(disulfide amine); Molecular Pharmaceutics, vol. 6, No. 3, pp. 718-726, XP002609382.
Kwiatkowski et al., 1984; The 9-(4-Octadecyloxyphenylxanthen)-9-yl-Group. A new Acid-labile Hydroxyl Protection Group and $1^{st}$ Application in the Preparative reserve-phase Chromatographic Separation of Oligonbonucleotides; Acta Chemica Scandinavica; B38(8); pp. 657-871.
Lo et al., 2008, An endosomolytic Tat peptide produced by incorporation of histidine and cysteine residues as a nonviral vector for DNA transfection; Biomaterials, vol. 29, No. 15, pp. 24082414, XP022526913.
Lochmann et al., 2004; Drug delivery of oligonucleotides by peptides; European Journal of Pharmaceutics and Biopharmaceutics; vol. 58, No. 2. pp. 237-251.
Mateo et al., 1999, An HLA-A2 Polyepitope Vaccine for melanoma Immunotherapy; J Immunol, vo. 163. pp. 4058-4063.
Matray et al., 1999; Synthesis and properties of RNA analogs—oligoribonucleotide N3'→P5' phosphoramidates; Nucleic Acids Research; vol. 27, No. 20. pp. 3976-3985.
McKenzie et al., 2000; A potent new class of reductively activated peptide gene delivery agents; Journal of Biological Chemistry, vol. 275, No. 14, pp. 9970-9977, XP002238140.
McKenzie et al., 2000; Low molecular weight disulfide cross-linking peptides as nonviral gene delivery carriers; Bioconjugate Chemistry, vol. 11, No. 6, pp. 901-909, XP002609379.
Milich et al., 1997; The Hepatitis B Virus Core and e Antigens Elicit Different Th Cell Subsets: Antigen Structure Can Affect TH Cell Phenotype; Journal of Virology, vol. 71, No. 3, pp. 2192-2201.
Minks et al., 1979; Structural requirements of Double-stranded RNA for the Activation of 2',5'-Oligo(A) Polymerase and Protein Kinase of Interferon-treated HeLa Cells; The Journal of Biological Chemistry; vol. 254, No. 20, pp. 10180-10183.
Miyata et al., 2004; Block Catiomer Polyplexes with Regulated Densities of Charge and Disulfide Cross-Linking Directed to Enhance Gene Expression; Journal of American Chemical Society, vol. 126, No. 8, pp. 2355-2361, XP002993261.
Nicholson et al., 1986; Accurate in vitro cleavage by Rnase III of phosphothioate-substitued RNA processing signals in bacteriophage T7 early mRNA; Nucleic Acids Res., vol. 16, No. 4, pp. 1577-1591.
Parkinson et al., 2004, A transcriptomic analysis of the phylum Nematoda; Nature Genetics, vol. 36, No. 12, pp. 1259-1267.
Ramazeilles et al., 1994; Antisense phosphoothioate oligonucleotides: Selective Kil;ling of the intracellular parasite *Leishmania amazonensis*; Proc. Natl. Acad. Sci., vol. 91, pp. 7859-7863.
Read et al., 2003; Vectors based on reducible polycations facillate intracellular release of nucleic acids; Journal of Gene Medicine, vol. 5 No. 3, pp. 232-245, XP002481542.
Read et al., 2005; A versatile reducible polycationic-based system for efficient delivery of a broad range of nucleic acids; Nucleic acids research, vol. 33 No. 9. pp. 1-16; XP002447464.
Riedl et al., 2002; Priming Th1 Immunity to Voral Core Particles is Facilitated by Trace Amounts of RNA Bound to $1^{st}$ Arginine-Rich Domain; the Journal of Immunology, vol. 168, pp. 4951-4959.
Romagne F., Current and future drugs targeting one class of innate immunity receptors: the Toll-like recptors. Drug Discov Today. Jan. 2007; 12(1-2):80-7. Epub Nov. 28, 2006.
Saenz-Badillos, 2001: RNA as a tumor vaccine: a review of the literature; Exp. Dermatol.; vol. 10, No. 3, pp. 143-154.
Scheel et al., 2003; mRNA as immunostimulatory molecule; Krebsimmuntherapie—Annual Meeting 2003; Abstract (online publication, http://www.kimt.de/archiv/abstracts/htm) Session 5 Abstract 10.
Scheel et al., 2004; Immunostimulating capacities of stabilized RNA molecules; Eur. J. Immunol., vol. 24, pp. 537-547.
Scheel et al., 2005; Toll-like receptor-dependent activation of several human blood cell types by protamine-condensed mRNA, Eur J Immunol, vol. 35, No. 5, pp. 1557-1566.
Scheel et al., Therapeutic anti-tumor immunity triggered by injections of immunostimulating single stranded RNA; Eur J Immunol, vol. 36, No. 10, pp. 2807-2816, 2006.
Schirrmacher et al., 2000; Intra-pinna anti-tumor vaccination with self-replicating infectious RNA or with DANN encoding a model tumor antigen and a cytokine; Gene Therapy, vol. 7 No. 13, pp. 1137-1147.
Shea et al., 1990, Synthesis, hybridization properties and antiviral activity of lipid-oligodeoxynucleotide conjugates; Nucleic Acids Research; vol. 18, No. 13, pp. 3777-3783.
Stephens et al., Sequence analysis of the major outer membrane protein gene from *Chiamydia trachomatics* serovar L2, Journal of Bacteriology, vol. 168, No. 3, pp. 1277-1282, Dec. 1986.
Takae et al., 2008; PEG-detachable polyplex micelles based on disulfide-linked block catiomers as bioresponsive nonviral gene vectors; Journal of the American Chemical Society, vol. 130, No. 18, pp. 6011-6009, XP 002609383.
Teplova et al., 1999; Crystal structure and improved antisense properties of 2'-O-(2-methoxyethyl)-RNA; Nature Structural Biology; vol. 6, No. 6, pp. 535-539.
Tokunaga et al., 2004; Effect of oligopeptides on gene expression: Comparison of DNA/peptide and DNA/peptide/liposome complexes; International Journal of Pharmaceutics, vol. 269, No. 1, pp. 71-80, XP002609384.
Trinchieri et al., 2007; Cooperation of Toll-like receptor signals in innate immune defense; Nature Reviews Immunology; vol. 7. Mar. 2007; pp. 179-190.
Tse K et al., Update on toll-like receptor directed therapies for human disease, Ann Rheum Dis. Nov. 2007; 66 Suppl 3:iii777-80. Review.
Zhou et al., 1999; RNA Melanoma Vaccine: Induction of Antitumor Immunity by Human Glycoprotein 100 mRNA Immunization; Human Gene Therapy; vol. 10; pp. 2719-2714.
Zimmerman S et al., Immunostimulatory DNA as adjuvant: efficacy of phosphodiester CpG oligonucleotides is enhanced by 3' sequence modifications, Vaccine. Feb. 14, 2003; 211(9-10):990-5. (anly abstract).
Notice of Allowance issued in U.S. Appl. No. 13/378,241, mailed Nov. 22, 2013.
"Cell-penetrating peptide," Wikipedia, located at http://en.wikipedia.org/wiki/cell-penetrating_peptide, downloaded on Dec. 11, 2012.
"DOC/Alum Complex," Violin: Vaccine investigation and online information network, located at http://www.violinet.org/vaxjo/vaxjo_detail.php?c_vaxjo_id=49, downloaded on Aug. 28, 2012.
"QS21," Wikipedia, located at http://en.wikipedia.org/wiki/QS21, downloaded on Dec. 11, 2012.

(56) References Cited

OTHER PUBLICATIONS

"Ribi vaccine adjuvant," Violin: Vaccine investigation and online information network, located at http://www.violinet.org/vaxjo/vaxjo_detail.php?c_vaxjo_id=21, downloaded on Dec. 17, 2012.
"SPT (Antigen Formulation)," Violin: Vaccine investigation and online information network, located at http://www.violinet.org/vaxjo/vaxjo_detail.php?c_vaxjo_id=72, downloaded on Aug. 21, 2012.
"Virus-like particle," Wikipedia, located at http://en.wikipedia.org/wiki/virus-like_particle, downloaded on Sep. 3, 2012.
Berzofsky et al., "Progress on new vaccine strategies against chronic viral infections", *J Clin Invest.*, 114(4):450-62, 2004.
Bolhassani et al., "Improvement of different vaccine delivery systems for cancer therapy", *Molecular Cancer*, 10(1):3, 2011.
Bot et al., "Enhanced protection against influenza virus of mice immunized as newborns with a mixture of plasmids expressing hemagglutinin and nucleoprotein", *Vaccine*, 16(17):1675-1682, 1998.
Bot et al., "Genetic immunization of neonates", *Microbes and Infection*, 4(4):511-520, 2002.
Bot et al., "Induction of humoral and cellular immunity against influenza virus by immunization of newborn mice with a plasmid bearing a hemagglutinin gene", *International Immunology*, 9(11):1641-1650, 1997.
Brito et al., "Non-viral eNOS gene delivery and transfection with stents for the treatment of restenosis", *Biomed Eng Online*, 9:56, 2010.
Burke et al., "Extracellular barriers to in vivo PEI and PEGylated PEI polyplex-mediated gene delivery to the liver", *Bioconjug Chem.*, 19(3):693-704, 2008.
Carralot et al., "Polarization of immunity induced by direct injection of naked sequence-stabilized mRNA vaccines", *CMLS Cellular and Molecular Life Sciences*, 61(18):2418-2424, 2004.
Casciato, "Preface", *Manual of Clinical Oncology*. 6$^{th}$ ed. Philadelphia: Lippincott Williams & Wilkins, 2009. ix. Print.
Cooper et al., "CPG 7909 adjuvant improves hepatitis B virus vaccine seroprotection in antiretroviral-treated HIV-infected adults," *AIDS*, 19:1473-1479, 2005.
Danhier et al., "PLGA-based nanoparticles: an overview of biomedical applications", *J Control Release*, 161(2):505-22, 2012.
Deshayes et al., "Cell-penetrating peptides: tools for intracellular delivery of therapeutics", *Cellular and Molecular Life Sciences*, 62(16):1839-1849, 2005.
Dmitriev, "Bactenecin 7 peptide fragment as a tool for intracellular delivery of a phosphorescent oxygen sensor," *FEBS Journal*, 277:4651-4661, 2010.
Fajac et al., "Histidylated polylysine as a synthetic vector for gene transfer into immortalized cystic fibrosis airway surface and airway gland serous cells", *J Gene Med.*, 2(5):368-378, 2000.
Foerg et al., "On the biomedical promise of cell penetrating peptides: limits versus prospecis", *J Pharm Sci.*, 97(1):144-162, 2008.
Fox, "Squalene emulsions for parenteral vaccine and drug delivery," *Molecules*, 14:3286-3312, 2009.
Fujita et al., "Calcium enhanced delivery of tetraarginine-PEG-lipid-coated DNA/protamine complexes", *International Journal of Pharmaceutics*, 368(1-2):186-192, 2009.
Garinot et al., "PEGylated PLGA-based nanoparticles targeting M cells for oral vaccination", *Journal of Controlled Release*, 120(3):195-204, 2007.
Giel-Pietraszuk et al., "Interaction of HIV Tat model peptides with tRNA and 5S rRNA", *Database Biosis*, Database Accession No. Prev199800116011. (Abstract—1 page), 1997.
Gravekamp et al., "Cancer vaccines in old age", *Experimental Gerontology*, 42(5):441-450, 2007.
Hamidi et al., "Pharmacokinetic consequences of pegylation", *Drug Deliv.*, 13(6):399-409, 2006.
Huang et al., "Recent development of therapeutics for chronic HCV infection", *Antiviral Res.*, 71:351-362, 2006.
Huget et al., "Adjuvant and suppressor activity of the polycation protamine hydrochloride in the primary immune response of mice", *Z Immunitatsforsch Immunobiol.*, 152(3):190-9, 1976. (English Abstract).
Kilk, "Cell-penetrating peptides and bioactive cargoes. Strategies and mechanisms," *Department of Neurochemistry and Neurotoxicology Arrhenius Laboratories of Natural Sciences*, Stockholm University, 2004.
Kovarik et al., "Optimization of vaccine responses in early life: the role of delivery systems and immunomodulators", *Immunology and Cell Biology*, 76(3):222-236, 1998.
Koziel et al., "Hepatitis C virus (HCV)-specific cytotoxic T lymphocytes recognize epitopes in the core and envelope proteins of HCV", *J Virol.*, 67(12):7522-32, 1993.
Kwok et al., "Formulation of highly soluble poly(ethylene glycol)-peptide DNA condensates", *J Pharm Sci.*, 88(10):996-1003, 1999.
Martin et al., "Peptide-guided gene delivery", *AAPS J.*, 9(1):E18-E29, 2007.
Mattner et al., "Vaccination with poly-L-arginine as immunostimulant for peptide vaccines: induction of potent and long-lasting T-cell responses against cancer antigens", *Cancer Research*, 62:1477-1480, 2002.
Nakamura et al., "Octaarginine-modified multifunctional envelope-type nano device for siRNA", *Journal of Controlled Release*, 119(3):360-367, 2007.
Neu et al., "Recent advances in rational gene transfer vector design based on poly(ethylene imine) and its derivatives", *J Gene Med.*, 7(8):992-1009, 2005.
Oupicky et al., "Importance of lateral and steric stabilization of polyelectrolyte gene delivery vectors for extended systemic circulation", *Mol Ther.*, 5(4):463-472, 2002.
Oupicky et al., "Laterally stabilized complexes of DNA with linear reducible polycations: strategy for triggered intracellular activation of DNA delivery vectors", *J Am Chem Soc.*, 124(1):8-9, 2002.
Parker et al., "Enhanced gene transfer activity of peptide-targeted gene-delivery vectors", *J Drug Target.*, 13(1):39-51, 2005.
Pichon et al., "Poly[Lys-(AEDTP)] a cationic polymer that allows dissociation of pDNA/cationic polymer complexes in a reductive medium and enhances polyfection", *Bioconjug Chem.*, 13(1):76-82, 2002.
Pomroy et al., "Solubilization of hydrophobic peptides by reversible cysteine PEGylation", *Biochem Biophys Res Commun.*, 245(2):618-21, 1998.
Racanelli et al., "Presentation of HCV antigens to naïve CD8+T cells: why the where, when, what and how are important for virus control and infection outcome", *Clin Immunol.*, 124(1):5-12, 2007.
Radu et al., "Plasmid expressing the influenza HA gene protects old mice from lethal challenge with influenza virus", *Viral Immunology*, 12(3):217-226, 1999.
Read et al., "RNA-based therapeutic strategies for cancer", *Expert Opinion on Therapeutic Patents*, 13(5):627-638, 2003.
Rittner et al., "New basic membrane-destabilizing peptides for plasmid-based gene delivery in vitro and in vivo," *Molecular Therapy*, 5(2):104-114, 2002.
Rollier et al., "Control of heterologous hepatitis C virus infection in chimpanzees is associated with the quality of vaccine-induced peripheral t-helper immune response", *J Virol.*, 78(1):187-196, 2004.
Sakae et al., "Highly efficient in vivo gene transfection by plasmid/PEI complexes coated by anionic PEG derivatives bearing carboxyl groups and RGD peptide", *Biomedicine and Pharmacotherapy*, 62(7):448-453, 2008.
Shiffman et al., "Protein dissociation from DNA in model systems and chromatin", Nucleic Acids Res., 5(9):3409-26, 1978.
Shirai et al., "An epitope in hepatitis C virus core region recognized by cytotoxic T cells in mice and humans", *J Virol.*, 68(5):3334-3342, 1994.
Sun et al., "Advances in saponin-based adjuvants," *Vaccine*, 27:1787-1796, 2009.
Tan et al., "Strategies for hepatitis C therapeutic intervention: now and next", *Curr Opin in Pharmacology*, 4:465-470, 2004.
Tan et al., "Strategies for hepatitis C therapeutic intervention: now and next," *Curr Opin Pharmacol.*, 4(5):465-470, 2004.

(56) References Cited

OTHER PUBLICATIONS

Tönges et al., "Stearylated octaarginine and artificial virus-like particles for transfection of siRNA into primary rat neurons", *Cold Spring Harbor Laboratory Press RNA*, 12(7):1431-1438, 2006.
Unnamalai et al., "Cationic oligopeptide-mediated delivery of dsRNA for post-transcriptional gene silencing in plant cells", *FEBS Letters*, 566(1-3):307-310, 2004.
Vivès et al., "A truncated HIV-1 Tat protein basic domain rapidly translocates through the plasma membrane and accumulates in the cell nucleus", *J Biol Chem.*, 272(25):16010-16017, 1997.
Wang et al., "An intracellular delivery method for siRNA by an arginine-rich peptide", *Journal of Biochemical and Biophysical Methods*, 70(4):579-586, 2007.
Wyman et al., "Design, synthesis, and characterization of a cationic peptide that binds to nucleic acids and permeabilizes bilayers," *Biochemistry*, 36:3008-3017, 1997.
Zhang et al., "Delivery of telomerase reverse transcriptase small interfering RNA in complex with positively charged single-walled carbon nanotubes suppresses tumor growth", *Clin Cancer Res.*, 12(16):4933-4939, 2006.
Zohra et al., "Effective delivery with enhanced translational activity synergistically accelerates mRNA-based transfection", *Biochem Biophys Res Commun.*, 358(1):373-8, 2007.
CAPLUS accession No. 190686-49-8; *Brugia malayi* strain TRS Labs conie RRAMCA1537 EST; *Chemical Abstracts Services*; Database CAPLUS; Jun. 2009.
EBI Database accession No. BP836659; *Arabidopsis thaliana* clone RAFL22-17-C17 EST; Database EMBL; Jan. 2005.

\* cited by examiner

| Cationic component/nucleic acid | Ratio (w/w) | ZP mV |
|---|---|---|
| $CR_{12}C/R722$ | 5:1 | 47,5 |
| $CR_{12}C/R722$ | 4:1 | 19,6 |
| $CR_{12}C/R722$ | 3:1 | 23,8 |
| $CR_{12}C/R722$ | 2:1 | 35 |
| $CR_{12}C/R722$ | 1:1 | -14,5 |
| $CR_{12}C/R722$ | 1:2 | -14 |
| $CR_{12}C/R722$ | 1:3 | -5,16 |
| $CR_{12}C/R722$ | 1:4 | -8,07 |
| $CR_{12}C/R722$ | 1:5 | -12,4 |

A

B

A

B

A

B

A

B

COMPLEXATION OF NUCLEIC ACIDS WITH DISULFIDE-CROSSLINKED CATIONIC COMPONENTS FOR TRANSFECTION AND IMMUNOSTIMULATION

This application is a National Stage of PCT/EP2011/003,719, filed Jul. 25, 2011 which claims priority to European Patent No. 10007992.0, filed Jul. 30, 2010 and U.S. Provisional Application No. 61/369,549, filed Jul. 30, 2010, the disclosures of which are incorporated herein by reference in their entirety.

The instant application contains a Sequence Listing which has been submitted in ASCII format via EFS-Web and is hereby incorporated by reference in its entirety. Said ASCII copy, created on Aug. 26, 2011, is named 067802_CU17_US1_Sequence.txt and is 94519 bytes in size.

The present invention is directed to a polymeric carrier cargo complex, comprising as a cargo at least one nucleic acid (molecule) and as a (preferably non-toxic and non-immunogenic) polymeric carrier disulfide-crosslinked cationic components. The inventive polymeric carrier cargo complex allows for both efficient transfection of nucleic acids into cells in vivo and in vitro and/or for induction of an (innate and/or adaptive) immune response, preferably dependent on the nucleic acid to be transported as a cargo. The present invention also provides pharmaceutical compositions, particularly vaccines, comprising the inventive polymeric carrier cargo complex and optionally an antigen, as well as the use of the inventive polymeric carrier cargo complex and optionally an antigen for transfecting a cell, a tissue or an organism, for (gene-)therapeutic purposes as disclosed herein, and/or as an immunostimulating agent or adjuvant, e.g. for eliciting an immune response for the treatment or prophylaxis of diseases as mentioned above. Finally, the invention relates to kits containing the inventive polymeric carrier cargo complex, the inventive pharmaceutical composition and/or the inventive vaccine or any of its components in one or more parts of the kit.

Many diseases today require administration of adjuvants to provide an innate immune response and, optionally, to support an adaptive immune response, particularly in the context of vaccinations. Some but not necessarily all of these diseases additionally or alternatively require administration of peptide-, protein-, and nucleic acid-based drugs, e.g. the transfection of nucleic acids into cells or tissues. These requirements usually represent different aspects in the treatment of such diseases and are typically difficult to address in one approach. As a consequence, the prior art usually handles such aspects via separate approaches.

In the above context, vaccination is generally believed to be one of the most effective and cost-efficient ways to prevent or treat diseases. Nevertheless several problems in vaccine development have proved difficult to solve: Vaccines are often inefficient for the very young and the very old; many vaccines need to be given several times, and the protection they confer wanes over time, requiring booster administrations, and, for some diseases such as HIV, development of efficient vaccines is urgently needed. As generally accepted, many of these vaccines would be enabled or improved if they could elicit a stronger and more durable immune response.

Accordingly, the development of new efficient and safe adjuvants for vaccination purposes which support induction and maintenance of an adaptive immune response by initiating or boosting a parallel innate immune response represents a main challenging problem.

Adjuvants are usually defined as compounds that can increase and/or modulate the intrinsic immunogenicity of an antigen. To reduce negative side effects, new vaccines have a more defined composition that often leads to lower immunogenicity compared with previous whole-cell or virus-based vaccines. Adjuvants are therefore required to assist new vaccines to induce potent and persistent immune responses, with the additional benefit that less antigen and fewer injections are needed. Now it is clear that the adaptive immune response mainly depends on the level and specificity of the initial danger signals perceived by innate immune cells following infection or vaccination (Guy, B. (2007), Nat Rev Microbiol 5(7): 505-17.). In particular for new generation vaccine candidates, which will increasingly comprise highly purified recombinant proteins and, although very safe, are poorly immunogenic, efficient adjuvants will become increasingly necessary.

Unfortunately, only a few licensed adjuvants are available so far. Most prominent is Alum, which is known to be safe, but also represents a very weak adjuvant. Many further adjuvants have been developed, e.g. including the administration of pathogens, CpG-nucleotides, etc. Most of these new or "established" adjuvants, however, still do not satisfy the above requirements, since many new and emerging problems have to be considered and solved. These problems inter alia include new and re-emerging infectious diseases, repeated administrations, threat of pandemic flu, etc.

Furthermore, the new vaccine targets are usually more difficult to develop and—due to their specifically tailored immune responses—require more potent adjuvants to enable success. Moreover, there are still a significant number of important pathogens for which we do not even have effective vaccines at present. This represents a very challenging future target. To enable vaccine development against such targets, more potent adjuvants will be necessary. Such new adjuvants will need to offer advantages, including more heterologous antibody responses, covering pathogen diversity, induction of potent functional antibody responses, ensuring pathogen killing or neutralization and induction of more effective T cell responses, for direct and indirect pathogen killing, particularly the induction of cytotoxic T cells which are part of a Th1 immune response. In addition, adjuvants may be necessary to achieve more pragmatic effects, including antigen dose reduction and overcoming antigen competition in combination vaccines. Moreover, against the background of an aging population, which is increasingly susceptible to infectious diseases, new adjuvants will be necessary to overcome the natural deterioration of the immune response with age (O'Hagan, D. T. and E. De Gregorio (2009), Drug Discov Today 14(11-12): 541-51.).

The review of O'Hagan (2009; supra) summarizes some reasons for the urgent need of new effective adjuvants e.g. the requirement of a lower antigen dose in vaccines, the necessity to increase the breadth of an immune response and the heterologous activity, to enable complex combination vaccines, and to overcome antigenic competition, to overcome limited immune response in some groups of the population, such as the elderly, the young children, and infants, patients with chronic diseases and the immunocompromised, to increase effector T cell response and antibody titers, to induce protective responses more rapidly and also to extend the duration of response by enhancing memory B and T cell responses.

Summarizing the above, new efficient and safe immunostimulating agents or adjuvants are required, which are preferably efficient in inducing an innate immune response, particularly in inducing the anti-viral cytokine IFN-alpha; which are, preferably, also efficient in supporting an adaptive immune response; safe, i.e. not associated with any long-term effects; which are well tolerated; which are available via a simple synthetic pathway; which exhibit low cost storage conditions (particularly feasible lyophilisation); which require simple and inexpensive components; which are biodegradable; which are compatible with many different kinds of vaccine antigens; which are capable of codelivery of antigen and immune potentiator, etc.

As already explained above adjuvants or immunostimulating agents usually act via their capability to induce an innate immune response. The innate immune system forms the dominant system of host defense in most organisms and comprises barriers such as humoral and chemical barriers including, e.g., inflammation, the complement system and cellular barriers. The innate immune system is typically based on a small number of receptors, called pattern recognition receptors. They recognize conserved molecular patterns that distinguish foreign organisms, like viruses, bacteria, fungi and parasites, from cells of the host. Such pathogen-associated molecular patterns (PAMP) include viral nucleic acids, components of bacterial and fungal walls, flagellar proteins, and more. The first family of pattern recognition receptors (PAMP receptors) studied in detail was the Toll-like receptor (TlM) family. TLRs are transmembrane proteins which recognize ligands of the extracellular milieu or of the lumen of endosomes. Following ligand-binding they transduce the signal via cytoplasmic adaptor proteins which leads to triggering of a host-defence response and entailing production of antimicrobial peptides, proinflammatory chemokines and cytokines, antiviral cytokines, etc. (see e.g. Meylan, E., J. Tschopp, et al. (2006), Nature 442(7098): 39-44). Further relevant components of the immune system include e.g. the endosomal TLRs, cytoplasmic receptors, Type 1 interferons and cytoplasmic receptors. Therefore, the immunostimulating agents or adjuvants are defined herein preferably as inducers of an innate immune response, which active pattern recognition receptors (PAMP receptors). Hereby, a cascade of signals is elicited, which e.g. may result in the release of cytokines (e.g. IFN-alpha) supporting the innate immune response. Accordingly, it is preferably a feature of an immunostimulating agent or adjuvant to bind to such receptors and activate such PAMP receptors. Ideally, such as an agent or adjuvant additionally supports the adaptive immune response by e.g. shifting the immune response such that the preferred class of Th cells is activated. Depending on the disease or disorder to be treated a shift to a Th1-based immune reponse may be preferred or, in other cases, a shift to a Th2 immune response may be preferred.

In the prior art there are some promising adjuvant candidates which fulfil at least some, but not all, of the above defined required characteristics.

As an example, among the above developed new adjuvants, some nucleic acids like CpG DNA oligonucleotides or isRNA (immunostimulating RNA) turned out to be promising candidates for new immunostimulating agents or adjuvants as they allow the therapeutic or prophylactic induction of an innate immune response. Comprehensibly, such nucleic acid based adjuvants usually have to be delivered effectively to the site of action to allow induction of an effective innate immune response without unnecessary loss of adjuvant activity and, in some cases, without the necessity to increase the administered volume above systemically tolerated levels.

One approach to solve this issue may be the transfection of cells which are part of the innate immune system (e.g. dendritic cells, plasmacytoid dendritic cells (pDCs)) with immunostimulatory nucleic acids, which are ligands of PAMP receptors, (e.g. Toll-like receptors (TLRs)), and thus may lead to immunostimulation by the nucleic acid ligand. Further approaches may be the direct transfection of nucleic acid based adjuvants. All of these approaches, however, are typically impaired by inefficient delivery of the nucleic acid and consequently diminished adjuvant activity, in particular when administered locally.

However, one main disadvantage of such nucleic acid based adjuvant approaches until today is their limited ability to cross the plasma membrane of mammalian cells, resulting in poor cellular access and inadequate therapeutic efficacy. Until today this hurdle represents a major challenge for nucleic acid transfection based applications, e.g. biomedical developments and accordingly the commercial success of many biopharmaceuticals (see e.g. Foerg, C. & Merkle, H. P., *J Pharm Sci* 97, 144-62 (2008).

Transfection of nucleic acids or genes into cells or tissues has been investigated up to date in the context of in vitro transfection purposes and in the context of gene therapeutic approaches. However, no adjuvants are available so far which are based on such gene delivery techniques which are efficient and safe, in particular no licensed adjuvants. This is presumably due to the complex requirements of adjuvants in general in combination with stability issues to be solved in the case of nucleic acid based adjuvants.

Nevertheless, transfection of nucleic acids or genes into cells or tissues for eliciting an (innate and/or adaptive) immune response appears to provide a promising approach to provide new adjuvants.

However, many of these approaches utilize transfection of nucleic acids or genes into cells or tissues without induction of an innate immune response. There even some gene therapeutic therapies, which have to strictly avoid induction of an innate immune response. Even in the rare cases, where vaccination is carried out to induce an adaptive antigen-specific immune response using administration of nucleic acids, e.g. in tumour vaccinations using DNA or mRNA encoded antigens, induction of an adaptive immune response is typically carried out as an active immunization against the encoded antigen but not as an accompanying adjuvant therapy and thus requires additional administration of a separate adjuvant to induce an innate immune response.

Even if a lot of transfection methods are known in the art, transfer or insertion of nucleic acids or genes into an individual's cells still represents a major challenge today and is not yet solved satisfactorily. To address this complex issue a variety of methods were developed in the last decade. These include transfection by calcium phosphate, cationic lipids, cationic polymers, and liposomes. Further methods for transfection are electroporation and viral transduction.

However, as known to a skilled person, systems for transfer or insertion of nucleic acids or genes have to fulfil several requirements for in vivo applications which include efficient nucleic acid delivery into an individual's cells with high functionality, protection of the nucleic acid against ubiquitously occurring nucleases, release of the nucleic acid in the cell, no safety concerns, feasible manufacturing in a commercially acceptable form amenable to scale-up and storage stability under low cost conditions (e.g feasible lyophilisation). These requirements are to be added to the complex requirements of an adjuvant particularly if it is in the form of a nucleic acid as outlined above.

Some successful strategies for the transfer or insertion of nucleic acids or genes available today rely on the use of viral vectors, such as adenoviruses, adeno-associated viruses, retroviruses, and herpes viruses. Viral vectors are able to mediate gene transfer with high efficiency and the possibility of long-term gene expression. However, the acute immune response ("cytokine storm"), immunogenicity, and insertion mutagenesis uncovered in gene therapy clinical trials have raised serious safety concerns about some commonly used viral vectors.

Another solution to the problem of transfer or insertion of nucleic acids or genes may be found in the use of non-viral vectors. Although non-viral vectors are not as efficient as viral vectors, many non-viral vectors have been developed to provide a safer alternative. Methods of non-viral nucleic acid delivery have been explored using physical (carrier-free nucleic acid delivery) and chemical approaches (synthetic vector-based nucleic acid delivery). Physical approaches usually include needle injection, electroporation, gene gun, ultrasound, and hydrodynamic delivery, employ a physical force that permeates the cell membrane and facilitates intracellular gene transfer. The chemical approaches typically use synthetic or naturally occurring compounds (e.g. cationic lipids, cationic polymers, lipid-polymer hybrid systems) as carriers to deliver the nucleic acid into the cells. Although significant progress has been made in the basic science and applications of various nonviral nucleic acid delivery systems, the majority of non-viral approaches are still much less efficient than viral vectors, especially for in vivo gene delivery (see e.g. Gao, X., Kim, K. & Liu, D., *AAPS J* 9, E92-104 (2007)).

Such transfection agents as defined above typically have been used successfully solely in in vitro reactions. For application of nucleic acids in vivo, however, further requirements have to be fulfilled. For example, complexes between nucleic acids and transfection agents have to be stable in physiological salt solutions with respect to agglomerisation. Furthermore, such complexes typically must not interact with parts of the complement system of the host and thus must not be immunogenic itself as the carrier itself shall not induce an adaptive immune response in the individual. Additionally, the complex shall protect the nucleic acid from early extracellular degradation by ubiquitously occurring nucleases.

In the art many transfection reagents are available, especially cationic lipids, which show excellent transfection activity in cell culture. However, most of these transfection reagents do not perform well in the presence of serum, and only a few are active in vivo. A dramatic change in size, surface charge, and lipid composition occurs when lipoplexes are exposed to the overwhelming amount of negatively charged and often amphipathic proteins and polysaccharides that are present in blood, mucus, epithelial lining fluid, or tissue matrix. Once administered in vivo, lipoplexes tend to interact with negatively charged blood components and form large aggregates that could be absorbed onto the surface of circulating red blood cells, trapped in a thick mucus layer, or embolized in microvasculatures, preventing them from reaching the intended target cells in the distal location. Some even undergo dissolution after they are introduced to the blood circulation (see e.g. Gao, X., Kim, K. & Liu, D., *AAPS J* 9, E92-104 (2007)).

One more promising approach utilizes cationic polymers. Cationic polymers turned out to be efficient in transfection of nucleic acids, as they can tightly complex and condense a negatively charged nucleic acid. Thus, a number of cationic polymers have been explored as carriers for in vitro and in vivo gene delivery. These include polyethylenimine (PEI), polyamidoamine and polypropylamine dendrimers, polyallylamine, cationic dextran, chitosan, cationic proteins and cationic peptides. Although most cationic polymers share the function of condensing DNA into small particles and facilitate cellular uptake via endocytosis through charge-charge interaction with anionic sites on cell surfaces, their transfection activity and toxicity differs dramatically.

Only in one approach in the art, the immunostimulatory effect of RNA complexed to short cationic peptides was demonstrated by Fotin-Mleczek et al. (WO 2009/030481). These formulations appear to efficiently induce the cytokine production in immunocompetent cells. Unfortunately Fotin-Mleczek et al. did not assess the induction of the preferable anti-viral cytokine IFN-α by these complexes. Additionally, these complexes turned out to be unstable during lyophilisation.

In the above context, cationic polymers exhibit better transfection efficiency with rising molecular weight. However, a rising molecular weight also leads to a rising toxicity of the cationic polymer. In this above context, (high molecular weight) PEI is perhaps the most active and most studied polymer for transfection of nucleic acids, in particular for gene delivery purposes. Unfortunately, it exhibits the same drawback due to its non-biodegradable nature and toxicity. Furthermore, even though polyplexes formed by high molecular weight polymers exhibit improved stability under physiological conditions, data have indicated that such polymers can hinder vector unpacking. To overcome this negative impact, Read et al. (see Read, M. L. et al., *J Gene Med.* 5, 232-245 (2003); and Read, M. L. et al., *Nucleic Acids Res* 33, e86 (2005)) developed a new type of synthetic vector based on a linear reducible polycation (RPC) prepared by oxidative polycondensation of the peptide Cys-Lys$_{10}$-Cys. This peptide Cys-Lys$_{10}$-Cys can be cleaved by the intracellular environment to facilitate release of nucleic acids. In this context, Read et al. (2003, supra) could show that polyplexes formed by these RPCs are destabilised by reducing conditions enabling efficient release of DNA and mRNA. However, examining the transfection efficiency in vitro Read et al. (2003, supra) also observed that N/P (nitrogen to phosphor atoms) ratios of 2 were unsatisfying and higher N/P ratios were necessary to improve transfection efficiency. Additionally, Read et al. (2003, supra) observed that chloroquine or the cationic lipid DOTAP was additionally necessary to enhance transfection efficiency to adequate levels. As a consequence, Read et al. (2005, supra) included histidine residues into the RPCs which have a known endosomal buffering capacity and showed that such histidine-rich RPCs can be cleaved by the intracellular reducing environment. This approach enabled efficient cytoplasmic delivery of a broad range of nucleic acids, including plasmid DNA, mRNA and siRNA molecules without the requirement for the endosomolytic agent chloroquine.

Unfortunately, neither Read et al. (2003, supra) nor Read et al. (2005, supra) did assess as to whether RPCs can be directly used for in vivo applications. In their study in 2005, transfections were performed in the absence of serum to avoid masking the ability of histidine residues to enhance gene transfer that may have arisen from binding of serum proteins to polyplexes restricting cellular uptake. Preliminary experiments, however, indicated that the transfection properties of histidine-rich RPC polyplexes can be affected by the presence of serum proteins with a 50% decrease in GFP-positive cells observed in 10% FCS. For in vivo application Read et al. (2005, supra) proposed modifications with the hydrophilic polymer poly-[N-(2hydroxy-propyl)methacrylamide]. Unfortunately, they could not prevent aggregation of polyplexes and binding of polycationic complexes to serum proteins. Furthermore, strong cationic charged complexes are formed (positive zeta potential) when complexing the nucleic acid due to the large excess of cationic polymer, which is characterized by the high N/P ratio. Accordingly, such complexes are only of limited use in vivo due to their strong tendency of salt induced agglomeration and interactions with serum contents (opsonization). Additionally, these (positively charged) complexes may excite complement activation, when used for purposes of gene therapy. It has also turned out that these positively charged RPC based complexes showed poor translation of the nucleic acid cargo subsequent to local administration into the dermis.

In an approach similar to Read et al. McKenzie et al. (McKenzie, D. L., K. Y. Kwok, et al. (2000), J Biol Chem 275(14): 9970-7. and McKenzie, D. L., E. Smiley, et al. (2000), Bioconjug Chem 11(6): 901-9) developed cross-linking peptides as gene delivery agents by inserting multiple cysteines into short synthetic peptides. In their studies they examined the optimal complex formation with DNA and as a result they could show that an N/P ratio of at least 2 is necessary for fully formed peptide DNA condensates. Therefore only positively charged complexes appeared to show optimal DNA condensation. In contrast to these data they proposed the development of negatively charged complexes for in vivo gene delivery, since it was shown in previous studies that intravenous application of electropositive DNA condensates leads to rapid opsonisation and nonspecific biodistribution to lung and liver (Collard, W. T., Evers, D. L., McKenzie, D. L., and Rice, K. G. (2000), Carbohydr. Res. 323, 176-184). Therefore McKenzie et al. (2000; supra) proposed the derivatization of the carriers with polyethylene glycol and targeting ligands. To be noted, the approach of McKenzie et al. (2000, supra) is additionally subject of a patent (U.S. Pat. No. 6,770,740 B1), which particularly discloses the transfection of coding nucleic acids, antisense nucleic acids and ribozymes.

Thus, in vivo application of nucleic acids appears to be still one of the most challenging problems because plasma proteins with anionic charges may non-specifically bind to positively charged complexes and rapidly remove them e.g. via the reticulo-endothelial system. Opsonization and activation of the complement system by cationic complexes are additional physiological phenomena that can participate in lowering the efficacy of in vivo administered cationic complexes. This particularly applies to administration of nucleic acid-based drugs, e.g. the transfection of nucleic acids into cells or tissues, particularly if the expression of an encoded protein or peptide or transcription of an RNA of the transfected nucleic acid is intended.

Summarizing the above, the prior art does not provide feasible means or methods, which, on the one hand side, allow to establish efficient and safe adjuvants for vaccination purposes, and which, on the other hand side, are furthermore suited for in vivo delivery of nucleic acids, in particular for compacting and stabilizing a nucleic acid for the purposes of nucleic acid transfection in vivo without exhibiting the negative side effects as discussed above. More precisely, no means or methods are known in the prior art in the above context, which are, on the one hand side, stable enough to carry a nucleic acid cargo to the target before they are metabolically cleaved, and which, on the other hand side, can be cleared from the tissue before they can accumulate and reach toxic levels. In addition no means or method is known, which, additional to the above requirements, induces a desirable pattern of cytokines, particularly the anti viral cytokine IFN-α. Accordingly, it is the object of the present invention to provide such means or methods, which address these problems.

The object underlying the present invention is solved by the subject matter of the present invention, preferably by the subject matter of the attached claims.

According to a first embodiment, the object underlying the present invention is solved by a polymeric carrier cargo complex, comprising
   a) (as a carrier) a polymeric carrier formed by disulfide-crosslinked cationic components, and
   b) (as a cargo) at least one nucleic acid (molecule),
preferably for use as a medicament, more preferably for use as an immunostimulating agent or adjuvant, e.g. in the treatment of a disease as defined herein.

Alternatively, the object underlying the present invention is solved by a polymeric carrier cargo complex, consisting of
   a) a polymeric carrier formed by disulfide-crosslinked cationic components (as a carrier), and
   b) at least one nucleic acid (molecule) (as a cargo),
preferably for use as a medicament, more preferably for use as an immunostimulating agent or adjuvant, e.g. in the treatment of a disease as defined herein.

The term "immunostimulating agent" is typically understood not to include agents as e.g. antigens (of whatever chemical structure), which elicit an adaptive/cytotoxic immune response, e.g. a "humoral" or "cellular" immune response, in other words elicit immune reponses (and confer immunity by themselves) which are characterized by a specific response to structural properties of an antigen recognized to be foreign by immune competent cells. Rather, by "immunostimulating agent", it is typically understood to mean agents/compounds/complexes which do not trigger any adaptive/cytotoxic immune response by themselves, but which may exclusively enhance such an adaptive/cytotoxic immune response in an unspecific way, by e.g. activating "PAMP" receptors and thereby triggering the release of cytokines which support the actual adaptive/cytotoxic immune response. Accordingly, any immunostimulation by agents (e.g. antigens) which evoke an adaptive and/or cytotoxic immune response by themselves (conferring immunity by themselves directly or indirectly) is typically disclaimed by the phrase "immunostimulating agent".

The term "adjuvant" is also understood not to comprise agents which confer immunity by themselves. Accordingly, adjuvants do not by themselves confer immunity, but assist the immune system in various ways to enhance the antigen-specific immune response by e.g. promoting presentation of an antigen to the immune system. Hereby, an adjuvant may preferably e.g. modulate the antigen-specific immune response by e.g. shifting the dominating Th1-based antigen specific response to a more Th2-based antigen specific response or vice versa. Accordingly, the terms "immunostimulating agent" and "adjuvant" in the context of the present invention are typically understood to mean agents, compounds or complexes which do not confer immunity by themselves, but exclusively support the immune reponse in an unspecific way (in contrast to an antigen-specific immune response) by effects, which mosulate the antigen-specific (adaptive cellular and/or humoral immune response) by unspecific measures, e.g. cytokine expression/secretion, improved antigen presentation, shifting the nature of the arms of the immune response etc. Accordingly, any agents evoking by themselves immunity are typically disclaimed by the terms "adjuvant" or "immunostimulating agent".

The inventive polymeric carrier cargo complex allows provision of efficient and safe adjuvants for vaccination purposes and carriers for transfection, either in the field of vaccination, adjuvant therapy or gene therapeutic applications, etc. Advantageously, the inventive polymeric carrier cargo complex is suited for in vivo delivery of nucleic acids, in particular for compacting and stabilizing a nucleic acid for the purposes of nucleic acid transfection without exhibiting the negative side effects of high-molecular weight polymers as discussed above, such as no or bad biodegradability or even high toxicity, agglomeration, low transfection activity in vivo, etc. The inventive polymeric carrier cargo complex also provides for efficient nucleic acid transfer in vivo particularly via intradermal or intramuscular routes, including serum stability, salt stability, efficient uptake, no complement activation, nucleic acid release, etc. Such an inventive polymeric carrier cargo complex, when provided as an adjuvant, furthermore supports induction and maintenance of an adaptive immune response by initiating or boosting a parallel innate immune response. Additionally, the inventive polymeric carrier cargo complex exhibits excellent storage stability, particularly during lyophilization.

The inventive polymeric carrier cargo complex as defined above comprises as one component a polymeric carrier formed by disulfide-crosslinked cationic components. The term "cationic component" typically refers to a charged molecule, which is positively charged (cation) at a pH value of about 1 to 9, preferably of a pH value of or below 9, of or below 8, of or below 7, most preferably at physiological pH values, e.g. about 7.3 to 7.4. Accordingly, a cationic peptide, protein or polymer according to the present invention is positively charged under physiological conditions, particularly under physiological salt conditions of the cell in vivo. The definition "cationic" may also refer to "polycationic" components.

In this context the cationic components, which form basis for the polymeric carrier of the inventive polymeric carrier cargo complex by disulfide-crosslinkage, are typically selected from any suitable cationic or polycationic peptide, protein or polymer suitable for this purpose, particular any cationic or polycationic peptide, protein or polymer capable to complex a nucleic acid as defined according to the present invention, and thereby preferably condensing the nucleic acid. The cationic or polycationic peptide, protein or polymer, is preferably a linear molecule, however, branched cationic or polycationic peptides, proteins or polymers may also be used.

Each cationic or polycationic protein, peptide or polymer of the polymeric carrier contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

Each cationic or polycationic protein, peptide or polymer or any further component of the polymeric carrier is preferably linked to its neighbouring component(s) (cationic proteins, peptides, polymers or other components) via disulfide-crosslinking. Preferably, the disulfide-crosslinking is a (reversible) disulfide bond (—S—S—) between at least one cationic or polycationic protein, peptide or polymer and at least one further cationic or polycationic protein, peptide or polymer or other component of the polymeric carrier. The disulfide-crosslinking is typically formed by condensation of —SH-moieties of the components of the polymeric carrier particularly of the cationic components. Such an —SH-moiety may be part of the structure of the cationic or polycationic protein, peptide or polymer or any further component of the polymeric carrier prior to disulfide-crosslinking or may be added prior to disulfide-crosslinking by a modification as defined below. In this context, the sulphurs adjacent to one component of the polymeric carrier, necessary for providing a disulfide bond, may be provided by the component itself, e.g. by a —SH moiety as defined herein or may be provided by modifying the component accordingly to exhibit a —SH moiety. These —SH-moieties are typically provided by each of the component, e.g. via a cysteine or any further (modified) amino acid or compound of the component, which carries a —SH moiety. In the case that the cationic component or any further component of the polymeric carrier is a peptide or protein it is preferred that the —SH moiety is provided by at least one cysteine residue. Alternatively, the component of the polymeric carrier may be modified accordingly with a —SH moiety, preferably via a chemical reaction with a compound carrying a —SH moiety, such that each of the components of the polymeric carrier carries at least one such —SH moiety. Such a compound carrying a —SH moiety may be e.g. an (additional) cysteine or any further (modified) amino acid or compound of the component of the polymeric carrier, which carries a —SH moiety. Such a compound may also be any non-amino compound or moiety, which contains or allows to introduce a —SH moiety into the component as defined herein. Such non-amino compounds may be attached to the component of the polymeric carrier according to the present invention via chemical reactions or binding of compounds, e.g. by binding of a 3-thio propionic acid or 2-iminothiolane (Traut's reagent), by amide formation (e.g. carboxylic acids, sulphonic acids, amines, etc.), by Michael addition (e.g maleinimide moieties, $\alpha,\beta$ unsaturated carbonyls, etc.), by click chemistry (e.g. azides or alkines), by alkene/alkine methatesis (e.g. alkenes or alkines), imine or hydrozone formation (aldehydes or ketons, hydrazins, hydroxylamines, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. In some cases the —SH moiety may be masked by protecting groups during chemical attachment to the component. Such protecting groups are known in the art and may be removed after chemical coupling. In each case, the —SH moiety, e.g. of a cysteine or of any further (modified) amino acid or compound, may be present at the terminal ends or internally at any position of the component of the polymeric carrier. As defined herein, each of the components of the polymeric carrier typically exhibits at least one —SH-moiety, but may also contain two, three, four, five, or even more —SH-moieties. Additionally to binding of cationic components a —SH moiety may be used to attach further components of the polymeric carrier as defined herein, particularly an amino acid component, e.g. antigen epitopes, antigens, antibodies, cell penetrating peptides (e.g. TAT), ligands, etc.

As defined above, the polymeric carrier of the inventive polymeric carrier cargo molecule is formed by disulfide-crosslinked cationic (or polycationic) components.

According to one first alternative, at least one cationic (or polycationic) component of the polymeric carrier may be selected from cationic or polycationic peptides or proteins. Such cationic or polycationic peptides or proteins preferably exhibit a length of about 3 to 100 amino acids, preferably a length of about 3 to 50 amino acids, more preferably a length of about 3 to 25 amino acids, e.g. a length of about 3 to 10; 5 to 20; 5 to 15; 8 to 15, 16 or 17; 10 to 15, 16, 17, 18, 19, or 20; or 15 to 25 amino acids. Alternatively or additionally, such cationic or polycationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa.

In the specific case that the cationic component of the polymeric carrier comprises a cationic or polycationic peptide or protein, the cationic properties of the cationic or polycationic peptide or protein or of the entire polymeric carrier, if the polymeric carrier is entirely composed of cationic or polycationic peptides or proteins, may be determined upon its content of cationic amino acids. Preferably, the content of cationic amino acids in the cationic or polycationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the cationic or polycationic peptide or protein, or in the entire polymeric carrier, if the polymeric carrier is entirely composed of cationic or polycationic peptides or proteins, is 100%.

In this context, cationic amino acids are preferably the naturally occurring amino acids Arg (Arginine), Lys (Lysine), His (Histidine), and Orn (Ornithin). However, in a broader sense any (non-natural) amino acid carrying a cationic charg on its side chain may also be envisaged to carry out the invention. Preferably, however, are those cationic amino acids, the side chains of which are positively charged under physiological pH conditions. In a more preferred embodiment, these amino acids are Arg, Lys, and Orn.

Preferably, such cationic or polycationic peptides or proteins of the polymeric carrier, which comprise or are additionally modified to comprise at least one —SH moiety, are selected from, without being restricted thereto, cationic peptides or proteins such as protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such cationic or polycationic peptides or proteins of the polymeric carrier, which comprise or are additionally modified to comprise at least one —SH moeity, are selected from, without being restricted thereto, following cationic peptides having the following sum formula (I):

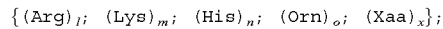

$$\{(Arg)_l; (Lys)_m; (His)_n; (Orn)_o; (Xaa)_x\};$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred. Even more preferred peptides of this formula are oligoarginines such as e.g. $Arg_7$, $Arg_8$, $Arg_9$, $Arg_{12}$, $His_3Arg_9$, $Arg_9His_3$, $His_6Arg_9His_3$, $His_6Arg_9His_3$, $His_6Arg_4His_3$, $His_6Arg_4His_6$, $TyrSer_2Arg_9Ser_2Tyr$, $(ArgLysHis)_4$, $Tyr(ArgLysHis)_2Arg$, etc.

According to a particular preferred embodiment, such cationic or polycationic peptides or proteins of the polymeric carrier having the empirical sum formula (I) as shown above, may, without being restricted thereto, comprise at least one of the following subgroup of formulae:

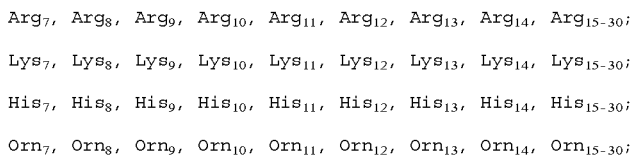

$Arg_7$, $Arg_8$, $Arg_9$, $Arg_{10}$, $Arg_{11}$, $Arg_{12}$, $Arg_{13}$, $Arg_{14}$, $Arg_{15-30}$;

$Lys_7$, $Lys_8$, $Lys_9$, $Lys_{10}$, $Lys_{11}$, $Lys_{12}$, $Lys_{13}$, $Lys_{14}$, $Lys_{15-30}$;

$His_7$, $His_8$, $His_9$, $His_{10}$, $His_{11}$, $His_{12}$, $His_{13}$, $His_{14}$, $His_{15-30}$;

$Orn_7$, $Orn_8$, $Orn_9$, $Orn_{10}$, $Orn_{11}$, $Orn_{12}$, $Orn_{13}$, $Orn_{14}$, $Orn_{15-30}$;

According to a further particularly preferred embodiment, cationic or polycationic peptides or proteins of the polymeric carrier, having the empirical sum formula (I) as shown above and which comprise or are additionally modified to comprise at least one —SH moeity, may be preferably selected from, without being restricted thereto, at least one of the following subgroup of formulae. The following formulae (as with empirical formula (I)) do not specify any amino acid order, but are intended to reflect empirical formulae by exclusively specifying the (number of) amino acids as components of the respective peptide. Accordingly, as an example, empirical formula $Arg_{(7-29)}Lys_1$ is intended to mean that peptides falling under this formula contain 7 to 19 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

$Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn2$, $Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$, $Arg_{(1-26)}Lys_4$, $Arg_{(1-26)}His_4$, $Arg_{(1-26)}Orn_4$, $Lys_{(1-26)}His_4$, $Lys_{(1-26)}Orn_4$, $His_{(1-26)}Orn_4$, $Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;

$Arg_{(2-27)}Lys_2His_1$, $Arg_{(2-27)}Lys_1His_2$, $Arg_{(2-27)}Lys_2Orn_1$, $Arg_{(2-27)}Lys_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_2Lys_{(2-27)}Orn_1$, $Arg_1Lys_{(2-27)}Orn_2$, $Lys_{(2-27)}His_2Orn_1$, $Lys_{(2-27)}His_1Orn_2$, $Arg_2Lys_1His_{(2-27)}$, $Arg_1Lys_2His_{(2-27)}Orn_1$, $Arg_1His_{(2-27)}$ $Orn_2$, $Lys_2His_{(2-27)}Orn_1$, $Lys_1His_{(2-27)}Orn_2$;

$Arg_{(1-26)}Lys_3His_1$, $Arg_{(1-26)}Lys_2His_2$, $Arg_{(1-26)}Lys_1His_3$, $Arg_{(1-26)}Lys_3Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_2Lys_{(1-26)}Orn_2$, $Arg_1Lys_{(1-26)}Orn_3$, $Lys_{(1-26)}His_3Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_3His_{(1-26)}$, $Arg_3His_{(1-26)}Orn_1$, $Arg_2His_{(1-26)}Orn_2$, $Arg_1His_{(1-26)}Orn_3$, $Lys_3His_{(1-26)}Orn_1$, $Lys_2His_{(1-26)}Orn_2$, $Lys_1His_{(1-26)}Orn_3$;

$Arg_{(2-27)}Lys_1His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;

$Arg_{(1-26)}Lys_2His_1Orn_1$, $Arg_{(1-26)}Lys_1His_2Orn_1$, $Arg_{(1-26)}Lys_1His_1Orn_2$, $Arg_2Lys_{(1-26)}His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}Orn_1$, $Arg_1Lys_1His_{(1-26)}Orn_2$, $Arg_2Lys_1His_1Orn_{(1-26)}$, $Arg_1Lys_2His_1Orn_{(1-26)}$, $Arg_1Lys_1His_2Orn_{(1-26)}$;

According to a further particular preferred embodiment, cationic or polycationic peptides or proteins of the polymeric carrier, having the empirical sum formula (I) as shown above and which comprise or are additionally modified to comprise at least one —SH moiety, may be, without being restricted thereto, selected from the subgroup consisting of generic formulas Arg, (also termed as $R_7$), $Arg_9$ (also termed $R_9$), Arg (also termed as $R_{12}$).

According to a one further particular preferred embodiment, the cationic or polycationic peptide or protein of the polymeric carrier, when defined according to formula $\{(Arg)_i;(Lys)_m;(His)_n;(Orn)_o;(Xaa)_x\}$ (formula (I)) as shown above and which comprise or are additionally modified to comprise at least one —SH moiety, may be, without being restricted thereto, selected from subformula (Ia):

$$\{(Arg)_i;(Lys)_m;(His)_n;(Orn)_o;(Xaa')_x(Cys)_y\} \qquad \text{formula (Ia)}$$

wherein $(Arg)_i;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula $(Arg)_i;(Lys)_m;(His)_n;(Orn)_o;(Xaa)_x$ (formula (I)) as shown above, comprises or has been modified with at least one cysteine as —SH moiety in the above meaning such that the cationic or polycationic peptide as cationic component carries at least one cysteine, which is capable to form a disulfide bond with other components of the polymeric carrier.

According to another particular preferred embodiment, the cationic or polycationic peptide or protein of the polymeric carrier, when defined according to formula $\{(Arg)_i;(Lys)_m;(His)_n;(Orn)_o;(Xaa)_x\}$ (formula (I)) as shown above, may be, without being restricted thereto, selected from subformula (Ib):

$$Cys_1\{(Arg)_i;(Lys)_m;(His)_n;(Orn)_o;(Xaa)_x\}Cys_2 \qquad \text{(formula (Ib))}$$

wherein empirical formula $\{(Arg)_i;(Lys)_m;(His)_n;(Orn)_o;(Xaa)_x\}$ (formula (I)) is as defined herein and forms a core of an amino acid sequence according to (semiempirical) formula (I) and wherein $Cys_1$ and $Cys_2$ are Cysteines proximal to, or terminal to $(Arg)_i;(Lys)_m;(His)_n;(Orn)_o;(Xaa)_x$. Exemplary examples may comprise any of the above sequences flanked by two Cys and following sequences:

$Cys(Arg_7)Cys$, $Cys(Arg_8)Cys$, $Cys(Arg_9)Cys$, $Cys(Arg_{10})Cys$, $Cys(Arg_{11})Cys$, $Cys(Arg_{12})Cys$, $Cys(Arg_{13})Cys$, $Cys(Arg_{14})Cys$, $Cys(Arg_{15})Cys$, $Cys(Arg_{16})Cys$, $Cys(Arg_{17})Cys$, $Cys(Arg_{18})Cys$, $Cys(Arg_{19})Cys$, $Cys(Arg_{20})Cys$ (SEQ ID NOs: 1-14):

$CysArg_7Cys$

-continued

```
                                                                    (SEQ ID NO. 1)
Cys-Arg-Arg-Arg-Arg-Arg-Arg-Cys

CysArg₈Cys
                                                                    (SEQ ID NO. 2)
Cys-Arg-Arg-Arg-Arg-Arg-Arg-Arg-Cys

CysArg₉Cys:
                                                                    (SEQ ID NO. 3)
Cys-Arg-Arg-Arg-Arg-Arg-Arg-Arg-Arg-Cys

CysArg₁₀Cys
                                                                    (SEQ ID NO. 4)
Cys-Arg-Arg-Arg-Arg-Arg-Arg-Arg-Arg-Arg-Cys

CysArg₁₁Cys
                                                                    (SEQ ID NO. 5)
Cys-Arg-Arg-Arg-Arg-Arg-Arg-Arg-Arg-Arg-Arg-Cys

CysArg₁₂Cys:
                                                                    (SEQ ID NO. 6)
Cys-Arg-Arg-Arg-Arg-Arg-Arg-Arg-Arg-Arg-Arg-Arg-Cys

CysArg₁₃Cys:
                                                                    (SEQ ID NO. 7)
Cys-Arg-Arg-Arg-Arg-Arg-Arg-Arg-Arg-Arg-Arg-Arg-Arg-Cys

CysArg₁₄Cys:
                                                                    (SEQ ID NO. 8)
Cys-Arg-Arg-Arg-Arg-Arg-Arg-Arg-Arg-Arg-Arg-Arg-Arg-Arg-Cys

CysArg₁₅Cys:
                                                                    (SEQ ID NO. 9)
Cys-Arg-Arg-Arg-Arg-Arg-Arg-Arg-Arg-Arg-Arg-Arg-Arg-Arg-Arg-Cys

CysArg₁₆Cys:
                                                                    (SEQ ID NO. 10)
Cys-Arg-Arg-Arg-Arg-Arg-Arg-Arg-Arg-Arg-Arg-Arg-Arg-Arg-Arg-Arg-Cys

CysArg₁₇Cys:
                                                                    (SEQ ID NO. 11)
Cys-Arg-Arg-Arg-Arg-Arg-Arg-Arg-Arg-Arg-Arg-Arg-Arg-Arg-Arg-Arg-Arg-Cys

CysArg₁₈Cys:
                                                                    (SEQ ID NO. 12)
Cys-Arg-Arg-Arg-Arg-Arg-Arg-Arg-Arg-Arg-Arg-Arg-Arg-Arg-Arg-Arg-Arg-Arg-Cys

CysArg₁₉Cys:
                                                                    (SEQ ID NO. 13)
Cys-Arg-Arg-Arg-Arg-Arg-Arg-Arg-Arg-Arg-Arg-Arg-Arg-Arg-Arg-Arg-Arg-Arg-Arg-Cys

CysArg₂₀Cys:
                                                                    (SEQ ID NO. 14)
Cys-Arg-Arg-Arg-Arg-Arg-Arg-Arg-Arg-Arg-Arg-Arg-Arg-Arg-Arg-Arg-Arg-Arg-Arg-Arg Cys
```

This embodiment may apply to situations, wherein the cationic or polycationic peptide or protein of the polymeric carrier, e.g. when defined according to empirical formula $(Arg)_l;(Lys)_m;(His)_n;(Orn)_o;(Xaa)_x$ (formula (I)) as shown above, has been modified with at least two cysteines as —SH moieties in the above meaning such that the cationic or polycationic peptide of the inventive polymeric carrier cargo complex as cationic component carries at least two (terminal) cysteines, which are capable to form a disulfide bond with other components of the polymeric carrier.

According to a second alternative, at least one cationic (or polycationic) component of the polymeric carrier may be selected from e.g. any (non-peptidic) cationic or polycationic polymer suitable in this context, provided that this (non-peptidic) cationic or polycationic polymer exhibits or is modified to exhibit at least one —SH-moiety, which provide for a disulfide bond linking the cationic or polycationic polymer with another component of the polymeric carrier as defined herein. Thus, likewise as defined herein, the polymeric carrier may comprise the same or different cationic or polycationic polymers.

In the specific case that the cationic component of the polymeric carrier comprises a (non-peptidic) cationic or polycationic polymer the cationic properties of the (non-peptidic) cationic or polycationic polymer may be determined upon its content of cationic charges when compared to the overall charges of the components of the cationic polymer. Preferably, the content of cationic charges in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a cationic or polycationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) cationic or polycationic polymer typically exhibits at least one —SH-moiety, which is capable to form a disulfide linkage upon condensation with either other cationic components or other components of the polymeric carrier as defined herein.

In the above context, the (non-peptidic) cationic component of the polymeric carrier may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

In the context of the polymeric carrier, the cationic components, which form basis for the polymeric carrier by disulfide-crosslinkage, may be the same or different from each other. It is also particularly preferred that the polymeric carrier of the present invention comprises mixtures of cationic peptides, proteins or polymers and optionally further components as defined herein, which are crosslinked by disulfide bonds as described herein.

In this context, the inventive polymeric carrier cargo complex due to its variable polymeric carrier advantageously allows to combine desired properties of different (short) cationic or polycationic peptides, proteins or polymers or other components. The polymeric carrier, e.g., allows to efficiently compact nucleic acids for the purpose of efficient transfection of nucleic acids, for adjuvant therapy, for the purposes of gene therapy, for gene knock-down or others strategies without loss of activity, particularly exhibiting an efficient transfection of a nucleic acid into different cell lines in vitro but particularly transfection in vivo. The polymeric carrier and thus the inventive polymeric carrier cargo complex is furthermore not toxic to cells, provides for efficient release of its nucleic acid cargo, is stable during lyophilization and is applicable as immunostimulating agent or adjuvant. Preferably, the polymer carrier cargo complex may induce the anti-viral cytokine IFN-alpha.

In particular, the polymeric carrier formed by disulfide-linked cationic components allows considerably to vary its peptide or polymeric content and thus to modulate its biophysical/biochemical properties, particularly the cationic properties of the polymeric carrier, quite easily and fast, e.g. by incorporating as cationic components the same or different cationic peptide(s) or polymer(s) and optionally adding other components into the polymeric carrier. Even though consisting of quite small non-toxic monomer units the polymeric carrier forms a long cationic binding sequence providing a strong condensation of the nucleic acid cargo and complex stability. Under the reducing conditions of the cytosole (e.g. cytosolic GSH), the complex is rapidly degraded into its (cationic) components, which are further degraded (e.g. oligopeptides). This supports deliberation of the nucleic acid cargo in the cytosol. Due to degradation into small oligopeptides or polymers in the cytosol, no toxicity is observed as known for high-molecular oligopeptides or polymers, e.g. from high-molecular polyarginine.

Accordingly, the polymeric carrier of the inventive polymeric carrier cargo complex may comprise different (short) cationic or polycationic peptides, proteins or polymers selected from cationic or polycationic peptides, proteins or (non-peptidic) polymers as defined above, optionally together with further components as defined herein.

Additionally, the polymeric carrier of the inventive polymeric carrier cargo complex as defined above, more preferably at least one of the different (short) cationic or polycationic peptides or (non-peptidic) polymers forming basis for the polymeric carrier via disulfide-crosslinking, may be, preferably prior to the disulfide-crosslinking, be modified with at least one further component. Alternatively, the polymeric carrier as such may be modified with at least one further component. It may also optionally comprise at least one further component, which typically forms the polymeric carrier disulfide together with the other the (short) cationic or polycationic peptides as defined above via disulfide crosslinking.

To allow modification of a cationic or polycationic peptide or a (non-peptidic) polymer as defined above, each of the components of the polymeric carrier may (preferably already prior to disulfide-crosslinking) also contain at least one further functional moiety, which allows attaching such further components as defined herein. Such functional moieties may be selected from functionalities which allow the attachment of further components, e.g. functionalities as defined herein, e.g. by amide formation (e.g. carboxylic acids, sulphonic acids, amines, etc.), by Michael addition (e.g maleinimide moieties, $\alpha,\beta$ unsaturated carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

According to a particularly preferred embodiment, the further component, which may be contained in the polymeric carrier or which may be used to modify the different (short) cationic or polycationic peptides or (non-peptidic) polymers forming basis for the polymeric carrier of the inventive polymeric carrier cargo complex is an amino acid component (AA), which may e.g. modify the biophysical/biochemical properties of the polymeric carrier as defined herein. According to the present invention, the amino acid component (AA) comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the afore mentioned values. In this context the amino acids of amino acid component (AA) can be chosen independently from each other. For example if in the polymeric carrier two or more (AA) components are present they can be the same or can be different from each other.

The amino acid component (AA) may contain or may be flanked (e.g. terminally) by a —SH containing moiety, which allows introducing this component (AA) via a disulfide bond into the polymeric carrier as defined herein. In the specific case that the —SH containing moiety represents a cysteine, the amino acid component (AA) may also be read as -Cys-(AA)-Cys- wherein Cys represents Cysteine and provides for the necessary —SH-moiety for a disulfide bond. The —SH containing moiety may be also introduced into amino acid component (AA) using any of modifications or reactions as shown above for the cationic component or any of its components.

Furthermore, the amino acid component (AA) may be provided with two —SH-moieties (or even more), e.g. in a form represented by formula HS-(AA)-SH to allow binding to two functionalities via disulfide bonds, e.g. if the amino acid component (AA) is used as a linker between two further components (e.g. as a linker between two cationic polymers). In this case, one —SH moiety is preferably protected in a first step using a protecting group as known in the art, leading to an amino acid component (AA) of formula HS-(AA)-S-protecting group. Then, the amino acid component (AA) may be bound to a further component of the polymeric carrier, to form a first disulfide bond via the non-protected —SH moiety. The protected —SH-moiety is then typically deprotected and bound to a further free —SH-moiety of a further component of the polymeric carrier to form a second disulfide bond.

Alternatively, the amino acid component (AA) may be provided with other functionalities as already described above for the other components of the polymeric carrier, which allow binding of the amino acid component (AA) to any of components of the polymeric carrier.

Thus, according to the present invention, the amino acid component (AA) may be bound to further components of the polymeric carrier with or without using a disulfide linkage. Binding without using a disulfide linkage may be accomplished by any of the reactions described above, preferably by binding the amino acid component (AA) to the other component of the polymeric carrier using an amid-chemistry as defined herein. If desired or necessary, the other terminus of the amino acid component (AA), e.g. the N- or C-terminus, may be used to couple another component, e.g. a ligand L. For this purpose, the other terminus of the amino acid component (AA) preferably comprises or is modified to comprise a further functionality, e.g. an alkyn-species (see above), which may be used to add the other component via e.g. click-chemistry. If the ligand is bound via an acid-labile bond, the bond is preferably cleaved off in the endosome and the polymeric carrier presents amino acid component (AA) at its surface.

The amino acid component (AA) may occur as a further component of the polymeric carrier as defined above, e.g. as a linker between cationic components e.g. as a linker between one cationic peptide and a further cationic peptide, as a linker between one cationic polymer and a further cationic polymer, as a linker between one cationic peptide and a cationic polymer, all preferably as defined herein, or as an additional component of the polymeric carrier, e.g. by binding the amino acid component (AA) to the polymeric carrier or a component thereof, e.g. via side chains, SH-moieties or via further moieties as defined herein, wherein the amino acid component (AA) is preferably accordingly modified.

According to a further and particularly preferred alternative, the amino acid component (AA), may be used to modify the polymeric carrier, particularly the content of cationic components in the polymeric carrier as defined above.

In this context it is preferable, that the content of cationic components in the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 30% to 100%, more preferably in the range of about 50% to 100%, even preferably in the range of about 70% to 100%, e.g. 70, 80, 90 or 100%, or in a range formed by any two of the afore mentioned values, provided, that the content of all components in the polymeric carrier is 100%.

In the context of the present invention, the amino acid component (AA) may be selected from the following alternatives.

According to a first alternative, the amino acid component (AA) may be an aromatic amino acid component (AA). The incorporation of aromatic amino acids or sequences as amino aromatic acid component (AA) into the polymeric carrier of the present invention enables a different (second) binding of the polymeric carrier to the nucleic acid due to interactions of the aromatic amino acids with the bases of the nucleic acid cargo in contrast to the binding thereof by cationic charged sequences of the polymeric carrier molecule to the phosphate backbone. This interaction may occur e.g. by intercalations or by minor or major groove binding. This kind of interaction is not prone to decompaction by anionic complexing partners (e.g. Heparin, Hyaluronic acids) which are found mainly in the extracellular matrix in vivo and is also less susceptible to salt effects.

For this purpose, the amino acids in the aromatic amino acid component (AA) may be selected from either the same or different aromatic amino acids e.g. selected from Trp, Tyr, or Phe. Alternatively, the amino acids (or the entire aromatic amino acid component (AA)) may be selected from following peptide combinations Trp-Tyr, Tyr-Trp, Trp-Trp, Tyr-Tyr, Trp-Tyr-Trp, Tyr-Trp-Tyr, Trp-Trp-Trp, Tyr-Tyr-Tyr, Trp-Tyr-Trp-Tyr, Tyr-Trp-Tyr-Trp, Trp-Trp-Trp-Trp, Phe-Tyr, Tyr-Phe, Phe-Phe, Phe-Tyr-Phe, Tyr-Phe-Tyr, Phe-Phe-Phe, Phe-Tyr-Phe-Tyr, Tyr-Phe-Tyr-Phe, Phe-Phe-Phe-Phe, Phe-Trp, Trp-Phe, Phe-Phe, Phe-Trp-Phe, Trp-Phe-Trp, Phe-Trp-Phe-Trp, Trp-Phe-Trp-Phe, or Tyr-Tyr-Tyr-Tyr, etc. (SEQ ID NOs: 15-42). Such peptide combinations may be repeated e.g. 1, 2, 3, 4, 5, 6, 7, 8, 9, 10, 12, 13, 14, 15 or even more times. These peptide combinations may als be combined with each other as suitable.

Additionally, the aromatic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the aromatic amino acid component (AA) may be selected from e.g. peptide combinations Cys-Tyr-Cys, Cys-Trp-Cys, Cys-Trp-Tyr-Cys, Cys-Tyr-Trp-Cys, Cys-Trp-Trp-Cys, Cys-Tyr-Tyr-Cys, Cys-Trp-Tyr-Trp-Cys, Cys-Tyr-Trp-Tyr-Cys, Cys-Trp-Trp-Trp-Cys, Cys-Tyr-Tyr-Tyr-Cys, Cys-Trp-Tyr-Trp-Tyr-Cys, Cys-Tyr-Trp-Tyr-Trp-Cys, Cys-Trp-Trp-Trp-Trp-Cys, Cys-Tyr-Tyr-Tyr-Tyr-Cys, Cys-Phe-Cys, Cys-Phe-Tyr-Cys, Cys-Tyr-Phe-Cys, Cys-Phe-Phe-Cys, Cys-Tyr-Tyr-Cys, Cys-Phe-Tyr-Phe-Cys, Cys-Tyr-Phe-Tyr-Cys, Cys-Phe-Phe-Phe-Cys, Cys-Tyr-Tyr-Tyr-Cys, Cys-Phe-Tyr-Phe-Tyr-Cys-Tyr-Phe-Tyr-Phe-Cys, or Cys-Phe-Phe-Phe-Phe-Cys, Cys-Phe-Trp-Cys, Cys-Trp-Phe-Cys, Cys-Phe-Phe-Cys, Cys-Phe-Trp-Phe-Cys, Cys-Trp-Phe-Trp-Cys, Cys-Phe-Trp-Phe-Trp-Cys, Cys-Trp-Phe-Trp-Phe-Cys, etc. (SEQ ID NOs: 43-75). Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 12, 13, 14, 15 or even more times. These peptide combinations may als be combined with each other as suitable.

Additionally, the aromatic amino acid component (AA) may contain or represent at least one proline, which may serve as a structure breaker of longer sequences of Trp, Tyr and Phe in the aromatic amino acid component (AA), preferably two, three or more prolines.

According to a second alternative, the amino acid component (AA) may be a hydrophilic (and preferably non charged polar) amino acid component (AA). The incorporation of hydrophilic (and preferably non charged polar) amino acids or sequences as amino hydrophilic (and preferably non charged polar) acid component (AA) into the polymeric carrier of the present invention enables a more flexible binding to the nucleic acid cargo. This leads to a more effective compaction of the nucleic acid cargo and hence to a better protection against nucleases and unwanted decompaction. It also allows provision of a (long) polymeric carrier which exhibits a reduced cationic charge over the entire carrier and in this context to better adjusted binding properties, if desired or necessary.

For this purpose, the amino acids in the hydrophilic (and preferably non charged polar) amino acid component (AA) may be selected from either the same or different hydrophilic (and preferably non charged polar) amino acids e.g. selected from Thr, Ser, Asn or Gln. Alternatively, the amino acids (or the entire hydrophilic (and preferably non charged polar) amino acid component (AA)) may be selected from following peptide combinations Ser-Thr, Thr-Ser, Ser-Ser, Thr-Thr, Ser-Thr-Ser, Thr-Ser-Thr, Ser-Ser-Ser, Thr-Thr-Thr, Ser-Thr-Ser-Thr, Thr-Ser-Thr-Ser, Ser-Ser-Ser-Ser, Thr-Thr-Thr-Thr, Gln-Asn, Asn-Gln, Gln-Gln, Asn-Asn, Gln-Asn-Gln, Asn-Gln-Asn, Gln-Gln-Gln, Asn-Asn-Asn, Gln-Asn-Gln-Asn, Asn-Gln-Asn-Gln, Gln-Gln-Gln-Gln, Asn-Asn-Asn-Asn, Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn, Asn-Ser-Asn-Ser, Ser-Ser-Ser-Ser, or Asn-Asn-Asn-Asn, etc. (SEQ ID NOs: 76-111) Such peptide combinations may be repeated e.g. 1, 2, 3, 4, 5, 6, 7, 8, 9, 10, 12, 13, 14, 15 or even more times. These peptide combinations may als be combined with each other as suitable.

Additionally, the hydrophilic (and preferably non-charged polar) amino acid component (AA) may contain or may be flanked by a —SH containing moiety, which allows introducing this component via a disulfide bond as a further part of generic formula (I) above, e.g. as a linker. Such a —SH containing moiety may be any moiety as defined herein suitable to couple one component as defined herein to a further component as defined herein. As an example, such a —SH containing moiety may be a cysteine. Then, e.g. the hydrophilic (and preferably non-charged polar) amino acid component (AA) may be selected from e.g. peptide combinations Cys-Thr-Cys, Cys-Ser-Cys, Cys-Ser-Thr-Cys, Cys-Thr-Ser-Cys, Cys-Ser-Ser-Cys, Cys-Thr-Thr-Cys, Cys-Ser-Thr-Ser-Cys, Cys-Thr-Ser-Thr-Cys, Cys-Ser-Ser-Ser-Cys, Cys-Thr-Thr-Thr-Cys, Cys-Ser-Thr-Ser-Thr-Cys, Cys-Thr-Ser-Thr-Ser-Cys, Cys-Ser-Ser-Ser-Ser-Cys, Cys-Thr-Thr-Thr-Thr-Cys, Cys-Asn-Cys, Cys-Gln-Cys, Cys-Gln-Asn-Cys, Cys-Asn-Gln-Cys, Cys-Gln-Gln-Cys, Cys-Asn-Asn-Cys, Cys-Gln-Asn-Gln-Cys, Cys-Asn-Gln-Asn-Cys, Cys-Gln-Gln-Gln-Cys, Cys-Asn-Asn-Asn-Cys, Cys-Gln-Asn-Gln-Asn-Cys, Cys-Asn-Gln-Asn-Gln-Cys, Cys-Asn-Asn-Asn-Asn-Cys, Cys-Asn-Cys, Cys-Ser-Cys, Cys-Ser-Asn-Cys, Cys-Asn-Ser-Cys, Cys-Ser-Ser-Cys, Cys-Asn-Asn-Cys, Cys-Ser-Asn-Ser-Cys, Cys-Asn-Ser-Asn-Cys, Cys-Ser-Ser-Ser-Cys, Cys-Asn-Asn-Asn-Cys, Cys-Ser-Asn-Ser-Asn-Cys, Cys-Asn-Ser-Asn-Ser-Cys, Cys-Ser-Ser-Ser-Ser-Cys, or Cys-Asn-Asn-Asn-Asn-Cys, etc. (SEQ ID NOs: 112-153). Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the hydrophilic (and preferably non-charged polar) amino acid component (AA) may contain at least one proline, which may serve as a structure breaker of longer sequences of Ser, Thr and Asn in the hydrophilic (and preferably non charged polar) amino acid component (AA), preferably two, three or more prolines.

According to a third alternative, the amino acid component (AA) may be a lipohilic amino acid component (AA). The incorporation of lipohilic amino acids or sequences as amino lipohilic acid component (AA) into the polymeric carrier of the present invention enables a stronger compaction of the nucleic acid cargo and/or the polymeric carrier and its nucleic acid cargo when forming a complex. This is particularly due to interactions of one or more polymer strands of the polymeric carrier, particularly of lipophilic sections of lipohilic amino acid component (AA) and the nucleic acid cargo. This interaction will preferably add an additional stability to the complex between the polymeric carrier and its nucleic acid cargo. This stabilization may somehow be compared to a sort of non covalent crosslinking between different polymer-strands. Especially in aqueous environment this interaction is typically strong and provides a significant effect.

For this purpose, the amino acids in the lipophilic amino acid component (AA) may be selected from either the same or different lipophilic amino acids e.g. selected from Leu, Val, Ile, Ala, Met. Alternatively, the amino acid AA (or the entire lipophilic amino acid component (AA)) may be selected from following peptide combinations Leu-Val, Val-Leu, Leu-Leu, Val-Val, Leu-Val-Leu, Val-Leu-Val, Leu-Leu-Leu, Val-Val-Val, Leu-Val-Leu-Val, Val-Leu-Val-Leu, Leu-Leu-Leu-Leu, Val-Val-Val-Val, Ile-Ala, Ala-Ile, Ile-Ile, Ala-Ala, Ile-Ala-Ile, Ala-Ile-Ala, Ile-Ile-Ile, Ala-Ala-Ala, Ile-Ala-Ile-Ala, Ala-Ile-Ala-Ile, Ile-Ile-Ile-Ile, Ala-Ala-Ala-Ala, Met-Ala, Ala-Met, Met-Met, Ala-Ala, Met-Ala-Met, Ala-Met-Ala, Met-Met-Met, Ala-Ala-Ala, Met-Ala-Met-Ala, Ala-Met-Ala-Met, or Met-Met-Met-Met etc. (SEQ ID NOs: 154-188) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain or may be flanked by a —SH containing moiety, which allows introducing this component via a disulfide bond as a further part of the polymeric carrier above, e.g. as a linker. Such a —SH containing moiety may be any moiety as defined herein suitable to couple one component as defined herein to a further component as defined herein. As an example, such a —SH containing moiety may be a cysteine. Then, e.g. the lipophilic amino acid component (AA) may be selected from e.g. peptide combinations Cys-Val-Cys, Cys-Leu-Cys, Cys-Leu-Val-Cys, Cys-Val-Leu-Cys, Cys-Leu-Leu-Cys, Cys-Val-Val-Cys, Cys-Leu-Val-Leu-Cys, Cys-Val-Leu-Val-Cys, Cys-Leu-Leu-Leu-Cys, Cys-Val-Val-Val-Cys, Cys-Leu-Val-Leu-Val-Cys, Cys-Val-Leu-Val-Leu-Cys, Cys-Leu-Leu-Leu-Leu-Cys, Cys-Val-Val-Val-Val-Cys, Cys-Ala-Cys, Cys-Ile-Cys, Cys-Ile-Ala-Cys, Cys-Ala-Ile-Cys, Cys-Ile-Ile-Cys, Cys-Ala-Ala-Cys, Cys-Ile-Ala-Ile-Cys, Cys-Ala-Ile-Ala-Cys, Cys-Ile-Ile-Ile-Ile-Cys, or Cys-Ala-Ala-Ala-Ala-Cys, Cys-Met-Ala-Met-Cys, Cys-Ala-Met-Ala-Cys, Cys-Met-Met-Cys, Cys-Met-Met-Cys, Cys-Ala-Ala-Cys, Cys-Met-Ala-Met-Cys, Cys-Ala-Met-Ala-Cys, Cys-Met-Met-Met-Cys, Cys-Ala-Ala-Ala-Cys, Cys-Met-Ala-Met-Ala-Cys, Cys-Ala-Met-Ala-Met-Cys, Cys-Met-Met-Met-Met-Cys, or Cys-Ala-Ala-Ala-Ala-Cys, etc. (SEQ ID NOs: 189-229). Each Cys above may also be replaced by any modified peptide or chemical compound carrying a free —SH moiety as defined herein. Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain at least one proline, which may serve as a structure breaker of longer sequences of Leu, Val, Ile, Ala and Met in the lipophilic amino acid component (AA), preferably two, three or more prolines.

Finally, according to a fourth alternative, the amino acid component (AA) may be a weak basic amino acid component (AA). The incorporation of weak basic amino acids or sequences as weak basic amino acid component (AA) into the polymeric carrier of the present invention may serve as a proton sponge and facilitates endosomal escape (also called endosomal release) (proton sponge effect). Incorporation of such a weak basic amino acid component (AA) preferably enhances transfection efficiency.

For this purpose, the amino acids in the weak basic amino acid component (AA) may be selected from either the same or different weak amino acids e.g. selected from histidine or aspartate (aspartic acid). Alternatively, the weak basic amino acids (or the entire weak basic amino acid component (AA)) may be selected from following peptide combinations Asp-His, His-Asp, Asp-Asp, His-His, Asp-His-Asp, His-Asp-His, Asp-Asp-Asp, His-His-His, Asp-His-Asp-His, His-Asp-His-Asp, Asp-Asp-Asp-Asp, or His-His-His-His, etc. (SEQ ID NOs: 230-241) Such peptide combinations may be repeated e.g. 1, 2, 3, 4, 5, 6, 7, 8, 9, 10, 12, 13, 14, 15 or even more times. These peptide combinations may als be combined with each other as suitable.

Additionally, the weak basic amino acid component (AA) may contain or may be flanked by a —SH containing moiety, which allows introducing this component via a disulfide bond as a further part of generic formula (I) above, e.g. as a linker. Such a —SH containing moiety may be any moiety as defined herein suitable to couple one component as defined herein to a further component as defined herein. As an example, such a —SH containing moiety may be a cysteine. Then, e.g. the weak basic amino acid component (AA) may be selected from e.g. peptide combinations Cys-His-Cys, Cys-Asp-Cys, Cys-Asp-His-Cys, Cys-His-Asp-Cys, Cys-Asp-Asp-Cys, Cys-His-His-Cys, Cys-Asp-His-Asp-Cys, Cys-His-Asp-His-Cys, Cys-Asp-Asp-Asp-Cys, Cys-His-His-His-Cys, Cys-Asp-His-Asp-His-Cys, Cys-His-Asp-His-Asp-Cys, Cys-Asp-Asp-Asp-Asp-Cys, or Cys-His-His-His-His-Cys, etc. (SEQ ID NOs: 242-255). Each Cys above may also be replaced by any modified peptide or chemical compound carrying a free —SH-moiety as defined herein. Such peptide combinations may be repeated e.g. 1, 2, 3, 4, 5, 7, 8, 9, 10, 12, 13, 14, 15 or even more times. These peptide combinations may als be combined with each other as suitable.

Additionally, the weak basic amino acid component (AA) may contain at least one proline, which may serve as a structure breaker of longer sequences of histidine or aspartate (aspartic acid) in the weak basic amino acid component (AA), preferably two, three or more prolines.

According to a fifth alternative, the amino acid component (AA) may be a signal peptide or signal sequence, a localization signal or sequence, a nuclear localization signal or sequence (NLS), an antibody, a cell penetrating peptide, (e.g. TAT), etc. Preferably such an amino acid component (AA) is bound to the polymeric carrier or to another component of the polymeric carrier via a (reversible) disulfide bond. In this context the signal peptide or signal sequence, a localization signal or sequence, a nuclear localization signal or sequence (NLS), an antibody, a cell penetrating peptide, (e.g. TAT), etc.; additionally comprises at least one —SH-moiety. In this context a signal peptide, a localization signal or sequence or a nuclear localization signal or sequence (NLS), may be used to direct the inventive polymeric carrier cargo complex to specific target cells (e.g. hepatocytes or antigen-presenting cells) and preferably allows a translocalization of the polymeric carrier to a specific target, e.g. into the cell, into the nucleus, into the endosomal compartment, sequences for the mitochondrial matrix, localisation sequences for the plasma membrane, localisation sequences for the Golgi apparatus, the nucleus, the cytoplasm and the cytosceleton, etc. Such signal peptide, a localization signal or sequence or a nuclear localization signal may be used for the transport of any of the herein defined nucleic acids, preferably an RNA or a DNA, more preferably an shRNA or a pDNA, e.g. into the nucleus. Without being limited thereto, such a signal peptide, a localization signal or sequence or a nuclear localization signal may comprise, e.g., localisation sequences for the endoplasmic reticulum. Particular localization signals or sequences or a nuclear localization signals may include e.g. KDEL (SEQ ID NO: 256), DDEL (SEQ ID NO: 257), DEEL (SEQ ID NO: 258), QEDL (SEQ ID NO: 259), RDEL (SEQ ID NO: 260), and GQNLSTSN (SEQ ID NO: 261), nuclear localisation sequences, including PKKKRKV (SEQ ID NO: 262), PQK-KIKS (SEQ ID NO: 263), QPKKP (SEQ ID NO: 264), RKKR (SEQ ID NO: 265), RKKRRQRRRAHQ (SEQ ID NO: 266), RQARRNRRRRWRERQR (SEQ ID NO: 267), MPLTRRRPAASQALAPPTP (SEQ ID NO: 268), GAALTILV (SEQ ID NO: 269), and GAALTLLG (SEQ ID NO: 270), localisation sequences for the endosomal compartment, including MDDQRDLISNNEQLP (SEQ ID NO: 271), localisation sequences for the mitochondrial matrix, including MLFNLRXXLNNAAFRHGHNFMVRNFRCGQPLX (SEQ ID NO: 272), localisation sequences for the plasma membrane: GCVCSSNP (SEQ ID NO: 273), GQTVTTPL (SEQ ID NO: 274), GQELSQHE (SEQ ID NO: 275), GNSPSYNP (SEQ ID NO: 276), GVSGSKGQ (SEQ ID NO: 277), GQTITTPL (SEQ ID NO: 278), GQTLTTPL (SEQ ID NO: 279), GQIFSRSA (SEQ ID NO: 280), GQIHGLSP (SEQ ID NO: 281), GARASVLS (SEQ ID NO: 282), and GCTLSAEE (SEQ ID NO: 283), localisation sequences for the endoplasmic reticulum and the nucleus, including GAQVSSQK (SEQ ID NO: 284), and GAQLSRNT (SEQ ID NO: 285), localisation sequences for the Golgi apparatus, the nucleus, the cytoplasm and the cytosceleton, including GNAAAAKK (SEQ ID NO: 286), localisation sequences for the cytoplasm and cytosceleton, including GNEASYPL (SEQ ID NO: 287), localisation sequences for the plasma membrane and cytoskeleton, including GSSKSKPK (SEQ ID NO: 288), etc. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulins as defined herein, signal sequences of the invariant chain of immunoglobulins or antibodies as defined herein, signal sequences of Lamp1, Tapasin, Erp57, Calreticulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention. Such an additional component may be bound e.g. to a cationic polymer or to any other component of the polymeric carrier as defined herein. Preferably this signal peptide, localization signal or sequence or nuclear localization signal or sequence (NLS), is bound to the polymeric carrier or to another component of the polymeric carrier via a (reversible) disulfide bond. For this purpose the (AA) component additionally comprises at least one —SH moiety as defined herein.

The binding to any of components of the polymeric carrier may also be accomplished using an acid-labile bond, preferably via a side chain of any of components of the polymeric carrier, which allows to detach or release the additional component at lower pH-values, e.g. at physiological pH-values as defined herein.

Additionally, according to another alternative, the amino acid component (AA) may be a functional peptide or protein, which may modulate the functionality of the polymeric carrier accordingly. Such functional peptides or proteins as the amino acid component (AA) preferably comprise any peptides or proteins as defined herein, e.g. as defined below as therapeutically active proteins. According to one alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the polymeric carrier (in complex with a nucleic acid) from the endosome by insertion into the lipid layer of the liposome. These cell penetrating peptides (CPPs) or cationic peptides for transportation, may include, without being limited thereto protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc. Such an amino acid component (AA) may also be bound to any component of the polymeric carrier as defined herein. Preferably it is bound to the polymeric carrier or to another component of the polymeric carrier via a (reversible) disulfide bond. For the above purpose, the amino acid component (AA) preferably comprises at least one —SH moiety as defined herein. The binding to any of components of the polymeric carrier may also be accomplished using an SH-moiety or an acid-labile bond, preferably via a side chain of any of components of the polymeric carrier which allows to detach or release the additional component at lower pH-values, e.g. at physiological pH-values as defined herein.

According to a last alternative, the amino acid component (AA) may consist of any peptide or protein which can execute any favorable function in the cell. Particularly preferred are peptides or proteins selected from therapeutically active proteins or peptides, from antigens, e.g. tumour antigens, pathogenic antigens (animal antigens, viral antigens, protozoal antigens, bacterial antigens, allergic antigens), autoimmune antigens, or further antigens, from allergens, from antibodies, from immunostimulatory proteins or peptides, from antigen-specific T-cell receptors, or from any other protein or peptide suitable for a specific (therapeutic) application as defined below for coding nucleic acids. Particularly preferred are peptide epitopes from antigens as defined herein.

The polymeric carrier may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

According to another aspect, the polymeric carrier of the inventive polymeric carrier cargo complex or single components thereof, e.g. of the above mentioned cationic or polycationic peptides, proteins or polymers or further components, e.g. (AA), may be further modified with a ligand, preferably a carbohydrate, more preferably a sugar, even more preferably mannose. Preferably this ligand is bound to the polymeric carrier or to a component of the polymeric carrier via a (reversible) disulfide bond or via Michael addition. In the case that the ligand is bound by a disulfide bond the ligand additionally comprises at least one —SH-moiety. These ligands may be used to direct the inventive polymeric carrier cargo complex to specific target cells (e.g. hepatocytes or antigen-presenting cells). In this context mannose is particular preferred as ligand in the case that dendritic cells are the target especially for vaccination or adjuvant purposes.

According to a further aspect of the invention, the inventive polymeric carrier cargo complex may comprise (AA) components as defined above which do not comprise —SH moieties. These (AA) components can be added before or during the complexation reaction of the at least one nucleic acid molecule. Thereby, the (AA) component(s) is/are (non-covalently) incorporated into the inventive polymeric carrier cargo complex without inclusion of the (AA) component(s) in the polymeric carrier itself by (covalent) polymerization.

According to one specific embodiment, the entire inventive polymeric carrier cargo complex may be formed by a polymerization condensation (of at least one) of the above mentioned cationic or polycationic peptides, proteins or polymers or further components, e.g. (AA), via their —SH-moieties in a first step and complexing the nucleic acid to such a polymeric carrier in a second step. The polymeric carrier may thus contain a number of at least one or even more of the same or different of the above defined cationic or polycationic peptides, proteins or polymers or further components, e.g. (AA), the number preferably determined by the above range.

According to one alternative specific embodiment, the inventive polymeric carrier cargo complex is formed by carrying out the polymerization condensation of at least one of the above mentioned cationic or polycationic peptides, proteins or polymers or further components, e.g. (AA), via their —SH-moieties simultaneously to complexing the nucleic acid cargo to the (in situ prepared) polymeric carrier. Likewise, the polymeric carrier may thus also here contain a number of at least one or even more of the same or different of the above defined cationic or polycationic peptides, proteins or polymers or further components, e.g. (AA), the number preferably determined by the above range.

The inventive polymeric carrier cargo complex additionally comprises as a cargo at least one nucleic acid (molecule). In the context of the present invention, such a nucleic acid molecule may be any suitable nucleic acid, selected e.g. from any (single-stranded or double-stranded) DNA, preferably, without being limited thereto, e.g. genomic DNA, single-stranded DNA molecules, double-stranded DNA molecules, coding DNA, DNA primers, DNA probes, immunostimulatory DNA, a (short) DNA oligonucleotide ((short) oligodesoxyribonucleotides), or may be selected e.g. from any PNA (peptide nucleic acid) or may be selected e.g. from any (single-stranded or double-stranded) RNA, preferably, without being limited thereto, a (short) RNA oligonucleotide ((short) oligoribonucleotide), a coding RNA, a messenger RNA (mRNA), an immunostimulatory RNA, a small interfering RNA (siRNA), an antisense RNA, a micro RNA, a small nuclear RNA (snRNA), a small-hairpin (sh) RNA or riboswitches, ribozymes or aptamers; etc. The nucleic acid molecule of the inventive polymeric carrier cargo complex may also be a ribosomal RNA (rRNA), a transfer RNA (tRNA), a messenger RNA (mRNA), or a viral RNA (vRNA). Preferably, the nucleic acid molecule of the inventive polymeric carrier cargo complex is an RNA. More preferably, the nucleic acid molecule of the inventive polymeric carrier cargo complex is a (linear) single-stranded RNA, even more preferably an mRNA or an immunostimulatory RNA. In the context of the present invention, an mRNA is typically an RNA, which is composed of several structural elements, e.g. an optional 5'-CAP structure, an optional 5'-UTR region, an upstream positioned ribosomal binding site followed by a coding region, an optional 5'-UTR region, which may be followed by a poly-A tail (and/or a poly-C-tail). An mRNA may occur as a mono-, di-, or even multicistronic RNA, i.e. a RNA which carries the coding sequences of one, two or more proteins or peptides. Such coding sequences in di-, or even multicistronic mRNA may be separated by at least one IRES sequence, e.g. as defined herein.

Furthermore, the nucleic acid of the inventive polymeric carrier cargo complex may be a single- or a double-stranded nucleic acid (molecule) (which may also be regarded as a nucleic acid (molecule) due to non-covalent association of two single-stranded nucleic acid(s) (molecules)) or a partially double-stranded or partially single stranded nucleic acid, which are at least partially self complementary (both of these partially double-stranded or partially single stranded nucleic acid molecules are typically formed by a longer and a shorter single-stranded nucleic acid molecule or by two single stranded nucleic acid molecules, which are about equal in length, wherein one single-stranded nucleic acid molecule is in part complementary to the other single-stranded nucleic acid molecule and both thus form a double-stranded nucleic acid molecule in this region, i.e. a partially double-stranded or partially single stranded nucleic acid (molecule). Preferably, the nucleic acid (molecule) may be a single-stranded nucleic acid molecule. Furthermore, the nucleic acid (molecule) may be a circular or linear nucleic acid molecule, preferably a linear nucleic acid molecule.

According to one alternative, the nucleic acid molecule of the inventive polymeric carrier cargo complex may be a coding nucleic acid, e.g. a DNA or RNA. Such a coding DNA or RNA may be any DNA or RNA as defined herein. Preferably, such a coding DNA or RNA may be a single- or a double-stranded DNA or RNA, more preferably a single-stranded DNA or RNA, and/or a circular or linear DNA or RNA, more preferably a linear DNA or RNA. Even more preferably, the coding DNA or RNA may be a (linear) single-stranded DNA or RNA. Most preferably, the nucleic acid molecule according to the present invention may be a ((linear) single-stranded) messenger RNA (mRNA). Such an mRNA may occur as a mono-, di-, or even multicistronic RNA, i.e. an RNA which carries the coding sequences of one, two or more proteins or peptides. Such coding sequences in di-, or even multicistronic mRNA may be separated by at least one IRES sequence, e.g. as defined herein.

Coding Nucleic Acids:

The nucleic acid molecule of the inventive polymeric carrier cargo complex may encode a protein or a peptide, which may be selected, without being restricted thereto, e.g. from therapeutically active proteins or peptides, including adjuvant proteins, from antigens, e.g. tumour antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, or from any other protein or peptide suitable for a specific (therapeutic) application, wherein the coding nucleic acid may be transported into a cell, a tissue or an organism and the protein may be expressed subsequently in this cell, tissue or organism.

a) Therapeutically Active Proteins

In the context of the present invention, therapeutically active proteins or peptides may be encoded by the nucleic acid molecule of the herein defined inventive polymeric carrier cargo complex. Therapeutically active proteins are defined herein as proteins which have an effect on healing, prevent prophylactically or treat therapeutically a disease, preferably as defined herein, or are proteins of which an individual is in need of. These may be selected from any naturally or synthetically designed occurring recombinant or isolated protein known to a skilled person from the prior art. Without being restricted thereto therapeutically active proteins may comprise proteins, capable of stimulating or inhibiting the signal transduction in the cell, e.g. cytokines, lymphokines, monokines, growth factors, receptors, signal transduction molecules, transcription factors, etc; anticoagulants; antithrombins; antiallergic proteins; apoptotic factors or apoptosis related proteins, therapeutic active enzymes and any protein connected with any acquired disease or any hereditary disease.

A therapeutically active protein, which may be encoded by the nucleic acid molecule of the herein defined inventive polymeric carrier cargo complex, may also be an adjuvant protein. In this context, an adjuvant protein is preferably to be understood as any protein, which is capable to elicit an innate immune response as defined herein. Preferably, such an innate immune response comprises activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. More preferably, the adjuvant protein is selected from human adjuvant proteins or from pathogenic adjuvant proteins, selected from the group consisting of, without being limited thereto, bacterial proteins, protozoan proteins, viral proteins, or fungal proteins, animal proteins, in particular from bacterial adjuvant proteins. In addition, nucleic acids encoding human proteins involved in adjuvant effects (e.g. ligands of pattern recognition receptors, pattern recoginition receptors, proteins of the signal transduction pathways, transcription factors or cytokines) may be used as well.

b) Antigens

The nucleic acid molecule of the herein defined inventive polymeric carrier cargo complex may alternatively encode an antigen. According to the present invention, the term "antigen" refers to a substance which is recognized by the immune system and is capable of triggering an antigen-specific immune response, e.g. by formation of antibodies or antigen-specific T-cells as part of an adaptive immune response. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by CD8+ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. CD4+ T cells bind to a MHC class II molecule and CD8+ T cells to a MHC class I molecule. MHC class I and MHC class II molecules have distinct distributions among cells that reflect the different effector functions of the T cells that recognize them. MHC class I molecules present peptides from pathogens, commonly viruses to CD8+ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. Thereby MHC class I molecules on the surface of cells infected with viruses or other cytosolic pathogens display peptides from these pathogen. The CD8+ T cells that recognize MHC class I:peptide complexes are specialized to kill any cells displaying foreign peptides and so rid the body of cells infected with viruses and other cytosolic pathogens. The main function of CD4+ T cells (CD4+ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

In the context of the present invention, antigens as encoded by the nucleic acid molecule of the herein defined inventive polymeric carrier cargo complex typically comprise any antigen, antigenic epitope or antigenic peptide, falling under the above definition, more preferably protein and peptide antigens, e.g. tumour antigens, allergenic antigens, auto-immune self-antigens, pathogenic antigens, etc. In particular antigens as encoded by the nucleic acid molecule of the herein defined inventive polymeric carrier cargo complex may be antigens generated outside the cell, more typically antigens not derived from the host organism (e.g. a human) itself (i.e. non-self antigens) but rather derived from host cells outside the host organism, e.g. viral antigens, bacterial antigens, fungal antigens, protozoological antigens, animal antigens, allergenic antigens, etc. Allergenic antigens (allergy antigens) are typically antigens, which cause an allergy in a human and may be derived from either a human or other sources. Additionally, antigens as encoded by the nucleic acid molecule of the herein defined inventive polymeric carrier cargo complex may be furthermore antigens generated inside the cell, the tissue or the body. Such antigens include antigens derived from the host organism (e.g. a human) itself, e.g. tumour antigens, self-antigens or auto-antigens, such as auto-immune self-antigens, etc., but also (non-self) antigens as defined herein, which have been originally been derived from host cells outside the host organism, but which are fragmented or degraded inside the body, tissue or cell, e.g. by (protease) degradation, metabolism, etc.

One class of antigens as encoded by the nucleic acid molecule of the herein defined inventive polymeric carrier cargo complex comprises tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies. Particular preferred tumour antigens are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR-2/FLK-1, and WT1. Such tumour antigens preferably may be selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), surviving (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFRI (epidermal growth factor receptor 1) (e.g. EGFRI (epidermal growth factor receptor 1) according to accession number AF288738), MUC1, mucin-1 (e.g. mucin-1 according to accession number NM_002456), SEC61G (e.g. SEC61G according to accession number NM_014302), hTERT (e.g. hTERT accession number NM_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

According to another alternative, one further class of antigens as encoded by the nucleic acid molecule of the herein defined inventive polymeric carrier cargo complex comprises allergenic antigens. Such allergenic antigens may be selected from antigens derived from different sources, e.g. from animals, plants, fungi, bacteria, etc. Allergens in this context include e.g. grasses, pollens, molds, drugs, or numerous environmental triggers, etc. Allergenic antigens typically belong to different classes of compounds, such as nucleic acids and their fragments, proteins or peptides and their fragments, carbohydrates, polysaccharides, sugars, lipids, phospholipids, etc. Of particular interest in the context of the present invention are antigens, which may be encoded by the nucleic acid molecule of the inventive polymeric carrier cargo complex, i.e. protein or peptide antigens and their fragments or epitopes, or nucleic acids and their fragments, particularly nucleic acids and their fragments, encoding such protein or peptide antigens and their fragments or epitopes.

c) Antibodies

According to a further alternative, the nucleic acid molecule of the herein defined inventive polymeric carrier cargo complex may encode an antibody or an antibody fragment. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, the term "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$.

In the context of the present invention, antibodies as encoded by the nucleic acid molecule of the herein defined inventive polymeric carrier cargo complex may preferably comprise full-length antibodies, i.e. antibodies composed of the full heavy and full light chains, as described above. However, derivatives of antibodies such as antibody fragments, variants or adducts may also be encoded by the nucleic acid molecule of the herein defined inventive inventive polymeric carrier cargo complex. Antibody fragments are preferably selected from Fab, Fab', F(ab')$_2$, Fc, Facb, pFc', Fd and Fv fragments of the aforementioned (full-length) antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

In the present context it is preferable that the different chains of the antibody or antibody fragment are encoded by a multicistronic nucleic acid molecule. Alternatively, the different strains of the antibody or antibody fragment are encoded by several monocistronic nucleic acid(s) (sequences).

siRNA:

According to a further alternative, the nucleic acid molecule of the herein defined inventive polymeric carrier cargo complex may be in the form of dsRNA, preferably siRNA. A dsRNA, or a siRNA, is of interest particularly in connection with the phenomenon of RNA interference. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498).

The nucleic acid molecule of the herein inventive polymeric carrier cargo complex may thus be a double-stranded RNA (dsRNA) having a length of from 17 to 29, preferably from 19 to 25, and preferably is at least 90%, more preferably 95% and especially 100% (of the nucleotides of a dsRNA) complementary to a section of the nucleic acid molecule of a (therapeutically relevant) protein or antigen described (as active ingredient) hereinbefore or of any further protein as described herein, either a coding or a non-coding section, preferably a coding section. Such a (section of the) nucleic acid molecule may be termed herein a "target sequence" and may be any nucleic acid molecule as defined herein, preferably a genomic DNA, a cDNA, a RNA, e.g. an mRNA, etc. 90% complementary means that with a length of a dsRNA described herein of, for example, 20 nucleotides, the dsRNA contains not more than 2 nucleotides showing no complementarity with the corresponding section of the target sequence. The sequence of the double-stranded RNA used according to the invention is, however, preferably wholly complementary in its general structure with a section of the target sequence. In this context the nucleic acid molecule of the inventive polymeric carrier cargo complex may be a dsRNA having the general structure 5'-(N$_{17-29}$)-3', preferably having the general structure 5'-(N$_{19-25}$)-3', more preferably having the general structure 5'-(N$_{19-24}$)-3', or yet more preferably having the general structure 5'-(N$_{21-23}$)-3', wherein for each general structure each N is a (preferably different) nucleotide of a section of the target sequence, preferably being selected from a continuous number of 17 to 29 nucleotides of a section of the target sequence, and being present in the general structure 5'-(N$_{17-29}$)-3' in their natural order. In principle, all the sections having a length of from 17 to 29, preferably from 19 to 25, base pairs that occur in the target sequence can serve for preparation of a dsRNA as defined herein. Equally, dsRNAs used as nucleic acid molecule of the inventive polymeric carrier cargo complex can also be directed against nucleotide sequences of a (therapeutically relevant) protein or antigen described (as active ingredient) hereinbefore that do not lie in the coding region, in particular in the 5' non-coding region of the target sequence, for example, therefore, against non-coding regions of the target sequence having a regulatory function. The target sequence of the dsRNA used as nucleic acid molecule of the inventive polymeric carrier cargo complex can therefore lie in the translated and untranslated region of the target sequence and/or in the region of the control elements of a protein or antigen described hereinbefore. The target sequence for a dsRNA used as the nucleic acid molecule of the inventive polymeric carrier cargo complex can also lie in the overlapping region of untranslated and translated sequence; in particular, the target sequence can comprise at least one nucleotide upstream of the start triplet of the coding region, e.g. of a genomic DNA, a cDNA, a RNA, or an mRNA, etc.

Immunostimulatory Nucleic Acids:

a) Immunostimulatory CpG Nucleic Acids:

According to another alternative, the nucleic acid molecule of the herein defined inventive polymeric carrier cargo complex may be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated.

b) Immunostimulatory RNA (isRNA):

Likewise, according to a further alternative, the (immunostimulatory) nucleic acid molecule of the inventive polymeric carrier cargo complex may be in the form of an immunostimulatory RNA (isRNA), which preferably elicits an innate immune response. Such an immunostimulatory RNA may be any (double-stranded or single-stranded) RNA, e.g. a coding RNA, as defined herein. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response, may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl Acad Sci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The immunostimulatory RNA (isRNA) used as the nucleic acid molecule of the herein defined inventive polymeric carrier cargo complex may thus comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell. 22, 561-569), or any other immunostimulatory RNA sequence. Furthermore, (classes of) immunostimulatory RNA molecules, used as the nucleic acid molecule of the inventive polymeric carrier cargo complex may include any other RNA capable of eliciting an innate immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, such immunostimulatory nucleic acid sequences is preferably RNA preferably consisting of or comprising a nucleic acid of formula (II) or (III):

$$G_l X_m G_n, \qquad \text{(formula (II))}$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
  wherein
  when l=1 G is guanosine or an analogue thereof,
  when l>1 at least 50% of the nucleotides are guanosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 G is guanosine or an analogue thereof,
  when n>1 at least 50% of the nucleotides are guanosine or an analogue thereof.

$$C_l X_m C_n, \qquad \text{(formula (III))}$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
  wherein
  when l=1 C is cytosine or an analogue thereof,
  when l>1 at least 50% of the nucleotides are cytosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 C is cytosine or an analogue thereof,
  when n>1 at least 50% of the nucleotides are cytosine or an analogue thereof.

The nucleic acids of formula (II) or (III), which may be used the nucleic acid cargo of the inventive polymeric carrier cargo complex may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of the inventive nucleic acid cargo complex has a maximum length of e.g. 100 nucleotides, m will typically be <=98. The number of nucleotides G in the nucleic acid of formula (II) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_l$ or $G_n$ can be, for example, a GUGU, GGUU, UGUG, UUGG, GUUG, GGGU, GGUG, GUGG, UGGG or GGGG, etc.; when l or n=5 $G_l$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (II) according to the invention is preferably not a uracil. Similarly, the number of nucleotides C in the nucleic acid of formula (III) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_l$ or $C_n$ can be, for example, a CUCU, CCUU, UCUC, UUCC, CUUC, CCCU, CCUC, CUCC, UCCC or CCCC, etc.; when l or n=5 $C_l$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (III) according to the invention is preferably not a uracil. Preferably, for formula (II), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (III).

According to a particularly preferred embodiment, a nucleic acid according to any of formulas (II) or (III) above, which may be used as nucleic acid of the inventive polymeric carrier cargo complex, may be selected from a sequence consisting or comprising any of the following sequences:

GGUUUUUUUUUUUUUUGGG; (SEQ ID NO: 289)

GGGGGUUUUUUUUUGGGGG; (SEQ ID NO: 290)

GGGGGUUUUUUUUUUUUUUUUUUUUUUUUUUGGGGG; (SEQ ID NO: 291)

GUGUGUGUGUUUUUUUUUUUUUUUGUGUGUGUGU; (SEQ ID NO: 292)

GGUUGGUUGGUUUUUUUUUUUUUUUGGUUGGUUGGUU; (SEQ ID NO: 293)

GGGGGGGGGUUUGGGGGGGG; (SEQ ID NO: 294)

GGGGGGGGUUUUGGGGGGGG; (SEQ ID NO: 295)

GGGGGGGUUUUUGGGGGGG; (SEQ ID NO: 296)

GGGGGGUUUUUUGGGGGGG; (SEQ ID NO: 297)

GGGGGGUUUUUUUGGGGGG; (SEQ ID NO: 298)

GGGGGGUUUUUUUUGGGGG; (SEQ ID NO: 299)

GGGGGGUUUUUUUUUGGGG; (SEQ ID NO: 300)

GGGGGGUUUUUUUUUUGGG; (SEQ ID NO: 301)

GGGGGUUUUUUUUUUUUGGG; (SEQ ID NO: 302)

GGGGUUUUUUUUUUUUUGGG; (SEQ ID NO: 303)

GGGGUUUUUUUUUUUUUUGG; (SEQ ID NO: 304)

GGUUUUUUUUUUUUUUUUGG; (SEQ ID NO: 305)

GUUUUUUUUUUUUUUUUUG; (SEQ ID NO: 306)

GGGGGGGGGGUUUGGGGGGGGGG; (SEQ ID NO: 307)

GGGGGGGGGUUUUGGGGGGGGG; (SEQ ID NO: 308)

GGGGGGGGGUUUUUGGGGGGGGG; (SEQ ID NO: 309)

GGGGGGGGGUUUUUUGGGGGGG; (SEQ ID NO: 310)

GGGGGGGGUUUUUUUGGGGGGG; (SEQ ID NO: 311)

GGGGGGGUUUUUUUUGGGGGGG; (SEQ ID NO: 312)

GGGGGGGUUUUUUUUUGGGGGG; (SEQ ID NO: 313)

GGGGGGUUUUUUUUUUGGGGGG; (SEQ ID NO: 314)

GGGGGGUUUUUUUUUUUGGGGG; (SEQ ID NO: 315)

GGGGGUUUUUUUUUUUUGGGGG; (SEQ ID NO: 316)

GGGGGUUUUUUUUUUUUUGGGG; (SEQ ID NO: 317)

GGGUUUUUUUUUUUUUUGGG; (SEQ ID NO: 318)

GGUUUUUUUUUUUUUUUUGG; (SEQ ID NO: 319)

GGGGGGGGGGUUUGGGGGGGGG; (SEQ ID NO: 320)

GGGGGGGGGUUUUGGGGGGGGG; (SEQ ID NO: 321)

GGGGGGGGGUUUUUGGGGGGGGG; (SEQ ID NO: 322)

GGGGGGGGGUUUUUUGGGGGGGGG; (SEQ ID NO: 323)

GGGGGGGGUUUUUUUGGGGGGGG; (SEQ ID NO: 324)

GGGGGGGGUUUUUUUUGGGGGGG; (SEQ ID NO: 325)

GGGGGGGGUUUUUUUUUUGGGGGG; (SEQ ID NO: 326)

GGGGGGGUUUUUUUUUUGGGGG; (SEQ ID NO: 327)

GGGGGGGUUUUUUUUUUUGGGGG; (SEQ ID NO: 328)

GGGGGGUUUUUUUUUUUUGGGGG; (SEQ ID NO: 329)

GGGGGGUUUUUUUUUUUUUGGGG; (SEQ ID NO: 330)

GGGGUUUUUUUUUUUUUUGGGG; (SEQ ID NO: 331)

GGGUUUUUUUUUUUUUUUGGG; (SEQ ID NO: 332)

GUUUUUUUUUUUUUUUUUUUUUUUG; (SEQ ID NO: 333)

GGUUUUUUUUUUUUUUUUUUUUUUUGG; (SEQ ID NO: 334)

GGGUUUUUUUUUUUUUUUUUUUUUUUGGG; (SEQ ID NO: 335)

GGGGUUUUUUUUUUUUUUUUUUUUUUUGGGG; (SEQ ID NO: 336)

GGGGGUUUUUUUUUUUUUUUUUUUUUUUGGGGG; (SEQ ID NO: 337)

GGGGGGUUUUUUUUUUUUUUUUUUUUUUUGGGGGG; (SEQ ID NO: 338)

GGGGGGGUUUUUUUUUUUUUUUUUUUUUUUGGGGGGG; (SEQ ID NO: 339)

GGGGGGGGUUUUUUUUUUUUUUUUUUUUUUUGGGGGGGG; (SEQ ID NO: 340)

GGGGGGGGGUUUUUUUUUUUUUUUUUUUUUUUGGGGGGGGG; (SEQ ID NO: 341)

GGUUUGG; (SEQ ID NO: 342)

GGUUUUGG; (SEQ ID NO: 343)

GGUUUUUGG; (SEQ ID NO: 344)

GGUUUUUUGG; (SEQ ID NO: 345)

GGUUUUUUUGG; (SEQ ID NO: 346)

GGUUUUUUUUGG; (SEQ ID NO: 347)

GGUUUUUUUUUGG; (SEQ ID NO: 348)

GGUUUUUUUUUUGG; (SEQ ID NO: 349)

GGUUUUUUUUUUUGG; (SEQ ID NO: 350)

GGUUUUUUUUUUUUGG; (SEQ ID NO: 351)

GGUUUUUUUUUUUUUGG; (SEQ ID NO: 352)

GGUUUUUUUUUUUUUUGG; (SEQ ID NO: 353)

GGUUUUUUUUUUUUUUUGG; (SEQ ID NO: 354)

GGGUUUGGG; (SEQ ID NO: 355)

GGGUUUUGGG; (SEQ ID NO: 356)

GGGUUUUUGGG; (SEQ ID NO: 357)

GGGUUUUUUGGG; (SEQ ID NO: 358)

GGGUUUUUUUGGG; (SEQ ID NO: 359)

GGGUUUUUUUUGGG; (SEQ ID NO: 360)

GGGUUUUUUUUUGGG; (SEQ ID NO: 361)

GGGUUUUUUUUUUGGG; (SEQ ID NO: 362)

GGGUUUUUUUUUUUGGG; (SEQ ID NO: 363)

GGGUUUUUUUUUUUUGGG; (SEQ ID NO: 364)

GGGUUUUUUUUUUUUUGGG (SEQ ID NO: 365)

GGGUUUUUUUUUUUUGGGUUUUUUUUUUUUUGGGUUUUUUUUUU
UUUUGGG; (SEQ ID NO: 366)

GGGUUUUUUUUUUUUGGGGGUUUUUUUUUUUUUUGGG; (SEQ ID NO: 367)

GGGUUUGGGUUUGGGUUUGGGUUUGGGUUUGGGUUUGGGUUUG
GG; (SEQ ID NO: 368)

GGUUUUUUUUUUUUUUUGGG (short GU-rich, SEQ ID NO: 369)

or

CCCUUUUUUUUUUUUUCCCUUUUUUUUUUUUUUCCCUUUUUUUUU
UUUUUCCC (SEQ ID NO: 370)

CCCUUUCCCUUUCCCUUUCCCUUUCCCUUUCCCUUUCCCUUUC
CC (SEQ ID NO: 371)

CCCUUUUUUUUUUUUUUCCCCCCUUUUUUUUUUUUUUUCCC (SEQ ID NO: 372)

or from a sequence having at least 60%, 70%, 80%, 90%, or even 95% sequence identity with any of these sequences According to a further particularly preferred embodiment, such immunostimulatory nucleic acid sequences particularly isRNA consist of or comprise a nucleic acid of formula (IV) or (V):

$$(N_uG_lX_mG_nN_v)_a,$$ (formula (IV))

wherein:

G is guanosine (guanine), uridine (uracil) or an analogue of guanosine (guanine) or uridine (uracil), preferably guanosine (guanine) or an analogue thereof;

X is guanosine (guanine), uridine (uracil), adenosine (adenine), thymidine (thymine), cytidine (cytosine), or an analogue of these nucleotides (nucleosides), preferably uridine (uracil) or an analogue thereof;

N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
  wherein when l=1, G is guanosine (guanine) or an analogue thereof,
    when l>1, at least 50% of these nucleotides (nucleosides) are guanosine (guanine) or an analogue thereof;

m is an integer and is at least 3;
  wherein when m=3, X is uridine (uracil) or an analogue thereof, and
    when m>3, at least 3 successive uridines (uracils) or analogues of uridine (uracil) occur;

n is an integer from 1 to 40,
  wherein when n=1, G is guanosine (guanine) or an analogue thereof,
    when n>1, at least 50% of these nucleotides (nucleosides) are guanosine (guanine) or an analogue thereof;

u,v may be independently from each other an integer from 0 to 50,
  preferably wherein when u=0, v≥1, or
    when v=0, u≥1;

wherein the nucleic acid molecule of formula (IV) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a, \quad \text{(formula (V))}$$

wherein:

C is cytidine (cytosine), uridine (uracil) or an analogue of cytidine (cytosine) or uridine (uracil), preferably cytidine (cytosine) or an analogue thereof;

X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;

N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
  wherein when l=1, C is cytidine (cytosine) or an analogue thereof,
    when l>1, at least 50% of these nucleotides (nucleosides) are cytidine (cytosine) or an analogue thereof;

m is an integer and is at least 3;
  wherein when m=3, X is uridine (uracil) or an analogue thereof,
    when m>3, at least 3 successive uridines (uracils) or analogues of uridine (uracil) occur;

n is an integer from 1 to 40,
  wherein when n=1, C is cytidine (cytosine) or an analogue thereof,
    when n>1, at least 50% of these nucleotides (nucleosides) are cytidine (cytosine) or an analogue thereof.

u, v may be independently from each other an integer from 0 to 50,
  preferably wherein when u=0, v≥1, or
    when v=0, u≥1;

wherein the nucleic acid molecule of formula (V) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (V), any of the definitions given above for elements N (i.e. $N_u$ and $N_v$) and X ($X_m$), particularly the core structure as defined above, as well as for integers a, l, m, n, u and v, similarly apply to elements of formula (V) correspondingly, wherein in formula (V) the core structure is defined by $C_l X_m C_n$. The definition of bordering elements $N_u$ and $N_v$ is identical to the definitions given above for $N_u$ and $N_v$.

According to a very particularly preferred embodiment, the inventive nucleic acid molecule according to formula (IV) may be selected from e.g. any of the following sequences:

(SEQ ID NO: 373)
UAGCGAAGCUCUUGGACCUAGGUUUUUUUUUUUUUUUGGGUGCGUUCCU

AGAAGUACACG (SEQ ID NO: 374)
UAGCGAAGCUCUUGGACCUAGGUUUUUUUUUUUUUUUGGGUGCGUUCCU

AGAAGUACACGAUCGCUUCGAGAACCUGGAUCCAAAAAAAAAAAAAAAC

CCACGCAAGGAUCUUCAUGUGC (SEQ ID NO: 375)
GGGAGAAAGCUCAAGCUUGGAGCAAUGCCCGCACAUUGAGGAAACCGAG

UUGCAUAUCUCAGAGUAUUGGCCCCCGUGUAGGUUAUUCUUGACAGACA

GUGGAGCUUAUUCACUCCCAGGAUCCGAGUCGCAUACUACGGUACUGGU

GACAGACCUAGGUCGUCAGUUGACCAGUCCGCCACUAGACGUGAGUCCG

UCAAAGCAGUUAGAUGUUACACUCUAUUAGAUC (SEQ ID NO: 376)
GGGAGAAAGCUCAAGCUUGGAGCAAUGCCCGCACAUUGAGGAAACCGAG

UUGCAUAUCUCAGAGUAUUGGCCCCCGUGUAGGUUAUUCUUGACAGACA

GUGGAGCUUAUUCACUCCCAGGAUCCGAGUCGCAUACUACGGUACUGGU

GACAGACCUAGGUCGUCAGUUGACCAGUCCGCCACUAGACGUGAGUCCG

UCAAAGCAGUUAGAUGUUACACUCUAUUAGAUCUCGGAUUACAGCUGGA

AGGAGCAGGAGUAGUGUUCUUGCUCUAAGUACCGAGUGUGCCCAAUACC

CGAUCAGCUUAUUAACGAACGGCUCCUCCUCUUAGACUGCAGCGUAAGU

GCGGAAUCUGGGGAUCAAAUUACUGACUGCCUGGAUUACCCUCGGACAU

AUAACCUUGUAGCACGCUGUUGCUGUAUAGGUGACCAACGCCCACUCGA

GUAGACCAGCUCUCUUAGUCCGGACAAUGAUAGGAGGCGCGGUCAAUCU

ACUUCUGGCUAGUUAAGAAUAGGCUGCACCGACCUCUAUAAGUAGCGUG

UCCUCUAG (SEQ ID NO: 377)
GGGAGAAAGCUCAAGCUUGGAGCAAUGCCCGCACAUUGAGGAAACCGAG
UUGCAUAUCUCAGAGUAUUGGCCCCGUGUAGGUUAUUCUUGACAGACA
GUGGAGCUUAUUCACUCCCAGGAUCCGAGUCGCAUACUACGGUACUGGU
GACAGACCUAGGUCGUCAGUUGACCAGUCCGCCACUAGACGUGAGUCCG
UCAAAGCAGUUAGAUGUUACACUCUAUUAGAUCUCGGAUUACAGCUGGA
AGGAGCAGGAGUAGUGUUCUUGCUCUAAGUACCGAGUGUGCCCAAUACC
CGAUCAGCUUAUUAACGAACGGCUCCUCCUCUUAGACUGCAGCGUAAGU
GCGGAAUCUGGGGAUCAAAUUACUGACUGCCUGGAUUACCCUCGGACAU
AUAACCUUGUAGCACGCUGUUGCUGUAUAGGUGACCAACGCCCACUCGA
GUAGACCAGCUCUCUUAGUCCGGACAAUGAUAGGAGGCGCGGUCAAUCU
ACUUCUGGCUAGUUAAGAAUAGGCUGCACCGACCUCUAUAAGUAGCGUG
UCCUCUAGAGCUACGCAGGUUCGCAAUAAAAGCGUUGAUUAGUGUGCAU
AGAACAGACCUCUUAUUCGGUGAAACGCCAGAAUGCUAAAUUCCAAUAA
CUCUUCCCAAAACGCGUACGGCCGAAGACGCGCGCUUAUCUUGUGUACG
UUCUCGCACAUGGAAGAAUCAGCGGGCAUGGUGGUAGGGCAAUAGGGGA
GCUGGGUAGCAGCGAAAAAGGGCCCCUGCGCACGUAGCUUCGCUGUUCG
UCUGAAACAACCCGGCAUCCGUUGUAGCGAUCCCGUUAUCAGUGUUAUU
CUUGUGCGCACUAAGAUUCAUGGUGUAGUCGACAAUAACAGCGUCUUGG
CAGAUUCUGGUCACGUGCCCUAUGCCCGGGCUUGUGCCUCUCAGGUGCA
CAGCGAUACUUAAAGCCUUCAAGGUACUCGACGUGGGUACCGAUUCGUG
ACACUUCCUAAGAUUAUUCCACUGUGUUAGCCCCGCACCGCCGACCUAA
ACUGGUCCAAUGUAUACGCAUUCGCUGAGCGGAUCGAUAAUAAAAGCUU
GAAUU (SEQ ID NO: 378)
GGGAGAAAGCUCAAGCUUAUCCAAGUAGGCUGGUCACCUGUACAACGUA
GCCGGUAUUUUUUUUUUUUUUUUUUUUUUUGACCGUCUCAAGGUCCAAGU
UAGUCUGCCUAUAAAGGUGCGGAUCCACAGCUGAUGAAAGACUUGUGCG
GUACGGUUAAUCUCCCCUUUUUUUUUUUUUUUUUUUUUUAGUAAAUGCGU
CUACUGAAUCCAGCGAUGAUGCUGGCCCAGAUC (R 722 SEQ ID NO: 379)
GGGAGAAAGCUCAAGCUUAUCCAAGUAGGCUGGUCACCUGUACAACGUA
GCCGGUAUUUUUUUUUUUUUUUUUUUUUUUGACCGUCUCAAGGUCCAAGU
UAGUCUGCCUAUAAAGGUGCGGAUCCACAGCUGAUGAAAGACUUGUGCG
GUACGGUUAAUCUCCCCUUUUUUUUUUUUUUUUUUUUUUAGUAAAUGCGU
CUACUGAAUCCAGCGAUGAUGCUGGCCCAGAUCUUCGACCACAAGUGCA
UAUAGUAGUCAUCGAGGGUCGCCUUUUUUUUUUUUUUUUUUUUUUUGGC
CCAGUUCUGAGACUUCGCUAGAGACUACAGUUACAGCUGCAGUAGUAAC
CACUGCGGCUAUUGCAGGAAAUCCCGUUCAGGUUUUUUUUUUUUUUUUU
UUUUCCGCUCACUAUGAUUAAGAACCAGGUGGAGUGUCACUGCUCUCGA
GGUCUCACGAGAGCGCUCGAUACAGUCCUUGGAAGAAUCUUUUUUUUUU
UUUUUUUUUUUUGUGCGACGAUCACAGAGAACUUCUAUUCAUGCAGGUC
UGCUCUA (SEQ ID NO: 380)
GGGAGAAAGCUCAAGCUUAUCCAAGUAGGCUGGUCACCUGUACAACGUA
GCCGGUAUUUUUUUUUUUUUUUUUUUUUUUGACCGUCUCAAGGUCCAAGU
UAGUCUGCCUAUAAAGGUGCGGAUCCACAGCUGAUGAAAGACUUGUGCG
GUACGGUUAAUCUCCCCUUUUUUUUUUUUUUUUUUUUUUAGUAAAUGCGU
CUACUGAAUCCAGCGAUGAUGCUGGCCCAGAUCUUCGACCACAAGUGCA
UAUAGUAGUCAUCGAGGGUCGCCUUUUUUUUUUUUUUUUUUUUUUUGGC
CCAGUUCUGAGACUUCGCUAGAGACUACAGUUACAGCUGCAGUAGUAAC
CACUGCGGCUAUUGCAGGAAAUCCCGUUCAGGUUUUUUUUUUUUUUUUU
UUUUCCGCUCACUAUGAUUAAGAACCAGGUGGAGUGUCACUGCUCUCGA
GGUCUCACGAGAGCGCUCGAUACAGUCCUUGGAAGAAUCUUUUUUUUUU
UUUUUUUUUUUUGUGCGACGAUCACAGAGAACUUCUAUUCAUGCAGGUC
UGCUCUAGAACGAACUGACCUGACGCCUGAACUUAUGAGCGUGCGUAUU
UUUUUUUUUUUUUUUUUUUUCCUCCCAACAAAUGUCGAUCAAUAGCUG
GGCUGUUGGAGACGCGUCAGCAAAUGCCGUGGCUCCAUAGGACGUGUAG
ACUUCUAUUUUUUUUUUUUUUUUUUUUUCCCGGGACCACAAAUAAUAUU
CUUGCUUGGUUGGGCGCAAGGGCCCCGUAUCAGGUCAUAAACGGGUACA
UGUUGCACAGGCUCCUUUUUUUUUUUUUUUUUUUUUUUUCGCUGAGUUAU
UCCGGUCUCAAAAGACGGCAGACGUCAGUCGACAACACGGUCUAAAGCA
GUGCUACAAUCUGCCGUGUUCGUGUUUUUUUUUUUUUUUUUUUUGUGAA
CCUACACGGCGUGCACUGUAGUUCGCAAUUCAUAGGGUACCGGCUCAGA
GUUAUGCCUUGGUUGAAAACUGCCCAGCAUACUUUUUUUUUUUUUUUU
UUUCAUAUUCCCAUGCUAAGCAAGGGAUGCCGCGAGUCAUGUUAAGCUU
GAAUU

According to another very particularly preferred embodiment, the nucleic acid molecule according to formula (V) may be selected from e.g. any of the following sequences:

(SEQ ID NO: 381)
UAGCGAAGCUCUUGGACCUACCUUUUUUUUUUUUUUCCCUGCGUUCCUA
GAAGUACACG
or
(SEQ ID NO: 382)
UAGCGAAGCUCUUGGACCUACCUUUUUUUUUUUUUUUCCCUGCGUUCCU
AGAAGUACACGAUCGCUUCGAGAACCUGGAUGGAAAAAAAAAAAAAAG
GGACGCAAGGAUCUUCAUGUGC

In a further preferred embodiment the nucleic acid molecule of the herein defined inventive polymeric carrier cargo complex may also occur in the form of a modified nucleic acid.

According to a first aspect, the nucleic acid molecule of the herein defined inventive polymeric carrier cargo complex may be provided as a "stabilized nucleic acid", preferably as a stabilized RNA or DNA, more preferably as a RNA that is essentially resistant to in vivo degradation (e.g. by an exo- or endo-nuclease).

In this context, the nucleic acid molecule of the herein defined inventive polymeric carrier cargo complex may contain backbone modifications, sugar modifications or base modifications. A backbone modification in connection with the present invention is a modification in which phosphates of the backbone of the nucleotides contained in the nucleic acid molecule of the inventive polymeric carrier cargo complex are chemically modified. A sugar modification in connection with the present invention is a chemical modification of the sugar of the nucleotides of the nucleic acid molecule of the inventive polymeric carrier cargo complex. Furthermore, a base modification in connection with the present invention is a chemical modification of the base moiety of the nucleotides of the nucleic acid molecule of the inventive polymeric carrier cargo complex.

According to a further aspect, the nucleic acid molecule of the herein defined inventive polymeric carrier cargo complex can contain a lipid modification. Such a lipid-modified nucleic acid typically comprises a nucleic acid as defined herein. Such a lipid-modified nucleic acid molecule of the inventive polymeric carrier cargo complex typically further comprises at least one linker covalently linked with that nucleic acid molecule, and at least one lipid covalently linked with the respective linker. Alternatively, the lipid-modified nucleic acid molecule comprises at least one nucleic acid molecule as defined herein and at least one (bifunctional) lipid covalently linked (without a linker) with that nucleic acid molecule. According to a third alternative, the lipid-modified nucleic acid molecule comprises a nucleic acid molecule as defined herein, at least one linker covalently linked with that nucleic acid molecule, and at least one lipid covalently linked with the respective linker, and also at least one (bifunctional) lipid covalently linked (without a linker) with that nucleic acid molecule.

The nucleic acid molecule of the inventive polymeric carrier cargo complex may likewise be stabilized in order to prevent degradation of the nucleic acid molecule by various approaches, particularly, when RNA or mRNA is used as a nucleic acid molecule for the inventive purpose. It is known in the art that instability and (fast) degradation of RNA in general may represent a serious problem in the application of RNA based compositions. This instability of RNA is typically due to RNA-degrading enzymes, "RNAases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance particularly for an mRNA. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

According to another aspect, the nucleic acid molecule of the herein defined inventive polymeric carrier cargo complex may be modified, and thus stabilized, especially if the nucleic acid molecule is in the form of a coding nucleic acid e.g. an mRNA, by modifying the G/C content of the nucleic acid molecule, particularly an mRNA, preferably of the coding region thereof.

In a particularly preferred aspect of the present invention, the G/C content of the coding region of the nucleic acid molecule of the herein defined inventive polymeric carrier cargo complex, especially if the nucleic acid molecule is in the form of an mRNA, is modified, particularly increased, compared to the G/C content of the coding region of its particular wild type coding sequence, i.e. the unmodified mRNA. The encoded amino acid sequence of the nucleic acid sequence is preferably not modified compared to the coded amino acid sequence of the particular wild type mRNA.

The modification of the G/C-content of the nucleic acid molecule of the herein defined inventive polymeric carrier cargo complex, especially if the nucleic acid molecule is in the form of an mRNA or codes for an mRNA, is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. According to the invention, the codons of the coding sequence or mRNA are therefore varied compared to its wild type coding sequence or mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Preferably, the G/C content of the coding region of the nucleic acid molecule of the herein defined inventive polymeric carrier cargo complex, especially if the nucleic acid is in the form of an mRNA or codes for an mRNA, is increased by at least 7%, more preferably by at least 15%, particularly preferably by at least 20%, compared to the G/C content of the coded region of the wild type mRNA. According to a specific aspect at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence.

In this context, it is particularly preferable to increase the G/C content of the nucleic acid molecule of the herein defined inventive polymeric carrier cargo complex, especially if the nucleic acid is in the form of an mRNA or codes for an mRNA, to the maximum (i.e. 100% of the substitutable codons), in particular in the region coding for a protein, compared to the wild type sequence.

According to the invention, a further preferred modification of the nucleic acid molecule of the herein defined inventive polymeric carrier cargo complex, especially if the nucleic acid is in the form of an mRNA or codes for an mRNA, is based on the finding that the translation efficiency is also determined by a different frequency in the occurrence of tRNAs in cells. Thus, if so-called "rare codons" are present in the nucleic acid molecule of the inventive polymeric carrier cargo complex, especially if the nucleic acid is in the form of an mRNA or codes for an mRNA, to an increased extent, the corresponding modified nucleic acid molecule is translated to a significantly poorer degree than in the case where codons coding for relatively "frequent" tRNAs are present.

Especially if the modified nucleic acid molecule of the herein defined inventive polymeric carrier cargo complex is in the form of an mRNA or codes for an mRNA, the coding region of the modified nucleic acid is preferably modified compared to the corresponding region of the wild type mRNA or coding sequence such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the nucleic acid molecule of the inventive polymeric carrier cargo complex, especially if the nucleic acid is in the form of an mRNA or codes for an mRNA, is modified such that codons for which frequently occurring tRNAs are available are inserted. In other words, according to the invention, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified nucleic acid molecule of the herein defined inventive polymeric carrier cargo complex, especially if the nucleic acid is in the form of an mRNA or codes for an mRNA, with the "frequent" codons without modifying the amino acid sequence of the protein encoded by the coding region of the nucleic acid molecule. This preferred aspect allows provision of a particularly efficiently translated and stabilized (modified) nucleic acid molecule of the inventive polymeric carrier cargo complex, especially if the nucleic acid is in the form of an mRNA or codes for an mRNA.

According to a further preferred aspect of the invention, the nucleic acid molecule of the inventive polymeric carrier cargo complex as defined herein, especially if the nucleic acid is in the form of a coding nucleic acid molecule, preferably has at least one 5' and/or 3' stabilizing sequence. These stabilizing sequences in the 5' and/or 3' untranslated regions have the effect of increasing the half-life of the nucleic acid in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from *Homo sapiens* or *Xenopus laevis* may be mentioned as an example of stabilizing sequences which can be used in the present invention for a stabilized nucleic acid. Another example of a stabilizing sequence has the general formula (C/U)CCAN$_x$CCC(U/A)Py$_x$UC(C/U)CC (SEQ ID NO: 383), which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art.

Nevertheless, substitutions, additions or eliminations of bases are preferably carried out with the nucleic acid molecule of the inventive polymeric carrier cargo complex as defined herein, especially if the nucleic acid is in the form of an mRNA, using a DNA matrix for preparation of the nucleic acid molecule by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N.Y., 2001). In such a process, for preparation of the nucleic acid molecule of the inventive polymeric carrier cargo complex as defined herein, especially if the nucleic acid is in the form of an mRNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the nucleic acid molecule, e.g. mRNA, to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

Nucleic acid molecules used according to the invention as defined herein may be prepared using any method known in the art, including synthetic methods such as e.g. solid phase synthesis, as well as in vitro methods, such as in vitro transcription reactions.

According to another particularly preferred aspect, the nucleic acid molecule of the inventive polymeric carrier cargo complex as defined herein, especially if the nucleic acid is in the form of a coding nucleic acid molecule may additionally or alternatively encode a secretory signal peptide. Such signal peptides are sequences, which typically exhibit a length of about 15 to 30 amino acids and are preferably located at the N-terminus of the encoded peptide, without being limited thereto. Signal peptides as defined herein preferably allow the transport of the protein or peptide as encoded by the nucleic acid molecule of the inventive polymeric carrier cargo complex as defined herein, especially if the nucleic acid is in the form of an mRNA, into a defined cellular compartment, preferably the cell surface, the endoplasmic reticulum (ER) or the endosomal-lysosomal compartment. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulins as defined herein, signal sequences of the invariant chain of immunoglobulins or antibodies as defined herein, signal sequences of Lamp1, Tapasin, Erp57, Calreticulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention.

Any of the above modifications may be applied to the nucleic acid molecule of the inventive polymeric carrier cargo complex as defined herein and further to any nucleic acid as used in the context of the present invention and may be, if suitable or necessary, be combined with each other in any combination, provided, these combinations of modifications do not interfere with each other in the respective nucleic acid. A person skilled in the art will be able to take his choice accordingly.

The nucleic acid molecule of the inventive polymeric carrier cargo complex as defined herein as well as proteins or peptides as encoded by this nucleic acid molecule may comprise fragments or variants of those sequences. Such fragments or variants may typically comprise a sequence having a sequence identity with one of the above mentioned nucleic acids, or with one of the proteins or peptides or sequences, if encoded by the at least one nucleic acid molecule, of at least 5%, 10%, 20%, 30%, 40%, 50%, 60%, preferably at least 70%, more preferably at least 80%, equally more preferably at least 85%, even more preferably at least 90% and most preferably at least 95% or even 97%, 98% or 99%, to the entire wild type sequence, either on nucleic acid level or on amino acid level.

"Fragments" of proteins or peptides in the context of the present invention (encoded by a nucleic acid as defined herein) may comprise a sequence of a protein or peptide as defined herein, which is, with regard to its amino acid sequence (or its encoded nucleic acid molecule), N-terminally, C-terminally and/or intrasequentially truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Likewise, "fragments" of nucleic acids in the context of the present invention may comprise a sequence of a nucleic acid as defined herein, which is, with regard to its nucleic acid molecule 5'-, 3'- and/or intrasequentially truncated compared to the nucleic acid molecule of the original (native) nucleic acid molecule. A sequence identity with respect to such a fragment as defined herein may therefore preferably refer to the entire nucleic acid as defined herein.

Fragments of proteins or peptides in the context of the present invention (e.g. as encoded by the nucleic acid molecule of the inventive polymeric carrier cargo complex) may furthermore comprise a sequence of a protein or peptide as defined herein, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form.

Fragments of proteins or peptides as defined herein (e.g. as encoded by the nucleic acid molecule of the inventive polymeric carrier cargo complex) may also comprise epitopes of those proteins or peptides. Epitopes (also called "antigen determinants") in the context of the present invention are typically fragments located on the outer surface of (native) proteins or peptides as defined herein, preferably having 5 to 15 amino acids, more preferably having 5 to 12 amino acids, even more preferably having 6 to 9 amino acids, which may be recognized by antibodies or B-cell receptors, i.e. in their native form. Such epitopes of proteins or peptides may furthermore be selected from any of the herein mentioned variants of such proteins or peptides. In this context antigenic determinants can be conformational or discontinous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

"Variants" of proteins or peptides as defined in the context of the present invention (e.g. as encoded by a nucleic acid as defined herein) may be encoded by the nucleic acid molecule of the inventive polymeric carrier cargo complex. Thereby, a protein or peptide may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property.

"Variants" of proteins or peptides as defined in the context of the present invention (e.g. as encoded by a nucleic acid as defined herein) may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein, which may be encoded by the nucleic acid molecule of the inventive polymeric carrier cargo complex, may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences them selves, the sequences can be aligned in order to be subsequently compared to one another. Therefore, e.g. a position of a first sequence may be compared with the corresponding position of the second sequence. If a position in the first sequence is occupied by the same component as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

In the inventive polymeric carrier cargo complex, the cationic component of the polymeric carrier as defined herein and the nucleic acid cargo are typically provided in a molar ratio of about 1 to 10000, preferably in a molar ratio of about 5 to 5000, more preferably in a molar ratio of about 10 to 2500, even more preferably in a molar ratio of about 25 to 2000, and most preferably in a molar ratio of about 25 to 1000 of polymeric carrier to nucleic acid.

Furthermore, in the inventive polymeric carrier cargo complex, the cationic component of the polymeric carrier as defined herein and the nucleic acid cargo are preferably provided in an N/P-ratio of at least 0.1, 0.2, 0.3, 0.4, 0.5, 0.75, 1, 1.5 or 2. Preferably, the N/P-ratio lies within a range of about 0.1, 0.3, 0.4, 0.5, 0.75, 1.0, 1.5 or 2 to 20, preferably in a range of about 0.2 (0.5 or 0.75 or 1.0) to 12, and even more preferably in an N/P-ratio of about 0.4 (0.75 or 1.0) to 10. In this context, the N/P ratio is a measure of the ionic charge of the cationic (side chain) component of the polymeric carrier or of the polymeric carrier as such. In particular, if the cationic properties of the cationic component are generated by nitrogens (of the amino acid side chains), the N/P ratio expresses the ratio of basic nitrogen atoms to phosphate residues in the nucleotide backbone, considering that (side chain) nitrogen atoms in the cationic component of the polymeric carrier contribute to positive charges and phosphate of the phosphate backbone of the nucleic acid contribute to the negative charge. A formula is given in the Examples. The N/P-ratio is defined as the nitrogen/phosphate ratio (N/P-ratio) of the entire inventive polymeric carrier cargo complex. This is typically illustrative for the content/amount of cationic components, in the polymeric carrier and characteristic for the content/amount of nucleic acids bound or complexed in the inventive polymeric carrier cargo complex. It may be calculated on the basis that, for example, 1 µg RNA typically contains about 3 nmol phosphate residues, provided that RNA exhibits a statistical distribution of bases. Additionally, 1 nmol peptide typically contains about x nmol nitrogen residues, dependent on the molecular weight and the number of its (cationic) amino acids.

In this context it is preferable that in the inventive polymeric carrier cargo complex, the cationic component of the polymeric carrier as defined herein and the nucleic acid cargo are provided in an N/P-ratio of at least about 1 or, preferably, of a range of about 1 to 20 for in vitro transfection purposes.

If the expression of an encoded protein or the transcription of an encoded nucleic acid e.g. an mRNA or siRNA of the nucleic acid cargo is intended for therapeutical purposes (in vivo application) an N/P ratio of at least 0.1 (0.2, 0.3, 0.4, 0.5, 0.6), preferably of a range of about 0.1 (0.2, 0.3, 0.4, 0.5, or 0.6) to 1.5 is preferred. Even more preferred is an N/P ratio range of 0.2 to 0.9 or an N/P ratio range of 0.5 to 0.9. In the case that the inventive polymeric carrier cargo complex is used for (in vivo) immunostimulation e.g. as an immunostimulating agent or adjuvant (for the purpose to induce an innate immune response), an N/P ratio of about 0.1 to 20 is preferred, more particular an N/P ratio of 0.1 to 5 or 0.1 to 1.5.

In the specific case that the induction of IFN-α is intended using the inventive polymeric cargo complex as an (in vivo) immunostimulating agent or adjuvant an N/P ratio of at least 0.1 (0.2, 0.3, 0.4, 0.5, or 0.6) or an N/P ratio range of 0.1 to 1 is preferred or more preferred is an N/P ratio range of 0.2 to 0.9 or an N/P ratio range of 0.5 to 0.9. Otherwise if the induction of TNFα is intended using the inventive polymeric cargo complex as an (in vivo) immunostimulating agent or adjuvant an N/P ratio of 1 to 20 is particularly preferred.

The N/P ratio significantly influences the surface charge of the resulting inventive polymeric carrier cargo complex. Thus it is preferable that the resulting inventive polymeric carrier cargo complex is positively charged for in vitro transfection purposes and negatively or neutrally charged for in vivo transfection purposes, especially if the expression of an encoded protein or the transcription of an encoded nucleic acid of the nucleic acid cargo is intended. The surface charge of the resulting inventive polymeric carrier cargo complex can be indicated as Zetapotential which may be measured by Doppler electrophoresis method using a Zetasizer Nano (Malvern Instruments, Malvern, UK).

The present invention also provides a method of preparing the inventive polymeric carrier cargo complex as defined herein comprising following steps:

a) providing at least one cationic protein or peptide as defined herein and/or at least one cationic or polycationic polymer and optionally at least one amino acid component (AA) as defined herein, each comprising at least one —SH moiety, b) providing at least one nucleic acid molecule as defined herein, preferably in the above mentioned ratios c) mixing the components provided in steps a) and b), preferably in a basic or neutral milieu as defined herein, preferably in the presence of oxygen or a further starter as defined herein, preferably at a pH, at a temperature and at time as defined herein, and thereby condensing and thus polymerizing the cationic components provided in step a) with each other via disulfide bonds (in a polymerization condensation or polycondensation) to obtain the polymeric carrier and complexing the nucleic acid molecule provided in step b) with the cationic components provided in step a)

d) optionally purifying the inventive polymeric carrier cargo complex obtained according to step c), preferably using a method as defined herein;

e) optionally lyophilization of the inventive polymeric carrier cargo complex obtained according to step c) or d).

The method of preparing the inventive polymeric carrier cargo complex as defined herein comprises a multi-step condensation polymerization or polycondensation reaction via —SH moieties of the educts e.g. cationic peptides or polymers as defined herein and optionally further amino acid components (AA) in step c). The condensation polymerization or polycondensation reaction which occurs simultaneously to the complexation or electrostatic binding of the nucleic acid molecule preferably leads to the inventive polymeric carrier cargo complex wherein the polymeric carrier is a condensation polymer, wherein the single components are linked by disulfide bonds.

As defined herein in a step a) of the inventive method of preparing the inventive polymeric carrier cargo complex, at least one cationic or polycationic protein or peptide as defined herein and/or at least one cationic or polycationic polymer as defined herein are provided, preferably in the ratios indicated above. These components are mixed in step c) with the nucleic acid molecule provided in step b), preferably in a basic or neutral milieu as defined herein, preferably in the presence of oxygen or a further starter as defined herein, preferably at a pH, and at a temperature and at a time as defined herein, and thereby condensing and thus polymerizing these components with each other via disulfide bonds (in a polymerization condensation or polycondensation) to obtain a polymeric carrier complexed to the nucleic acid molecule as defined herein.

According to an alternative, in step a) of the inventive method of preparing the inventive polymeric carrier cargo complex at least one cationic or polycationic protein or peptide and/or at least one cationic or polycationic polymer are provided as defined herein, and optionally at least one amino acid component (AA), are provided in step a) as defined herein, and are used for a polymerization condensation or polycondensation and complexation reaction prior to adding the nucleic acid of step b) but using the same polymerization conditions outlined for step c). The polymerized polymeric carrier and the nucleic acid of step b) are then mixed in step c). Preferably, the components are all provided in the ratios indicated above and mixed, preferably in a basic or neutral milieu as defined herein, preferably in the presence of oxygen or a further starter as defined herein, preferably at a pH, at a temperature and at time as defined herein. Upon mixing and starting the reaction, the components are condensed and thus polymerized with each other via disulfide bonds (in a polymerization condensation or polycondensation) to obtain a polymeric carrier complexed to the nucleic acid molecule as defined herein.

In both of the above alternatives, different polymeric carriers, particularly different peptides and/or different polymers, and may be selected in the condensation polymerization as indicated above. In this context, the selection of different component(s) of the polymeric carrier is typically dependent upon the desired properties of the final polymeric carrier and the desired cationic strength of the final polymeric carrier. Accordingly, the content of cationic components, may furthermore be "diluted" or modified in the above alternative of step a) e.g. by introducing an amino acid component (AA) as defined herein, preferably in the above defined ratios. Thereby, a modified polymeric carrier may be obtained, wherein the cationic character of the unmodified polymeric carrier typically remains in the limitations as defined herein. The properties of the final polymeric carrier may thus be adjusted as desired with properties of components (AA) by inserting amino acid component (AA) as defined herein in steps a).

In step c), the at least one cationic or polycationic protein or peptide as defined herein and/or at least one cationic or polycationic polymer as defined herein, and optionally at least one amino acid component (AA) and the at least one nucleic acid as defined herein, are preferably contained in a basic or neutral milieu in the step a) of the inventive method of preparing the inventive polymeric carrier cargo complex. Such a basic or neutral milieu typically exhibits a pH range of about 5 to about 10, preferably a pH range of about 6 to about 9, more preferably a pH range of about 7 to about 8, e.g. about 6.5, 7, 7.5, 8, 8.5, or 9 or any range selected from any two of these or the aforementioned values.

Furthermore, the temperature of the solution in step c) is preferably in a range of about 5° C. to about 60° C., more preferably in a range of about 15° C. to about 40° C., even more preferably in a range of about 20° C. to about 30° C., and most preferably in a range of about 20° C. to about 25° C., e.g. about 25° C.

In step c) of the inventive method of preparing the inventive polymeric carrier cargo complex as defined herein buffers may be used as suitable. Preferred buffers may comprise, but are not limited to carbonate buffers, borate buffers, Bicine buffer, CHES buffer, CAPS buffer, Ethanolamine containing buffers, HEPES, MOPS buffer, Phosphate buffer, PIPES buffer, Tris buffer, Tricine buffer, TAPS buffer, and/or TES buffer as buffering agents. Particularly preferred is a carbonate buffer.

Upon mixing the components, preferably in the presence of oxygen, preferably in the presence of a basic or neutral mileu as defined herein, the condensation polymerization or polycondensation reaction and the complexation of the at least one nucleic acid molecule is started. For this purpose, the mixture in step c) is preferably exposed to oxygen or may be started using a further starter, e.g. a catalytic amount of an oxidizing agent, e.g. DMSO, etc. Upon start of the condensation polymerization or polycondensation reaction of the at least one cationic or polycationic protein or peptide and/or at least one cationic or polycationic polymer and optionally at least one amino acid component (AA) as defined herein, are condensed and thus polymerized with each other via disulfide bonds (polymerization condensation or polycondensation). In this reaction step a) preferably linear polymers are created using monomers with at least one reactive —SH moiety, i.e. at least one cationic or polycationic protein or peptide and/or at least one cationic or polycationic polymer and optionally at least one amino acid component (AA) as defined herein, each component exhibiting at least one free —SH-moieties as defined herein, e.g. at their terminal ends. However, components with more than one, preferably two free —SH-moieties may be used, which may lead to branched polymers. Simultaneously to the polymerization reaction the cationic polymers bind to the at least one nucleic acid molecule and thereby complexing it.

According to one alternative, the inventive polymeric carrier cargo complex additionally may be modified with a component (AA) as defined herein.

According to a first example, a component (AA) (e.g. a ligand) is attached to the cationic component prior to providing the cationic component in step a) via any functionality as defined herein, e.g. a —SH moiety. This component (AA) or (e.g. a ligand) is preferably attached to the cationic component at one terminus of these components. If the attachment is carried out via —SH bonds, the cationic components are preferably provided with two (or even more) —SH-moieties. The component (AA) or (e.g. a ligand) preferably carries only one —SH moiety. In this case, one —SH moiety of the cationic component is preferably protected in a first step using a protecting group as known in the art. Then, the cationic component may be bound to a component L to form a first disulfide bond via the non-protected —SH moiety. The protected —SH-moiety of the cationic component is then typically deprotected for further reactions.

Alternatively, the above mentioned component (AA) or (e.g. a ligand) may be used in step c) to be coupled with the cationic components provided in step a) above, e.g. via disulfide bonds without blocking the free —SH moieties. But in this context all methods known to a skilled person or defined herein may be used to attach the component (AA) to the cationic component or to the polymeric carrier.

Alternatively, a component (AA) or (e.g. a ligand) can be bound to the inventive polymeric carrier cargo complex after step c) via any functionality as defined herein, e.g. a —SH moiety. In this context it is preferable that the component (AA) (e.g. a ligand) is bound via free —SH moieties of the polymeric carrier components.

According to step c) of the inventive method of preparing the inventive polymeric carrier cargo complex as defined herein, at least one nucleic acid molecule as defined herein is mixed with the cationic components provided in step b), preferably in the above mentioned ratios. Typically, in the inventive polymeric carrier cargo complex, the cationic components as defined herein, and the at least one nucleic acid molecule are provided in a molar ratio of about 5 to 10000, preferably in a molar ratio of about 5 to 5000, more preferably in a molar ratio of about 10 to 2500, even more preferably in a molar ratio of about 10 to 1000 cationic polymer to nucleic acid. The N/P ratios are preferably as indicated above. In this context it is particularly preferred that the N/P ratios are selected thereby avoiding agglomeration and toxicity in vivo.

In a specific embodiment, (AA) components as defined above which do not comprise —SH moieties can be added in step c) which are thereby incorporated into the inventive polxmeric carrier cargo complex without polymerization by (terminal) —SH moieties. Thereby these (AA) components is/are typically not covalently linked and included non-covalently in the inventive complex as a further component.

According to a further step d) of the inventive method of preparing the inventive polymeric carrier cargo complex as defined herein, the inventive polymeric carrier cargo complex obtained according to step c) is optionally purified. Purification may occur by using chromatographic methods, such as HPLC, FPLC, GPS, dialysis, etc.

According to a further step e) of the inventive method of preparing the inventive polymeric carrier cargo complex as defined herein, the inventive polymeric carrier cargo complex obtained according to step c) or d) is optionally lyophilized. For this purpose any suitable cryoprotectant or lyoprotectant may be added to the inventive polymeric carrier cargo complex obtained in step c) or d).

The inventive method of preparing the inventive polymeric carrier cargo complex as defined herein is particularly suitable to adapt the chemical properties of the desired inventive polymeric carrier cargo complex due to specific selection of its components of the polymeric carrier thereby avoiding agglomeration and toxicity in vivo.

According to a further embodiment, the present invention also provides a method for transfecting a cell, a tissue or an organism, thereby applying or administering the inventive polymeric carrier cargo complex, particularly for therapeutic purposes. In this context, typically after preparing the inventive polymeric carrier cargo complex as described above, the inventive polymeric carrier cargo complex is preferably or administered to a cell, a tissue or an organism, preferably in naked form or as a pharmaceutical composition or vaccine as described herein, more preferably using any of the administration modes as described herein. The method for transfecting a cell may be carried out in vitro, in vivo or ex vivo.

Likewise, according to another embodiment, the present invention also relates to the use of the inventive polymeric carrier cargo complex, particularly for therapeutic purposes, for transfecting a cell, a tissue or an organism, thereby applying or administering the inventive polymeric carrier cargo complex as described above to a cell, a tissue or an organism, preferably in naked form or as a pharmaceutical composition or vaccine as described herein, more preferably using any of the administration modes as described herein. The administration may be carried out in vitro, in vivo or ex vivo.

Accordingly, in a particular preferred embodiment, the present invention also provides a pharmaceutical composition, comprising the inventive polymeric carrier cargo complex formed by a nucleic acid cargo as defined herein and the polymeric carrier as defined herein. The pharmaceutical composition optionally comprises a pharmaceutically acceptable carrier and/or vehicle.

As a first ingredient, the inventive pharmaceutical composition comprises the inventive polymeric carrier cargo complex formed by the nucleic acid cargo and the polymeric carrier as defined herein (and, optionally, (AA) component(s)).

As a second ingredient the inventive pharmaceutical composition may comprise at least one additional pharmaceutically active component. A pharmaceutically active component in this connection is a compound that has a therapeutic effect to heal, ameliorate or prevent a particular indication, preferably cancer diseases, autoimmune disease, allergies or infectious diseases. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the inventive polymeric carrier cargo complex as defined herein in such a manner that no interaction occurs which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

According to a specific aspect, the inventive pharmaceutical composition may comprise an (additional) adjuvant. In this context, an adjuvant may be understood as any compound, which is suitable to initiate or increase an immune response of the innate immune system, i.e. a nonspecific immune response. With other words, when administered, the inventive pharmaceutical composition typically elicits an innate immune response due to the adjuvant, optionally contained therein. Such an adjuvant may be selected from any adjuvant known to a skilled person and suitable for the present case, i.e. supporting the induction of an innate immune response in a mammal.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-nodal, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-nodal, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

The inventive pharmaceutical composition as defined herein may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added.

For oral administration in a capsule form, useful diluents include lactose and dried cornstarch. When aqueous suspensions are required for oral use, the active ingredient, i.e. the inventive polymeric carrier cargo complex, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive polymeric carrier cargo complex suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

The inventive pharmaceutical composition typically comprises a "safe and effective amount" of the components of the inventive pharmaceutical composition, particularly of the inventive polymeric carrier cargo complex as defined herein or the nucleic acid as such. As used herein, a "safe and effective amount" means an amount of the inventive polymeric carrier cargo complex as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment. A "safe and effective amount" of the components of the inventive pharmaceutical composition, particularly of the inventive polymeric carrier cargo complex as defined herein, will furthermore vary in connection with the particular condition to be treated and also with the age and physical condition of the patient to be treated, the body weight, general health, sex, diet, time of administration, rate of excretion, drug combination, the activity of the inventive polymeric carrier cargo complex, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine, immunostimulating agent or adjuvant.

According to a particular preferred embodiment, the inventive pharmaceutical composition (or the inventive polymeric carrier cargo complex) may be provided or used as an immunostimulating agent. In this context, the inventive pharmaceutical composition is preferably as defined above. More preferably, the nucleic acid of the inventive polymeric carrier cargo complex, preferably contained in the pharmaceutical composition, is typically an immunostimulatory nucleic acid as defined herein, e.g. a CpG-DNA or an immunostimulatory RNA (isRNA). Alternatively or additionally, the nucleic acid of the inventive polymeric carrier cargo complex, preferably contained in the pharmaceutical composition, is a coding nucleic acid as defined herein, preferably a cDNA or an mRNA, more preferably encoding an adjuvant protein preferably as defined herein.

In a specific embodiment in this context, it is preferred that an adjuvant protein is a component of the inventive polymeric carrier cargo complex and, preferably, of the polymeric carrier.

According to an even more preferred embodiment, the inventive pharmaceutical composition (or the inventive polymeric carrier cargo complex) may be provided or used as an adjuvant. In this context, the adjuvant is preferably defined as the inventive pharmaceutical composition above. More preferably, the nucleic acid of the inventive polymeric carrier cargo complex, preferably contained in the adjuvant, is typically an immunostimulatory nucleic acid as defined herein, e.g. a CpG-DNA or an immunostimulatory RNA (isRNA). Alternatively or additionally, the nucleic acid of the inventive polymeric carrier cargo complex, preferably contained in the adjuvant, is a coding nucleic acid as defined herein, preferably a cDNA or an mRNA, more preferably encoding an adjuvant protein, preferably as defined herein. The inventive polymeric carrier cargo complex, preferably contained in the adjuvant, typically initiates an innate immune response in the patient to be treated. Such an adjuvant may be utilized in any accompanying therapy, with any known vaccine or any further (known) therapeutic agent, preferably prior to, concurrent with or subsequent to administration of the main therapy, prior to, concurrent with or subsequent to administration of a further (known) vaccine or a (known) further therapeutic agent.

The inventive polymeric carrier cargo complex or the inventive pharmaceutical composition as defined herein provided or used as an adjuvant is preferably capable of triggering a non-antigen-specific, (innate) immune reaction (as provided by the innate immune system), preferably in an immunostimulating manner. An immune reaction can generally be brought about in various ways. An important factor for a suitable immune response is the stimulation of different T-cell sub-populations. T-lymphocytes typically differentiate into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the immune response. In connection with the present invention, the Th1/Th2 ratio of the immune response is preferably displaced by the immune-stimulating agent, namely the inventive polymeric carrier cargo complex in the direction towards the cellular response, that is to say the Th1 response, and a predominantly cellular immune response is thereby induced. As defined above, the inventive polymeric carrier cargo complex exerts by itself an unspecific innate immune response, which allows the inventive polymeric carrier cargo complex be used as such (without adding another pharmaceutically active component) as an immunostimulating agent. If administered together with another pharmaceutically active component, preferably a specifically immunogenic component, preferably an antigen, the nucleic acid of the invention serves as an adjuvant supporting the specific adaptive immune response elicited by the other pharmaceutically active component e.g. an antigen.

Determination of the (Innate) Immunostimulatory or Adjuvant Capacity of an Inventive Compound or an Inventive Complex:

For the determination of the immunostimulatory capacity of an inventive compound or an inventive complex several methods are known in the art and may be used. E.g., in vitro methods are advantageous to screen for compounds as to their capacity to induce cytokines, which are (exclusively or at least typically) part of the innate immune system and thereby (as an additional arm of the immune system) typically improve the induction of an antigen-specific immune response caused by an antigen. For this purpose, e.g. PBMCs may be isolated from blood samples and stimulated with the particular compound or complex. After incubation, secretion of the desired cytokines (e.g. as a reaction of an activation of the PAMP receptors) being typically part of the innate immune system (and not of the antigen-specific immune system) is determined by ELISA. These selected cytokines may be used in the art as determinants of the induction of an innate immune response in the body. In this context, the secretion of TNF-alpha and IFN-alpha is preferably measured to determine the unspecific (innate immune response) evoked by a compound or complex. Especially, IFN-alpha plays an important role in the induction of an unspecific immune response after viral infection. Accordingly, it is particularly preferred that the immunostimulatory compound or complex, which shall be identified by the screening assay, induces the secretion of e.g. IFN-alpha. Such a compound or complex may then be applied e.g. for the use as an immunotimualting agent (triggering the unspecific (innate) immune response) in vaccination therapies.

IFN-alpha is part of the family of type I interferons. Type I interferons (IFN) are pleiotropic cytokines that are essential for supporting anti-viral immune responses. They induce apoptosis of virus-infected cells and cellular resistance to viral infection, in addition to activating natural killer (NK) and T cells. Type I interferons have effects on a large set of cytokines and chemokines that i.a. influence immunocyte maturation, homing, effector functions and apoptosis. Typically, a major role of IFN-α/β is the induction of a priming state affecting the production and regulation of other mediators, including cytokines. For example, IFN-α/β signaling upregulates IFN-γ production by dendritic cells (DCs) and T cells and thereby favours the induction and maintenance of Th1 cells. Shifting of an immune response in direction of a Th1 immune response may become important, once protein or peptide vaccines are used, because these vaccines usually induce a Th2-based immune response which consequently prevents the induction of cytotoxic T cells.

Therefore, it is preferred that a compound or complex to be used as an adjuvant may preferably have the property of shifting an antigen-specific immune response caused by a vaccine to a Th1-based immune response. The direction of an immune response induced by a vaccine is usually measured by determination of the induction of several subtypes of antigen-specific antibodies and the induction of antigen-specific cytotoxic CD8+ T cells. In this context, the subtype antibody IgG1 represents the induction of a Th2-based immune response and the induction of the subtype antibody IgG2a and the induction of cytotoxic T cells represent the induction of a Th1-based immune response. The induction of antigen-specific antibodies is determined by measurement of the antibody titer in the blood of the vaccine by ELISA. The induction of antigen-specific cytotoxic T cells is determined by measurement of IFN-gamma secretion in splenocytes after stimulation with antigen-specific peptides by ELISPOT. In this context, the induction of IFN-gamma secretion proves that antigen-specific cytotoxic T cells are present in the spleen which can specifically attack cells which present epitopes of the antigen on MHC I molecules on their surface.

Thus, for the determination of beneficial properties of an adjuvant in vivo vaccinations are performed. Therewith, it is possible to find out, if the adjuvant or immunostimulatory compound or complex improves an antigen-specific immune response caused by the vaccine and, furthermore, if it can shift an antigen-specific immune response in the desired direction to display adjuvant properties. Particularly, in the induction of an anti-tumoral immune response the induction of a Th1-shifted immune response, especially the induction of cytotoxic T cells plays a major role, because the induction of antigen-specific cytotoxic T cells represents an indispensable prerequisite for the successful combat of a tumour.

Accordingly, the methods to screen for compound or complexes which actually exhibit properties as immunostimulating agents and/or adjuvants are well known in the art and may readily be applied e.g. by ELISA tests measuring the immune response elicited by the tested compounds/complexes.

According to another particularly preferred embodiment, the inventive pharmaceutical composition (or the inventive polymeric carrier cargo complex) may be provided or used as a vaccine.

In this context, the vaccine is preferably defined as an adjuvant or as an inventive pharmaceutical composition as disclosed above. More preferably, the nucleic acid of the inventive polymeric carrier cargo complex, preferably contained such a vaccine, may be any nucleic acid as defined above, preferably an immunostimulatory nucleic acid as defined herein, e.g. a CpG-DNA or an immunostimulatory RNA (isRNA). Alternatively or additionally, the nucleic acid of the inventive polymeric carrier cargo complex, preferably contained in the vaccine, is a coding nucleic acid as defined herein, preferably a cDNA or an mRNA, more preferably encoding an adjuvant protein, preferably as defined herein. Alternatively or additionally, the nucleic acid of the inventive polymeric carrier cargo complex, preferably contained in the vaccine, is a coding nucleic acid as defined herein, preferably a cDNA or an mRNA, more preferably encoding an antigen, preferably as defined herein. Furthermore, particularly, if the nucleic acid of the inventive polymeric carrier cargo complex does not encode an antigen, the inventive vaccine may contain an antigen, preferably as defined above, either as a protein or peptide or encoded by a nucleic acid, or antigenic cells, antigenic cellular fragments, cellular fractions; cell wall components (e.g. polysaccharides), modified, attenuated or de-activated (e.g. chemically or by irradiation) pathogens (virus, bacteria etc.).

According to a first aspect such an inventive vaccine is typically composed like the inventive adjuvant and preferably supports or elicits an innate immune response of the immune system of a patient to be treated, if an immunostimulatory nucleic acid is used as the nucleic acid molecule of the inventive polymeric carrier cargo complex.

According to a second aspect the inventive vaccine may elicit an adaptive immune response, preferably, if the nucleic acid of the inventive polymeric carrier cargo complex as defined herein encodes an antigen as defined herein, suitable to elicit an adaptive immune response. Alternatively, this antigen can be in form of a peptide, a protein or an epitope or may be provided as an additional nucleic acid encoding said antigen. The antigen may also be a component of the inventive polymeric carrier, e.g. as a (AA) component, as defined herein.

The inventive vaccine, immunostimulating agent or adjuvant may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive vaccine is to be administered orally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine, immunostimulating agent or adjuvant can additionally contain one or more auxiliary substances in order to increase its immunogenicity or immunostimulatory capacity, if desired. A synergistic action of the inventive polymeric carrier cargo complex as defined herein and of an auxiliary substance, which may be optionally contained in the inventive vaccine, immunostimulating agent or adjuvant as defined herein, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the inventive vaccine, immunostimulating agent or adjuvant are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine, immunostimulating agent or adjuvant can also additionally contain any further compound, which is known to be immunostimulating due to its binding affinity (as ligands) to human Toll-like receptors TLR1, TLR2, TLR5, TLR4, TLR5, TLR6, TLR7, TLR8, TLR9, TLR10, or due to its binding affinity (as ligands) to murine Toll-like receptors TLR1, TLR2, TLR5, TLR4, TLR5, TLR6, TLR7, TLR8, TLR9, TLR10, TLR11, TLR12 or TLR13.

The inventive vaccine, immunostimulating agent or adjuvant can also additionally or alternatively contain an immunostimulatory RNA, i.e. an RNA derived from an immunostimulatory RNA, which triggers or increases an (innate) immune response. Preferably, such an immunostimulatory RNA may be in general be as defined hereinbefore.

Another class of compounds, which may be added to an inventive vaccine, immunostimulating agent or adjuvant in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

The present invention furthermore provides several applications and uses of the inventive polymeric carrier cargo complex as defined herein, the inventive pharmaceutical composition, the inventive immunostimulating agent or adjuvant and the inventive vaccine comprising same or of kits comprising same.

According to one specific embodiment, the present invention is directed to the first medical use of the inventive polymeric carrier cargo complex as defined herein as a medicament, preferably as an immunostimulating agent, adjuvant or vaccine or in the field of gene therapy.

According to another embodiment, the present invention is directed to the second medical use of the inventive polymeric carrier cargo complex as defined herein, for the treatment of diseases as defined herein, preferably to the use of inventive polymeric carrier cargo complex as defined herein, of a pharmaceutical composition, vaccine, immunostimulating agent, adjuvant or vaccine comprising same or of kits comprising same for the preparation of a medicament for the prophylaxis, treatment and/or amelioration of various diseases as defined herein, particularly prophylaxis, treatment and/or amelioration of such diseases as defined herein. Preferably, the pharmaceutical composition, an immunostimulating agent, an adjuvant or a vaccine is used or administered to a patient in need thereof for this purpose.

Preferably, diseases as mentioned herein are selected from cancer or tumour diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases, neuronal diseases or any disease which can be influenced by the present invention.

Such diseases include cancer or tumor diseases, preferably selected from melanomas, malignant melanomas, colon carcinomas, lymphomas, sarcomas, blastomas, renal carcinomas, gastrointestinal tumors, gliomas, prostate tumors, bladder cancer, rectal tumors, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, various virus-induced tumors such as, for example, papilloma virus-induced carcinomas (e.g. cervical carcinoma=cervical cancer), adenocarcinomas, herpes virus-induced tumors (e.g. Burkitt's lymphoma, EBV-induced B-cell lymphoma), hepatitis B-induced tumors (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal carcinoma (=Oesophageal cancer), wart involvement, tumors of the small intestine, craniopharyngeomas, ovarian carcinoma, genital tumors, ovarian cancer (=ovarian carcinoma), pancreatic carcinoma (=pancreatic cancer), endometrial carcinoma, liver metastases, penile cancer, tongue cancer, gall bladder cancer, leukaemia, plasmocytoma, lid tumor, prostate cancer (=prostate tumors), etc.

According to one further specific embodiment, diseases as defined herein comprise infectious diseases, preferably (viral, bacterial or protozoological) infectious diseases. Such infectious diseases, preferably to (viral, bacterial or protozoological) infectious diseases, are typically selected from influenza, malaria, SARS, yellow fever, AIDS, Lyme borreliosis, Leishmaniasis, anthrax, meningitis, viral infectious diseases such as AIDS, Condyloma acuminata, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, measles, foot-and-mouth disease, mononucleosis, mumps, Norwalk virus infection, Pfeiffer's glandular fever, smallpox, polio (childhood lameness), pseudo-croup, fifth disease, rabies, warts, West Nile fever, chickenpox, cytomegalic virus (CMV), bacterial infectious diseases such as miscarriage (prostate inflammation), anthrax, appendicitis, borreliosis, botulism, Camphylobacter, *Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella paratyphus, Salmonella typhus*, scarlet fever, syphilis, tetanus, tripper, tsutsugamushi disease, tuberculosis, typhus, vaginitis (colpitis), soft chancre, and infectious diseases caused by parasites, protozoa or fungi, such as amoebiasis, bilharziosis, Chagas disease, Echinococcus, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

According to another specific embodiment, diseases as defined herein comprise autoimmune diseases as defined in the following. Autoimmune diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjögren's syndrome, Scleroderma, Rheumatoid Arthritis and polymyositis or local syndromes which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus Type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T-Cell bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to the β-subunit of T-cell receptors in a non-specific fashion. Another explanation deduces autoimmune diseases from a Molecular Mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of rheumatic fever.

Additionally, according to one further specific embodiment, diseases as defined herein comprise allergies or allergic diseases, i.e. diseases related to allergies. Allergy is a condition that typically involves an abnormal, acquired immunological hypersensitivity to certain foreign antigens or allergens, such as the allergy antigens as defined herein. Such allergy antigens or allergens may be selected from allergy antigens as defined herein antigens derived from different sources, e.g. from animals, plants, fungi, bacteria, etc. Allergens in this context include e.g. grasses, pollens, molds, drugs, or numerous environmental triggers, etc. Allergies normally result in a local or systemic inflammatory response to these antigens or allergens and lead to immunity in the body against these allergens. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, allergic asthma (leading to swelling of the nasal mucosa), allergic conjunctivitis (leading to redness and itching of the conjunctiva), allergic rhinitis ("hay fever"), anaphylaxis, angiodema, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. Treatment of such allergic disorders or diseases may occur preferably by desensitizing the immune reaction which triggers a specific immune response. Such a desensitizing may be carried out by administering an effective amount of the allergen or allergic antigen encoded by the nucleic acid as defined herein, preferably, when formulated as a pharmaceutical composition, to induce a slight immune reaction. The amount of the allergen or allergic antigen may then be raised step by step in subsequent administrations until the immune system of the patient to be treated tolerates a specific amount of allergen or allergic antigen.

Additionally, diseases to be treated in the context of the present invention likewise include (hereditary) diseases, or genetic diseases in general monogenetic diseases, i.e. (hereditary) diseases, or genetic diseases in general. Such (mono-)genetic diseases, (hereditary) diseases, or genetic diseases in general are typically caused by genetic defects, e.g. due to gene mutations resulting in loss of protein activity or regulatory mutations which do not allow transcription or translation of the protein. Frequently, these diseases lead to metabolic disorders or other symptoms, e.g. muscle dystrophy. The present invention allows treating the following (hereditary) diseases or genetic diseases: 3-beta-hydroxysteroid dehydrogenase deficiency (type II); 3-ketothiolase deficiency; 6-mercaptopurine sensitivity; Aarskog-Scott syndrome; Abetalipoproteinemia; Acatalasemia; Achondrogenesis; Achondrogenesis-hypochondrogenesis; Achondroplasia; Achromatopsia; Acromesomelic dysplasia (Hunter-Thompson type); ACTH deficiency; Acyl-CoA dehydrogenase deficiency (short-chain, medium chain, long chain); Adenomatous polyposis coli; Adenosin-deaminase deficiency; Adenylosuccinase deficiency; Adhalinopathy;

Adrenal hyperplasia, congenital (due to 11-beta-hydroxylase deficiency; due to 17-alpha-hydroxylase deficiency; due to 21-hydroxylase deficiency); Adrenal hypoplasia, congenital, with hypogonadotropic hypogonadism; Adrenogenital syndrom; Adrenoleukodystrophy; Adrenomyeloneuropathy; Afibrinogenemia; Agammaglobulinemia; Alagille syndrome; Albinism (brown, ocular, oculocutaneous, rufous); Alcohol intolerance, acute; Aldolase A deficiency; Aldosteronism, glucocorticoid-remediable; Alexander disease; Alkaptonuria; Alopecia universalis; Alpha-1-antichymotrypsin deficiency; Alpha-methylacyl-CoA racemase deficiency; Alpha-thalassemia/mental retardation syndrome; Alport syndrome; Alzheimer disease-1 (APP-related); Alzheimer disease-3; Alzheimer disease-4; Amelogenesis imperfecta; Amyloid neuropathy (familial, several allelic types); Amyloidosis (Dutch type; Finnish type; hereditary renal; renal; senile systemic); Amytrophic lateral sclerosis; Analbuminemia; Androgen insensitivity; Anemia (Diamond-Blackfan); Anemia (hemolytic, due to PK deficiency); Anemia (hemolytic, Rh-null, suppressor type); Anemia (neonatal hemolytic, fatal and nearfatal); Anemia (sideroblastic, with ataxia); Anemia (sideroblastic/hypochromic); Anemia due to G6PD deficiency; Aneurysm (familial arterial); Angelman syndrome; Angioedema; Aniridia; Anterior segment anomalies and cataract; Anterior segment mesenchymal dysgenesis; Anterior segment mesenchymal dysgenesis and cataract; Antithrombin III deficiency; Anxiety-related personality traits; Apert syndrome; Apnea (postanesthetic); ApoA-I and apoC-III deficiency (combined); Apolipoprotein A-II deficiency; Apolipoprotein B-100 (ligand-defective); Apparent mineralocorticoid excess (hypertension due to); Argininemia; Argininosuccinicaciduria; Arthropathy (progressive pseudorheumatoid, of childhood); Aspartylglucosaminuria; Ataxia (episodic); Ataxia with isolated vitamin E deficiency; Ataxia-telangiectasia; Atelosteogenesis II; ATP-dependent DNA ligase I deficiency; Atrial septal defect with atrioventricular conduction defects; Atrichia with papular lesions; Autism (succinylpurinemic); Autoimmune polyglandular disease, type I; Autonomic nervous system dysfunction; Axenfeld anomaly; Azoospermia; Bamforth-Lazarus syndrome; Bannayan-Zonana syndrome; Barthsyndrome; Bartter syndrome (type 2 or type 3); Basal cell carcinoma; Basal cell nevus syndrome; BCG infection; Beare-Stevenson cutis gyrata syndrome; Becker muscular dystrophy; Beckwith-Wiedemann syndrome; Bernard-Soulier syndrome (type B; type C); Bethlem myopathy; Bile acid malabsorption, primary; Biotimidase deficiency; Bladder cancer; Bleeding disorder due to defective thromboxane A2 receptor; Bloom syndrome; Brachydactyl) (type B1 or type C); Branchiootic syndrome; Branchiootorenal syndrome; Breast cancer (invasive intraductal; lobular; male, with Reifenstein syndrome; sporadic); Breast cancer-1 (early onset); Breast cancer-2 (early onset); Brody myopathy; Brugada syndrome; Brunner syndrome; Burkitt lymphoma; Butterfly dystrophy (retinal); Ciq deficiency (type A; type B; type C); C1r/C1s deficiency; C1s deficiency, isolated; C2 deficiency; C3 deficiency; Cab inactivator deficiency; C4 deficiency; C8 deficiency, type II; C9 deficiency; Campomelic dysplasia with autosomal sex reversal; Camptodactyl)-arthropathy-coxa varapericarditis syndrome; Canavan disease; Carbamoylphosphate synthetase I deficiency; Carbohydrate-deficient glycoprotein syndrome (type I; type Ib; type II); Carcinoid tumor of lung; Cardioencephalomyopathy (fatal infantile, due to cytochrome c oxidase deficiency); Cardiomyopathy (dilated; X-linked dilated; familial hypertrophic; hypertrophic); Carnitine deficiency (systemic primary); Carnitine-acylcarnitine translocase deficiency; Carpal tunnel syndrome (familial); Cataract (cerulean; congenital; crystalline aculeiform; juvenile-onset; polymorphic and lamellar; punctate; zonular pulverulent); Cataract, Coppock-like; CD59 deficiency; Central core disease; Cerebellar ataxia; Cerebral amyloid angiopathy; Cerebral arteriopathy with subcortical infarcts and leukoencephalopathy; Cerebral cavernous malformations-1; Cerebrooculofacioskeletal syndrome; Cerebrotendinous xanthomatosis; Cerebrovascular disease; Ceroid lipofuscinosis (neuronal, variant juvenile type, with granular osmiophilic deposits); Ceroid lipofuscinosis (neuronal-1, infantile); Ceroid-lipofuscinosis (neuronal-3, juvenile); Char syndrome; Charcot-Marie-Tooth disease; Charcot-Marie-Tooth neuropathy; Charlevoix-Saguenay type; Chediak-Higashi syndrome; Chloride diarrhea (Finnish type); Cholestasis (benign recurrent intrahepatic); Cholestasis (familial intrahepatic); Cholestasis (progressive familial intrahepatic); Cholesteryl ester storage disease; Chondrodysplasia punctata (brachytelephalangic; rhizomelic; X-linked dominant; X-linked recessive; Grebe type); Chondrosarcoma; Choroideremia; Chronic granulomatous disease (autosomal, due to deficiency of CYBA); Chronic granulomatous disease (X-linked); Chronic granulomatous disease due to deficiency of NCF-1; Chronic granulomatous disease due to deficiency of NCF-2; Chylomicronemia syndrome, familial; Citrullinemia; classical Cockayne syndrome-1; Cleft lip, cleft jaw, cleft palate; Cleft lip/palate ectodermal dysplasia syndrome; Cleidocranial dysplasia; CMO II deficiency; Coats disease; Cockayne syndrome-2, type B; Coffin-Lowry syndrome; Colchicine resistance; Colon adenocarcinoma; Colon cancer; Colorblindness (deutan; protan; tritan); Colorectal cancer; Combined factor V and VIII deficiency; Combined hyperlipemia (familial); Combined immunodeficiency (X-linked, moderate); Complex I deficiency; Complex neurologic disorder; Cone dystrophy-3; Cone-rod dystrophy 3; Cone-rod dystrophy 6; Cone-rod retinal dystrophy-2; Congenital bilateral absence of vas deferens; Conjunctivitis, ligneous; Contractural arachnodactyly; Coproporphyria; Cornea plana congenita; Corneal clouding; Corneal dystrophy (Avellino type; gelatinous drop-like; Groenouw type I; lattice type I; Reis-Bucklers type); Cortisol resistance; Coumarin resistance; Cowden disease; CPT deficiency, hepatic (type I; type II); Cramps (familial, potassium-aggravated); Craniofacial-deafness-hand syndrome; Craniosynostosis (type 2); Cretinism; Creutzfeldt-Jakob disease; Crigler-Najjar syndrome; Crouzon syndrome; Currarino syndrome; Cutis laxa; Cyclic hematopoiesis; Cyclic ichthyosis; Cylindromatosis; Cystic fibrosis; Cystinosis (nephropathic); Cystinuria (type II; type III); Daltonism; Darier disease; D-bifunctional protein deficiency; Deafness, autosomal dominant 1; Deafness, autosomal dominant 1; Deafness, autosomal dominant 12; Deafness, autosomal dominant 15; Deafness, autosomal dominant 2; Deafness, autosomal dominant 3; Deafness, autosomal dominant 5; Deafness, autosomal dominant 8; Deafness, autosomal dominant 9; Deafness, autosomal recessive 1; Deafness, autosomal recessive 2; Deafness, autosomal recessive 21; Deafness, autosomal recessive 3; Deafness, autosomal recessive 4; Deafness, autosomal recessive 9; Deafness, nonsyndromic sensorineural 13; Deafness, X-linked 1; Deafness, X-linked 3; Debrisoquine sensitivity; Dejerine-Sottas disease; Dementia (familial Danish); Dementia (frontotemporal, with parkinsonism); Dent disease; Dental anomalies; Dentatorubro-pallidoluysian atrophy; Denys-Drash syndrome; Dermatofibrosarcoma protuberans; Desmoid disease; Diabetes insipidus (nephrogenic); Diabetes insipidus (neurohypophyseal); Diabetes mellitus (insulin-resistant); Diabetes mellitus (rare form); Diabetes mellitus (type II); Diastrophic dysplasia; Dihydropyrimidinuria; Dosage-sensitive sex reversal; Doyne honeycomb degeneration of retina; Dubin-Johnson syndrome; Duchenne muscular dystrophy; Dyserythropoietic anemia with thrombocytopenia; Dysfibrinogenemia (alpha type; beta type; gamma type); Dyskeratosis congenita-1; Dysprothrombinemia; Dystonia (DOPAresponsive); Dystonia (myoclonic); Dystonia-1 (torsion); Ectodermal dysplasia; Ectopia lentis; Ectopia pupillae; Ectrodactyly (ectodermal dysplasia, and cleft lip/palate syndrome 3); Ehlers-Danlos syndrome (progeroid form); Ehlers-Danlos syndrome (type I; type II; type III; type IV; type VI; type VII); Elastin Supravalvar aortic stenosis; Elliptocytosis-1; Elliptocytosis-2; Elliptocytosis-3; Ellis-van Creveld syndrome; Emery-Dreifuss muscular dystrophy; Emphysema; Encephalopathy; Endocardial fibroelastosis-2; Endometrial carcinoma; Endplate acetylcholinesterase deficiency; Enhanced S-cone syndrome; Enlarged vestibular aqueduct; Epidermolysis bullosa; Epidermolysis bullosa dystrophica (dominant or recessive); Epidermolysis bullosa simplex; Epidermolytic hyperkeratosis; Epidermolytic palmoplantar keratoderma; Epilepsy (generalize; juvenile; myoclonic; nocturnal frontal lobe; progressive myoclonic); Epilepsy, benign, neonatal (type1 or type2); Epiphyseal dysplasia (multiple); Episodic ataxia (type 2); Episodic ataxia/myokymia syndrome; Erythremias (alpha-; dysplasia); Erythrocytosis; Erythrokeratoderma; Estrogen resistance; Exertional myoglobinuria due to deficiency of LDH-A; Exostoses, multiple (type 1; type 2); Exudative vitreoretinopathy, X-linked; Fabry disease; Factor H deficiency; Factor VII deficiency; Factor X deficiency; Factor XI deficiency; Factor XII deficiency; Factor XIIIA deficiency; Factor XIIIB deficiency; Familial Mediterranean fever; Fanconi anemia; Fanconi-Bickel syndrome; Farber lipogranulomatosis; Fatty liver (acute); Favism; Fish-eye disease; Foveal hypoplasia; Fragile X syndrome; Frasier syndrome; Friedreich ataxia; fructose-bisphosphatase Fructose intolerance; Fucosidosis; Fumarase deficiency; Fundus albipunctatus; Fundus flavimaculatus; G6PD deficiency; GABA-transaminase deficiency; Galactokinase deficiency with cataracts; Galactose epimerase deficiency; Galactosemia; Galactosialidosis; GAMT deficiency; Gardner syndrome; Gastric cancer; Gaucher disease; Generalized epilepsy with febrile seizures plus; Germ cell tumors; Gerstmann-Straussler disease; Giant cell hepatitis (neonatal); Giant platelet disorder; Giant-cell fibroblastoma; Gitelman syndrome; Glanzmann thrombasthenia (type A; type B); Glaucoma 1A; Glaucoma 3A; Glioblastoma multiforme; Glomerulosclerosis (focal segmental); Glucose transport defect (blood-brain barrier); Glucose/galactose malabsorption; Glucosidase I deficiency; Glutaricaciduria (type I; type IIB; type IIC); Gluthation synthetase deficiency; Glycerol kinase deficiency; Glycine receptor (alpha-1 polypeptide); Glycogen storage disease I; Glycogen storage disease II; Glycogen storage disease III; Glycogen storage disease IV; Glycogen storage disease VI; Glycogen storage disease VII; Glycogenosis (hepatic, autosomal); Glycogenosis (X-linked hepatic); GM1-gangliosidosis; GM2-gangliosidosis; Goiter (adolescent multinodular); Goiter (congenital); Goiter (nonendemic, simple); Gonadal dysgenesis (XY type); Granulomatosis, septic; Graves disease; Greig cephalopolysyndactyly syndrome; Griscelli syndrome; Growth hormone deficient dwarfism; Growth retardation with deafness and mental retardation; Gynecomastia (familial, due to increased aromatase activity); Gyrate atrophy of choroid and retina with ornithinemia (B6 responsive or unresponsive); Hailey-Hailey disease; Haim-Munk syndrome; Hand-foot-uterus syndrome; Harderoporphyrinuria; HDL deficiency (familial); Heart block (nonprogressive or progressive); Heinz body anemia; HELLP syndrome; Hematuria (familial benign); Heme oxygenase-1 deficiency; Hemiplegic migraine; Hemochromotosis; Hemoglobin H disease; Hemolytic anemia due to ADA excess; Hemolytic anemia due to adenylate kinase deficiency; Hemolytic anemia due to band 3 defect; Hemolytic anemia due to glucosephosphate isomerase deficiency; Hemolytic anemia due to glutathione synthetase deficiency; Hemolytic anemia due to hexokinase deficiency; Hemolytic anemia due to PGK deficiency; Hemolytic-uremic syndrome; Hemophagocytic lymphohistiocytosis; Hemophilia A; Hemophilia B; Hemorrhagic diathesis due to factor V deficiency; Hemosiderosis (systemic, due to aceruloplasminemia); Hepatic lipase deficiency; Hepatoblastoma; Hepatocellular carcinoma; Hereditary hemorrhagic telangiectasia-1; Hereditary hemorrhagic telangiectasia-2; Hermansky-Pudlak syndrome; Heterotaxy (X-linked visceral); Heterotopia (periventricular); Hippel-Lindau syndrom; Hirschsprung disease; Histidine-rich glycoprotein Thrombophilia due to HRG deficiency; HMG-CoA lyase deficiency; Holoprosencephaly-2; Holoprosencephaly-3; Holoprosencephaly-4; Holoprosencephaly-5; Holt-Oram syndrome; Homocystinuria; Hoyeraal-Hreidarsson; HPFH (deletion type or nondeletion type); HPRT-related gout; Huntington disease; Hydrocephalus due to aqueductal stenosis; Hydrops fetalis; Hyperbetalipoproteinemia; Hypercholesterolemia, familial; Hyperferritinemia-cataract syndrome; Hyperglycerolemia; Hyperglycinemia; Hyperimmunoglobulinemia D and periodic fever syndrome; Hyperinsulinism; Hyperinsulinism-hyperammonemia syndrome; Hyperkalemic periodic paralysis; Hyperlipoproteinemia; Hyperlysinemia; Hypermethioninemia (persistent, autosomal, dominant, due to methionine, adenosyltransferase I/III deficiency); Hyperornithinemia-hyperammonemiahomocitrullinemia syndrome; Hyperoxaluria; Hyperparathyroidism; Hyperphenylalaninemia due to pterin-4-acarbinolamine dehydratase deficiency; Hyperproinsulinemia; Hyperprolinemia; Hypertension; Hyperthroidism (congenital); Hypertriglyceridemia; Hypoalphalipoproteinemia; Hypobetalipoproteinemia; Hypocalcemia; Hypochondroplasia; Hypochromic microcytic anemia; Hypodontia; Hypofibrinogenemia; Hypoglobulinemia and absent B cells; Hypogonadism (hypergonadotropic); Hypogonadotropic (hypogonadism); Hypokalemic periodic paralysis; Hypomagnesemia; Hypomyelination (congenital); Hypoparathyroidism; Hypophosphatasia (adult; childhood; infantile; hereditary); Hypoprothrombinemia; Hypothyroidism (congenital; hereditary congenital; nongoitrous); Ichthyosiform erythroderma; Ichthyosis; Ichthyosis bullosa of Siemens; IgG2 deficiency; Immotile cilia syndrome-1; Immunodeficiency (T-cell receptor/CD3 complex); Immunodeficiency (X-linked, with hyper-IgM); Immunodeficiency due to defect in CD3-gamma; Immunodeficiency-centromeric instabilityfacial anomalies syndrome; Incontinentia pigmenti; Insensitivity to pain (congenital, with anhidrosis); Insomnia (fatal familial); Interleukin-2 receptor deficiency (alpha chain); Intervertebral disc disease; Iridogoniodysgenesis; Isolated growth hormone deficiency (Illig type with absent GH and Kowarski type with bioinactive GH); Isovalericacidemia; Jackson-Weiss sydnrome; Jensen syndrome; Jervell and Lange-Nielsen syndrome; Joubert syndrom; Juberg-Marsidi syndrome; Kallmann syndrome; Kanzaki disease; Keratitis; Keratoderma (palmoplantar); Keratosis palmoplantaris striata I; Keratosis palmoplantaris striata II; Ketoacidosis due to SCOT deficiency; Keutel syndrome; Klippel-Trenaurnay syndrom; Kniest dysplasia; Kostmann neutropenia; Krabbe disease; Kurzripp-Polydaktylie syndrom; Lacticacidemia due to PDX1 deficiency; Langer mesomelic dysplasia; Laron dwarfism; Laurence-Moon-Biedl-Bardet syndrom; LCHAD deficiency; Leber congenital amaurosis; Left-right axis malformation; Leigh syndrome; Leiomyomatosis (diffuse, with Alport syndrome); Leprechaunism; Leri-Weill dyschondrosteosis; Lesch-Nyhan syndrome; Leukemia (acute myeloid; acute promyelocytic; acute T-cell lymphoblastic; chronic myeloid; juvenile myelomonocytic; Leukemia-1 (T-cell acute lymphocytic); Leukocyte adhesion deficiency; Leydig cell adenoma; Lhermitte-Duclos syndrome; Liddle syndrome; Li-Fraumeni syndrome; Lipoamide dehydrogenase deficiency; Lipodystrophy; Lipoid adrenal hyperplasia; Lipoprotein lipase deficiency; Lissencephaly (X-linked); Lissencephaly-1; liver Glycogen storage disease (type o); Long QT syndrome-1; Long QT syndrome-2; Long QT syndrome-3; Long QT syndrome-5; Long QT syndrome-6; Lowe syndrome; Lung cancer; Lung cancer (nonsmall cell); Lung cancer (small cell); Lymphedema; Lymphoma (B-cell non-Hodgkin); Lymphoma (diffuse large cell); Lymphoma (follicular); Lymphoma (MALT); Lymphoma (mantel cell); Lymphoproliferative syndrome (X-linked); Lysinuric protein intolerance; Machado-Joseph disease; Macrocytic anemia refractory (of 5q syndrome); Macular dystrophy; Malignant mesothelioma; Malonyl-CoA decarboxylase deficiency; Mannosidosis, (alpha- or beta-); Maple syrup urine disease (type Ia; type Ib; type II); Marfan syndrome; Maroteaux-Lamy syndrome; Marshall syndrome; MASA syndrome; Mast cell leukemia; Mastocytosis with associated hematologic disorder; McArdle disease; McCune-Albright polyostotic fibrous dysplasia; McKusick-Kaufman syndrome; McLeod phenotype; Medullary thyroid carcinoma; Medulloblastoma; Meesmann corneal dystrophy; Megaloblastic anemia-1; Melanoma; Membroproliferative glomerulonephritis; Meniere disease; Meningioma (NF2-related; SIS-related); Menkes disease; Mental retardation (X-linked); Mephenyloin poor metabolizer; Mesothelioma; Metachromatic leukodystrophy; Metaphyseal chondrodysplasia (Murk Jansen type; Schmid type); Methemoglobinemia; Methionine adenosyltransferase deficiency (autosomal recessive); Methylcobalamin deficiency (cbl G type); Methylmalonicaciduria (mutase deficiency type); Mevalonicaciduria; MHC class II deficiency; Microphthalmia (cataracts, and iris abnormalities); Miyoshi myopathy; MODY; Mohr-Tranebjaerg syndrome; Molybdenum cofactor deficiency (type A or type B); Monilethrix; Morbus Fabry; Morbus Gaucher; Mucopolysaccharidosis; Mucoviscidosis; Muencke syndrome; Muir-Torre syndrome; Mulibrey nanism; Multiple carboxylase deficiency (biotinresponsive); Multiple endocrine neoplasia; Muscle glycogenosis; Muscular dystrophy (congenital merosindeficient); Muscular dystrophy (Fukuyama congenital); Muscular dystrophy (limb-girdle); Muscular dystrophy) Duchenne-like); Muscular dystrophy with epidermolysis bullosa simplex; Myasthenic syndrome (slow-channel congenital); Mycobacterial infection (atypical, familial disseminated); Myelodysplastic syndrome; Myelogenous leukemia; Myeloid malignancy; Myeloperoxidase deficiency; Myoadenylate deaminase deficiency; Myoglobinuria/hemolysis due to PGK deficiency; Myoneurogastrointestinal encephalomyopathy syndrome; Myopathy (actin; congenital; desmin-related; cardioskeletal; distal; nemaline); Myopathy due to CPT II deficiency; Myopathy due to phosphoglycerate mutase deficiency; Myotonia congenita; Myotonia levior; Myotonic dystrophy; Myxoid liposarcoma; NAGA deficiency; Nailpatella syndrome; Nemaline myopathy 1 (autosomal dominant); Nemaline myopathy 2 (autosomal recessive); Neonatal hyperparathyroidism; Nephrolithiasis; Nephronophthisis (juvenile); Nephropathy (chronic hypocomplementemic); Nephrosis-1; Nephrotic syndrome; Netherton syndrome; Neuroblastoma; Neurofibromatosis (type 1 or type 2); Neurolemmomatosis; neuronal-5 Ceroid-lipofuscinosis; Neuropathy; Neutropenia (alloimmune neonatal); Niemann-Pick disease (type A; type B; type C1; type D); Night blindness (congenital stationary); Nijmegen breakage syndrome; Noncompaction of left ventricular myocardium; Nonepidermolytic palmoplantar keratoderma; Norrie disease; Norum disease; Nucleoside phosphorylase deficiency; Obesity; Occipital hornsyndrome; Ocular albinism (Nettleship-Falls type); Oculopharyngeal muscular dystrophy; Oguchi disease; Oligodontia; Omenn syndrome; Opitz G syndrome; Optic nerve coloboma with renal disease; Ornithine transcarbamylase deficiency; Oroticaciduria; Orthostatic intolerance; OSMED syndrome; Ossification of posterior longitudinal ligament of spine; Osteoarthrosis; Osteogenesis imperfecta; Osteolysis; Osteopetrosis (recessive or idiopathic); Osteosarcoma; Ovarian carcinoma; Ovarian dysgenesis; Pachyonychia congenita (Jackson-Lawler type or Jadassohn-Lewandowsky type); Paget disease of bone; Pallister-Hall syndrome; Pancreatic agenesis; Pancreatic cancer; Pancreatitis; Papillon-Lefevre syndrome; Paragangliomas; Paramyotonia congenita; Parietal foramina; Parkinson disease (familial or juvenile); Paroxysmal nocturnal hemoglobinuria; Pelizaeus-Merzbacher disease; Pendred syndrome; Perineal hypospadias; Periodic fever; Peroxisomal biogenesis disorder; Persistent hyperinsulinemic hypoglycemia of infancy; Persistent Mullerian duct syndrome (type II); Peters anomaly; Peutz-Jeghers syndrome; Pfeiffer syndrome; Phenylketonuria; Phosphoribosyl pyrophosphate synthetaser-elated gout; Phosphorylase kinase deficiency of liver and muscle; Piebaldism; Pilomatricoma; Pinealoma with bilateral retinoblastoma; Pituitary ACTH secreting adenoma; Pituitary hormone deficiency; Pituitary tumor; Placental steroid sulfatase deficiency; Plasmin inhibitor deficiency; Plasminogen deficiency (types I and II); Plasminogen Tochigi disease; Platelet disorder; Platelet glycoprotein IV deficiency; Platelet-activating factor acetylhydrolase deficiency; Polycystic kidney disease; Polycystic lipomembranous osteodysplasia with sclerosing leukenencephalophathy; Polydactyl), postaxial; Polyposis; Popliteal pterygium syndrome; Porphyria (acute hepatic or acute intermittent or congenital erythropoietic); Porphyria cutanea tarda; Porphyria hepatoerythropoietic; Porphyria variegata; Prader-Willi syndrome; Precocious puberty; Premature ovarian failure; Progeria Typ I; Progeria Typ II; Progressive external ophthalmoplegia; Progressive intrahepatic cholestasis-2; Prolactinoma (hyperparathyroidism, carcinoid syndrome); Prolidase deficiency; Propionicacidemia; Prostate cancer; Protein S deficiency; Proteinuria; Protoporphyria (erythropoietic); Pseudoachondroplasia; Pseudohermaphroditism; Pseudohypoaldosteronism; Pseudohypoparathyroidism; Pseudovaginal perineoscrotal hypospadias; Pseudovitamin D deficiency rickets; Pseudoxanthoma elasticum (autosomal dominant; autosomal recessive); Pulmonary alveolar proteinosis; Pulmonary hypertension; Purpura fulminans; Pycnodysostosis; Pyropoikilocytosis; Pyruvate carboxylase deficiency; Pyruvate dehydrogenase deficiency; Rabson-Mendenhall syndrome; Refsum disease; Renal cell carcinoma; Renal tubular acidosis; Renal tubular acidosis with deafness; Renal tubular acidosis-osteopetrosis syndrome; Reticulosis (familial histiocytic); Retinal degeneration; Retinal dystrophy; Retinitis pigmentosa; Retinitis punctata albescens; Retinoblastoma; Retinol binding protein deficiency; Retinoschisis; Rett syndrome; Rh(mod) syndrome; Rhabdoid predisposition syndrome; Rhabdoid tumors; Rhabdomyosarcoma; Rhabdomyosarcoma (alveolar); Rhizomelic chondrodysplasia punctata; Ribbing-Syndrom; Rickets (vitamin D-resistant); Rieger anomaly; Robinow syndrome; Rothmund-Thomson syndrome; Rubenstein-Taybi syndrome; Saccharopinuria; Saethre-Chotzen syndrome; Salla disease; Sandhoff disease (infantile, juvenile, and adult forms); Sanfilippo syndrome (type A or type B); Schindler disease; Schizencephaly; Schizophrenia (chronic); Schwannoma (sporadic); SCID (autosomal recessive, T-negative/Bpositive type); Secretory pathway w/TMD; SED congenita; Segawa syndrome; Selective T-cell defect; SEMD (Pakistani type); SEMD (Strudwick type); Septooptic dysplasia; Severe combined immunodeficiency (B cellnegative); Severe combined immunodeficiency (T-cell negative, B-cell/natural killer cell-positive type); Severe combined immunodeficiency (Xlinked); Severe combined immunodeficiency due to ADA deficiency; Sex reversal (XY, with adrenal failure); Sezary syndrome; Shah-Waardenburg syndrome; Short stature; Shprintzen-Goldberg syndrome; Sialic acid storage disorder; Sialidosis (type I or type II); Sialuria; Sickle cell anemia; Simpson-Golabi-Behmel syndrome; Situs ambiguus; Sjogren-Larsson syndrome; Smith-Fineman-Myers syndrome; Smith-Lemli-Opitz syndrome (type I or type II); Somatotrophinoma; Sorsby fundus dystrophy; Spastic paraplegia; Spherocytosis; Spherocytosis-1; Spherocytosis-2; Spinal and bulbar muscular atrophy of Kennedy; Spinal muscular atrophy; Spinocerebellar ataxia; Spondylocostal dysostosis; Spondyloepiphyseal dysplasia tarda; Spondylometaphyseal dysplasia (Japanese type); Stargardt disease-1; Steatocystoma multiplex; Stickler syndrome; Sturge-Weber syndrom; Subcortical laminal heteropia; Subcortical laminar heterotopia; Succinic semialdehyde dehydrogenase deficiency; Sucrose intolerance; Sutherland-Haan syndrome; Sweat chloride elevation without CF; Symphalangism; Synostoses syndrome; Synpolydactyly; Tangier disease; Tay-Sachs disease; T-cell acute lymphoblastic leukemia; T-cell immunodeficiency; T-cell prolymphocytic leukemia; Thalassemia (alpha- or delta-); Thalassemia due to Hb Lepore; Thanatophoric dysplasia (types I or II); Thiamine-responsive megaloblastic anemia syndrome; Thrombocythemia; Thrombophilia (dysplasminogenemic); Thrombophilia due to heparin cofactor II deficiency; Thrombophilia due to protein C deficiency; Thrombophilia due to thrombomodulin defect; Thyroid adenoma; Thyroid hormone resistance; Thyroid iodine peroxidase deficiency; Tietz syndrome; Tolbutamide poor metabolizer; Townes-Brocks syndrome; Transcobalamin II deficiency; Treacher Collins mandibulofacial dysostosis; Trichodontoosseous syndrome; Trichorhinophalangeal syndrome; Trichothiodystrophy; Trifunctional protein deficiency (type I or type II); Trypsinogen deficiency; Tuberous sclerosis-1; Tuberous sclerosis-2; Turcot syndrome; Tyrosine phosphatase; Tyrosinemia; Ulnar-mammary syndrome; Urolithiasis (2,8-dihydroxyadenine); Usher syndrome (type 1B or type 2A); Venous malformations; Ventricular tachycardia; Virilization; Vitamin K-dependent coagulation defect; VLCAD deficiency; Vohwinkel syndrome; von Hippel-Lindau syndrome; von Willebrand disease; Waardenburg syndrome; Waardenburg syndrome/ocular albinism; Waardenburg-Shah neurologic variant; Waardenburg-Shah syndrome; Wagner syndrome; Warfarin sensitivity; Watson syndrome; Weissenbacher-Zweymuller syndrome; Werner syndrome; Weyers acrodental dysostosis; White sponge nevus; Williams-Beuren syndrome; Wilms tumor (types); Wilson disease; Wiskott-Aldrich syndrome; Wolcott-Rallison syndrome; Wolfram syndrome; Wolman disease; Xanthinuria (type I); Xeroderma pigmentosum; X-SCID; Yemenite deaf-blind hypopigmentation syndrome; ypocalciuric hypercalcemia (type I); Zellweger syndrome; Zlotogora-Ogur syndrome.

Diseases to be treated in the context of the present invention likewise also include diseases which have a genetic inherited background and which are typically caused by a single gene defect and are inherited according to Mendel's laws are preferably selected from the group consisting of autosomal-recessive inherited diseases, such as, for example, adenosine deaminase deficiency, familial hypercholesterolaemia, Canavan's syndrome, Gaucher's disease, Fanconi anaemia, neuronal ceroid lipofuscinoses, mucoviscidosis (cystic fibrosis), sickle cell anaemia, phenylketonuria, alcaptonuria, albinism, hypothyreosis, galactosaemia, alpha-1-anti-trypsin deficiency, Xeroderma pigmentosum, Ribbing's syndrome, mucopolysaccharidoses, cleft lip, jaw, palate, Laurence Moon Biedl Bardet sydrome, short rib polydactylia syndrome, cretinism, Joubert's syndrome, type II progeria, brachydactylia, adrenogenital syndrome, and X-chromosome inherited diseases, such as, for example, colour blindness, e.g. red/green blindness, fragile X syndrome, muscular dystrophy (Duchenne and Becker-Kiener type), haemophilia A and B, G6PD deficiency, Fabry's disease, mucopolysaccharidosis, Norrie's syndrome, Retinitis pigmentosa, septic granulomatosis, X-SCID, ornithine transcarbamylase deficiency, Lesch-Nyhan syndrome, or from autosomal-dominant inherited diseases, such as, for example, hereditary angiooedema, Marfan syndrome, neurofibromatosis, type I progeria, Osteogenesis imperfecta, Klippel-Trenaurnay syndrome, Sturge-Weber syndrome, Hippel-Lindau syndrome and tuberosis sclerosis.

The present invention also allows treatment of diseases, which have not been inherited, or which may not be summarized under the above categories. Such diseases may include e.g. the treatment of patients, which are in need of a specific protein factor, e.g. a specific therapeutically active protein as mentioned above. This may e.g. include dialysis patients, e.g. patients which undergo a (regular) a kidney or renal dialysis, and which may be in need of specific therapeutically active proteins as defined herein, e.g. erythropoietin (EPO), etc.

Likewise, diseases in the context of the present invention may include cardiovascular diseases chosen from, without being limited thereto, coronary heart disease, arteriosclerosis, apoplexy and hypertension, etc.

Finally, diseases in the context of the present invention may be chosen from neuronal diseases including e.g. Alzheimer's disease, amyotrophic lateral sclerosis, dystonia, epilepsy, multiple sclerosis and Parkinson's disease etc.

According to another embodiment, the present invention is directed to the second medical use of the inventive polymeric carrier cargo complex as defined herein, for the treatment of diseases as defined herein by means of gene therapy.

In a further preferred embodiment, the inventive polymeric carrier cargo complex may be used for the preparation of a pharmaceutical composition, an immunostimulating agent, an adjuvant or a vaccine.

The inventive pharmaceutical composition, immunostimulating agent, adjuvant or vaccine may furthermore be used for the treatment of a disease or a disorder as defined herein.

According to a final embodiment, the present invention also provides kits, particularly kits of parts, comprising as components alone or in combination with further ingredients at least one inventive polymeric carrier cargo complex as defined herein, at least one pharmaceutical composition, immunostimulating agent, adjuvant or vaccine comprising same and/or kits comprising same, and optionally technical instructions with information on the administration and dosage of the polymeric carrier molecule, the nucleic acid, the inventive polymeric carrier complex, and/or the inventive pharmaceutical composition. Such kits, preferably kits of parts, may be applied, e.g., for any of the above mentioned applications or uses. Such kits, when occurring as a kit of parts, may further contain each component of the inventive pharmaceutical composition, immunostimulating agent, adjuvant or vaccine in a different part of the kit.

In the present invention, if not otherwise indicated, different features of alternatives and embodiments may be combined with each other, where suitable. Furthermore, the term "comprising" shall not be construed as meaning "consisting of", if not specifically mentioned. However, in the context of the present invention, term "comprising" may be substituted with the term "consisting of", where suitable.

FIGURES

The following Figures are intended to illustrate the invention further. They are not intended to limit the subject matter of the invention thereto.

FIG. 1: shows the luciferase expression in HepG2 cells after transfection with polymeric carrier cargo complexes comprising 5 μg mRNA coding for luciferase (R1180). $CR_{12}C$/R1180 indicates the inventive polymeric carrier cargo complex formed by the disulfide-crosslinked cationic peptide $CR_{12}C$ (Cys-$Arg_{12}$-Cys) and the mRNA R1180 as nucleic acid cargo. $R_{12}$/R1180 indicates a non-inventive carrier cargo complex formed by the non-polymerizing cationic peptide $R_{12}$ ($Arg_{12}$) and the mRNA R1180 as nucleic acid cargo for the purpose of comparison.

The complexes contain cationic peptide and nucleic acid in a mass ratio at 1:2 (w/w) or 2:1 (w/w) as indicated.

R1180 represents cells which were transfected with uncomplexed RNA.

Buffer represents the negative control for non-transfected cells.

After 24 h the level of luciferase was quantified in the lysates by chemoluminescence measurement of luciferin oxidation.

Data points indicate individual biological replicates.

The results firstly show that the inventive polymeric carrier cargo complexes ($CR_{12}C$/R1180) induce higher levels of luciferase expression than the non-inventive carrier cargo complexes ($R_{12}$/R1180) with the non-polymerized peptide $R_{12}$. And secondly it could be shown that N/P ratios higher than 1 are advantageous for in vitro transfection.

Figure 2:
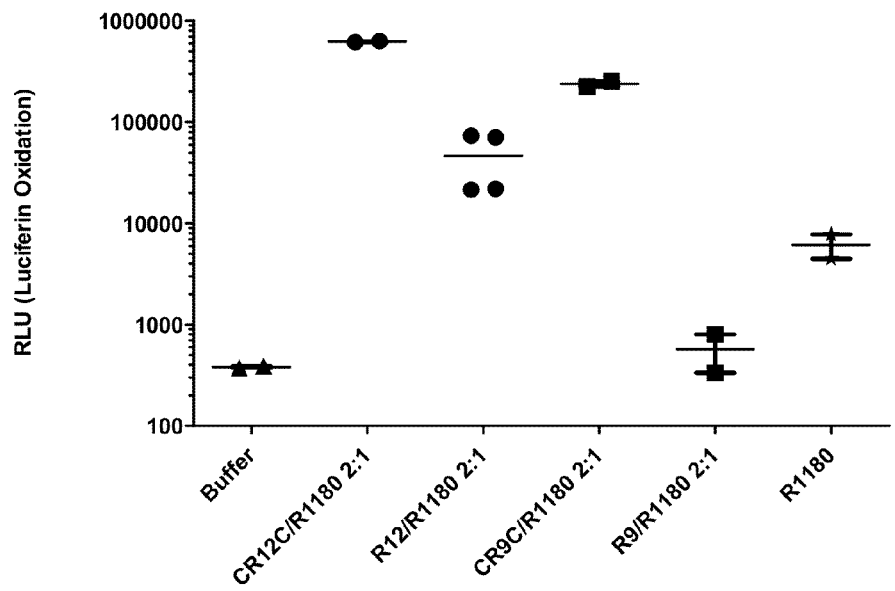
Figure 2:
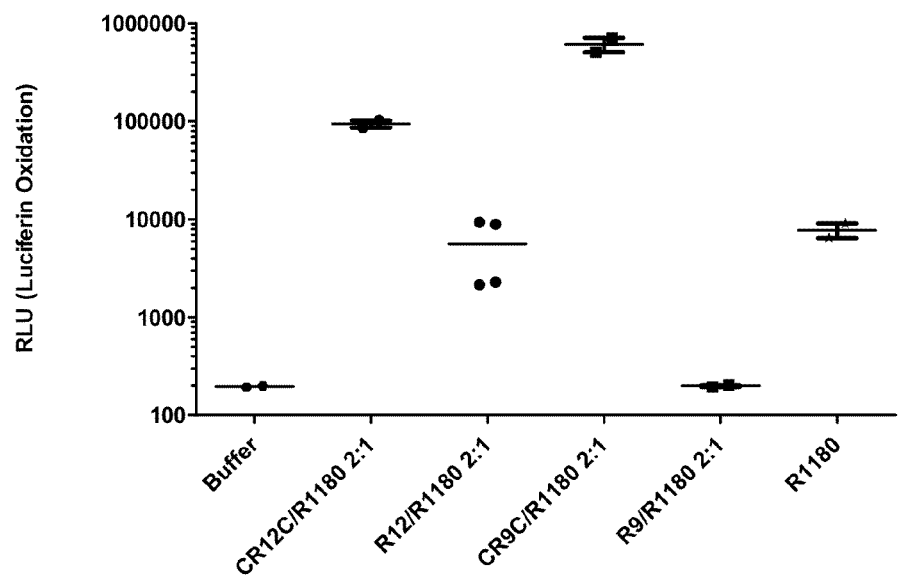

FIG. 2: shows the (in vitro) luciferase expression in HepG2 and B16F10 cells after transfection with polymeric carrier cargo complexes comprising 5 μg mRNA coding for luciferase (R1180). $CR_{12}C$/R1180 indicates the inventive polymeric carrier cargo complex formed by the disulfide cross-linked cationic peptide $CR_{12}C$ (Cys-$Arg_{12}$-Cys) and the mRNA R1180 as nucleic acid cargo. $R_{12}$/R1180 indicates a non-inventive carrier cargo complex formed by the non-polymerizing cationic peptide $R_{12}$ ($Arg_{12}$) and the mRNA R1180 as nucleic acid cargo for the purpose of comparison. $CR_9C$/R1180 indicates the inventive polymeric carrier cargo complex formed by the polymerized cationic peptide $CR_9C$ (Cys-$Arg_9$-Cys)

The complexes contain cationic peptide and nucleic acid in a mass ratio at 2:1 (w/w).

R1180 represents cells which were transfected with uncomplexed RNA.

Buffer represents the negative control for non-transfected cells.

After 24 h the level of luciferase was quantified in the lysates by chemoluminescence measurement of luciferin oxidation.

Data points indicate individual biological replicates.

The results show that the inventive polymeric carrier cargo complexes ($CR_{12}C$/R1180 and $CR_9C$/R1180) induce higher levels of luciferase expression than the non-inventive carrier cargo complexes ($R_{12}$/R1180 and $R_9$/1180) with the non-polymerized peptides $R_9$ and R.

Figure 3:
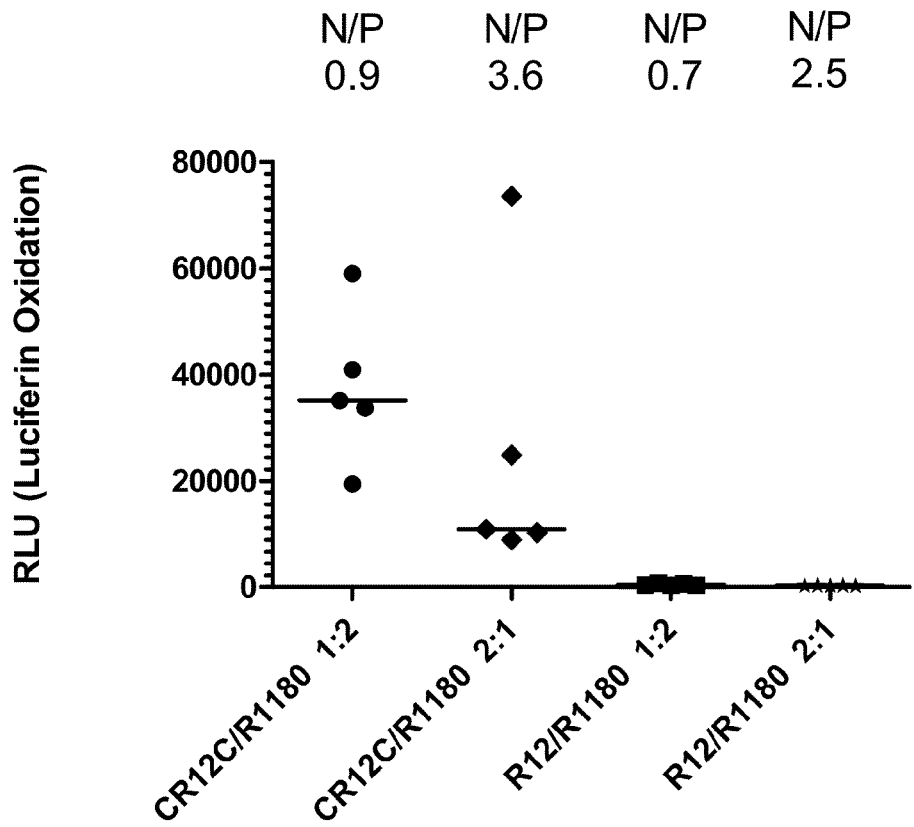

FIG. 3: shows the in vivo expression of luciferase after intradermal injection in female BALB/c mice of 5 μg mRNA coding for luciferase (R1180). $CR_{12}C$/R1180 indicates the inventive polymeric carrier cargo complex formed by the disulfide-crosslinked cationic peptide $CR_{12}C$ (Cys-Arg12-Cys) and the mRNA R1180 as nucleic acid cargo. $R_{12}$/R1180 indicates a non-inventive carrier cargo complex formed by the non-polymerizing cationic peptide R12 ($Arg_{12}$) and the mRNA R1180 as nucleic acid cargo for the purpose of comparison.

The complexes contain cationic peptide and nucleic acid in a ratio of 1:2 (w/w) or 2:1 as indicated.

After 24 h the level of luciferase was quantified in the tissue lysates by a chemoluminescence assay.

The results firstly show that the inventive polymeric carrier cargo complexes ($CR_{12}C$/R1180) induce higher levels of luciferase expression than the non-inventive carrier cargo complexes ($R_{12}$/R1180) with the non-polymerized peptide $R_{12}$ (in fact no luciferase expression in the sample with the non-polymerized peptide $R_{12}$ could be detected). And secondly it could be shown that N/P ratios below 1 are advantageous for in vivo transfection.

Figure 4:
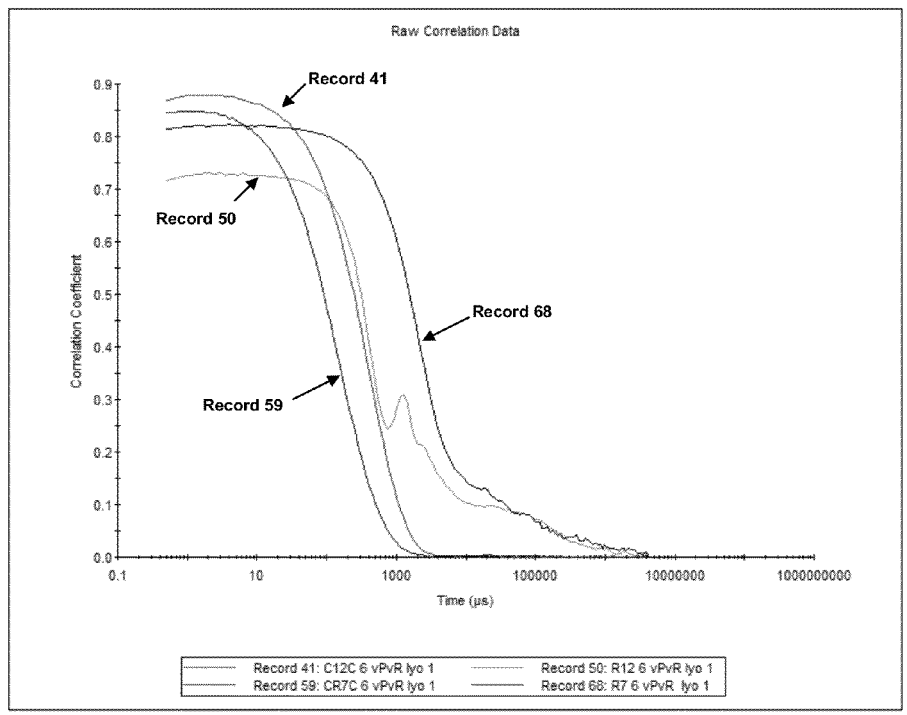

FIG. 4: shows the raw correlation curve of inventive polymeric carrier cargo complexes formed by the disulfide-crosslinked cationic peptides $CR_{12}C$ and $CR_7C$ as carrier after lyophilisation compared to non-inventive complexes with non-polymerizing cationic peptides as carrier ($R_{12}$ and $R_7$) by dynamic light scattering using a Zetasizer Nano (Malvern Instruments, Malvern, UK). The hydrodynamic diameters were measured with fresh prepared complexes and with reconstituted complexes after lyophilisation The mass ratio of peptide:RNA was 1:2. As result it can be shown that the inventive polymeric carrier cargo complexes comprising cystein-containing peptides as cationic components which leads to a polymerization of the polymeric carrier by disulfide bonds do not change in size in contrast to the complexes formed by non-polymerizing peptides which increase in size and therefore are not stable during the lyophilization step. Therefore complexes with polymerized peptides as polymeric carriers show advantageous properties for lyophilization.

Figure 5:
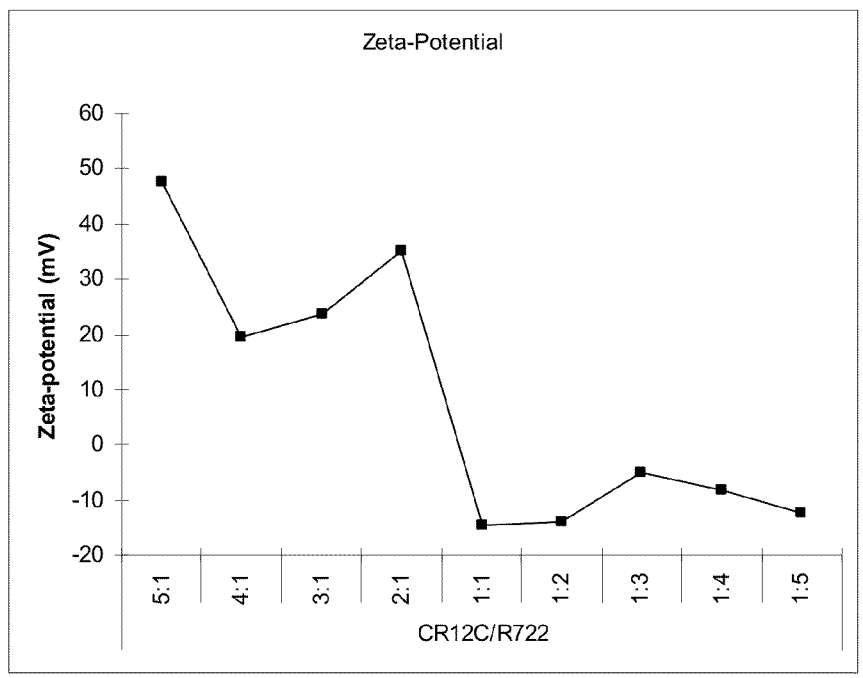

FIG. 5: shows the Zeta-potential of inventive polymeric carrier cargo complexes formed by the disulfide-cross-linked cationic peptide $CR_{12}C$ and the R722 as nucleic acid cargo at different w/w ratios according to the invention. As can be seen, the zeta potential changes from positive to negative when the w/w ratio is changed from excess peptide to a 1:1 ratio (peptide/RNA).

Figure 6:
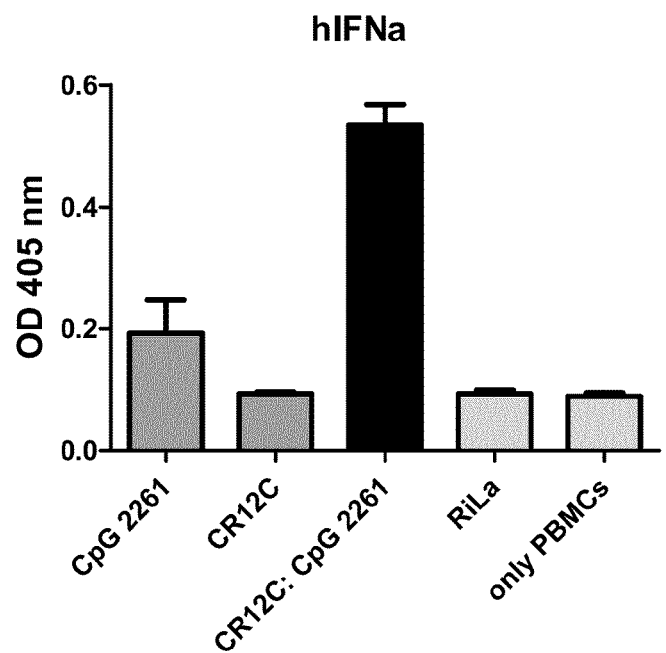
Figure 6:
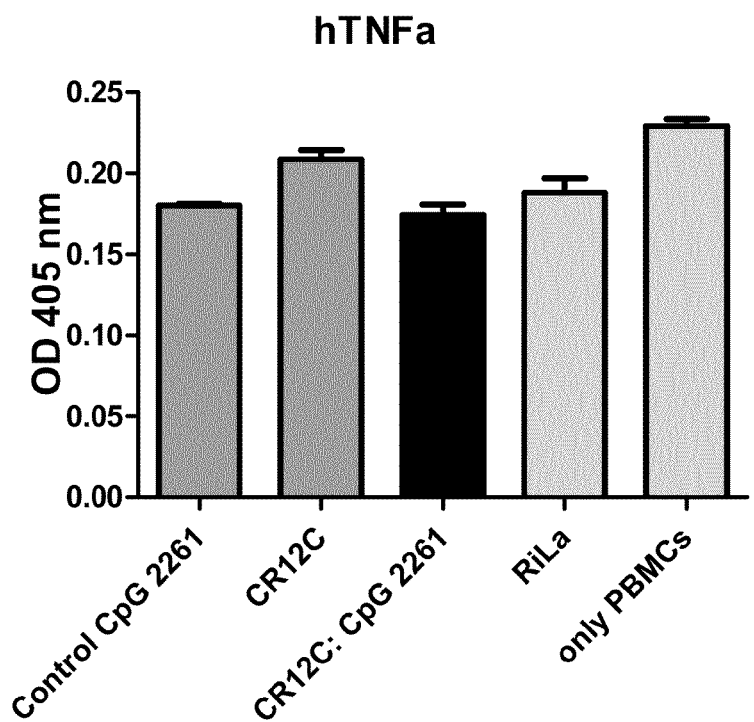

FIG. 6A: shows the secretion of hIFNa cytokine (in vitro) in hPBMCs after stimulation with polymeric carrier cargo complexes formed by the disulfide-crosslinked cationic peptide $CR_{12}C$ and the CpG 2216 as nucleic acid cargo in a mass ratio of 1:2.5 (w/w) ($CR_{12}C$/CpG 2216) according to the invention. As can be seen, the inventive polymeric carrier cargo complexes lead to an increase of hIFNa cytokine release in hPBMCs compared to the nucleic acid cargo alone or the cationic peptide alone.

FIG. 6B: shows the secretion of hTNFa cytokine (in vitro) in hPBMCs after stimulation with polymeric carrier cargo complexes formed by the disulfide-crosslinked cationic peptide $CR_{12}C$ and the CpG 2216 as nucleic acid cargo in a mass ratio of 1:2.5 (w/w) ($CR_{12}C$/CpG 2216) according to the invention. As can be seen, the inventive polymeric carrier cargo complexes do not lead to an increase in hTNFa cytokine release in hPBMCs compared to the nucleic acid cargo alone or the cationic peptide alone.

Figure 7:
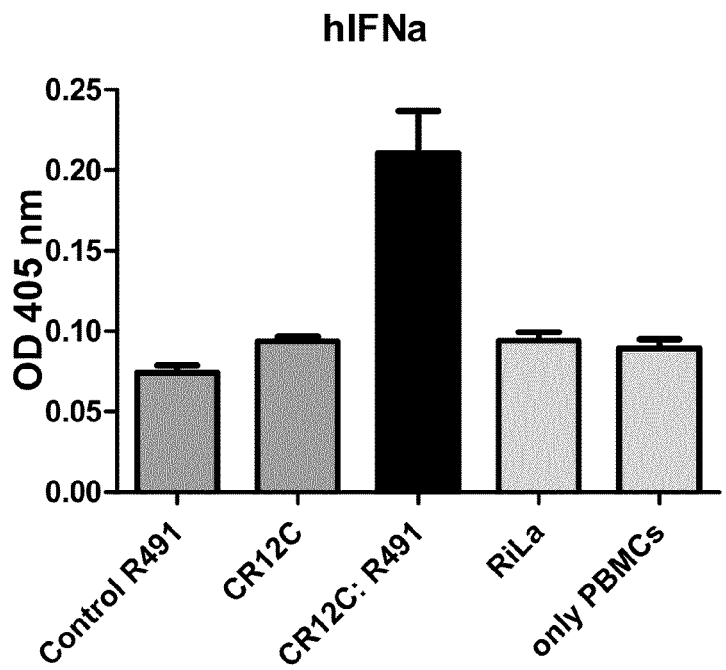
Figure 7:
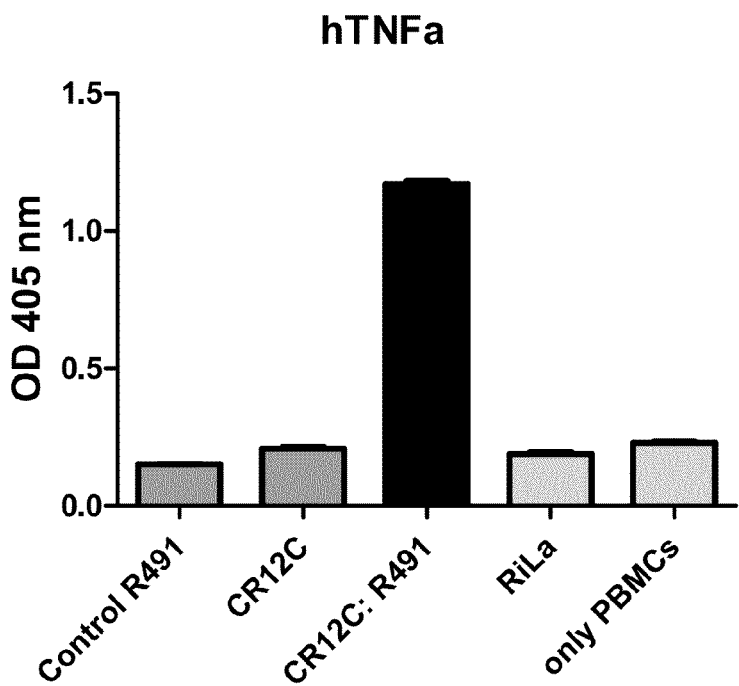

FIG. 7A: shows the secretion of hIFNa cytokine (in vitro) in hPBMCs after stimulation with polymeric carrier cargo complexes formed by the disulfide-crosslinked cationic peptide $CR_{12}C$ and the mRNA R491 coding for luciferase as nucleic acid cargo in a mass ratio of 1:2 (w/w) ($CR_{12}C$/R491) according to the invention. As can be seen, the inventive polymeric carrier cargo complexes lead to an increase of hIFNa cytokine release in hPBMCs compared to the nucleic acid cargo alone or the cationic peptide alone.

FIG. 7B: shows the secretion of hTNFa cytokine (in vitro) in hPBMCs after stimulation with polymeric carrier cargo complexes formed by the disulfide-crosslinked cationic peptide $CR_{12}C$ and the mRNA R491 coding for luciferase as nucleic acid cargo in a mass ratio of 1:2 (w/w) ($CR_{12}C$/R491) according to the invention. As can be seen, the inventive polymeric carrier cargo complexes lead to an increase of hTNFa cytokine release in hPBMCs compared to the nucleic acid cargo alone or the cationic peptide alone.

Figure 8:
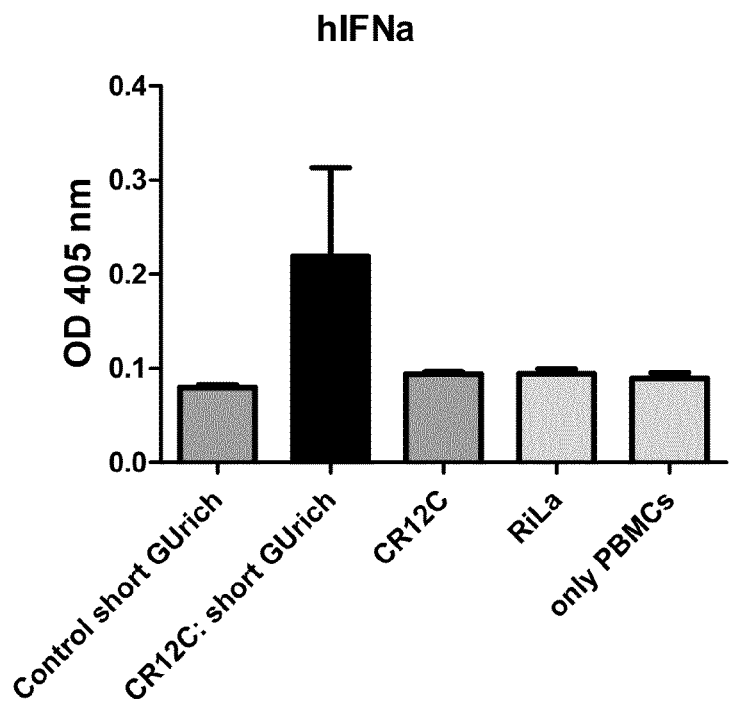
Figure 8:
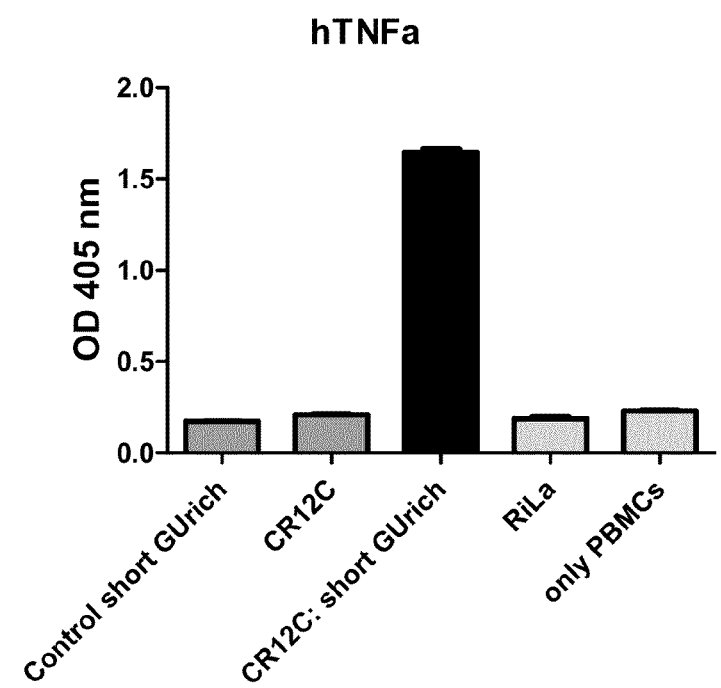

FIG. 8A: shows the secretion of hIFNa cytokine (in vitro) in hPBMCs after stimulation with polymeric carrier cargo complexes formed by the disulfide-crosslinked cationic peptide $CR_{12}C$ and a short GU rich RNA oligonucleotide (short GU rich) as nucleic acid cargo in a mass ratio of 1:2.5 (w/w) ($CR_{12}C$/short GU rich) according to the invention. As can be seen, the inventive polymeric carrier cargo complexes lead to an increase of hIFNa cytokine release in hPBMCs compared to the nucleic acid cargo alone or the cationic peptide alone.

FIG. 8B: shows the secretion of hTNFa cytokine (in vitro) in hPBMCs after stimulation with polymeric carrier cargo complexes formed by the disulfide-crosslinked cationic peptide $CR_{12}C$ and a short GU rich RNA oligonucleotide (short GU rich) as nucleic acid cargo in a mass ratio of 1:2.5 (w/w) ($CR_{12}C$/short GU rich) according to the invention. As can be seen, the inventive polymeric carrier cargo complexes lead to an increase of hTNFa cytokine release in hPBMCs compared to the nucleic acid cargo alone or the cationic peptide alone.

Figure 9:
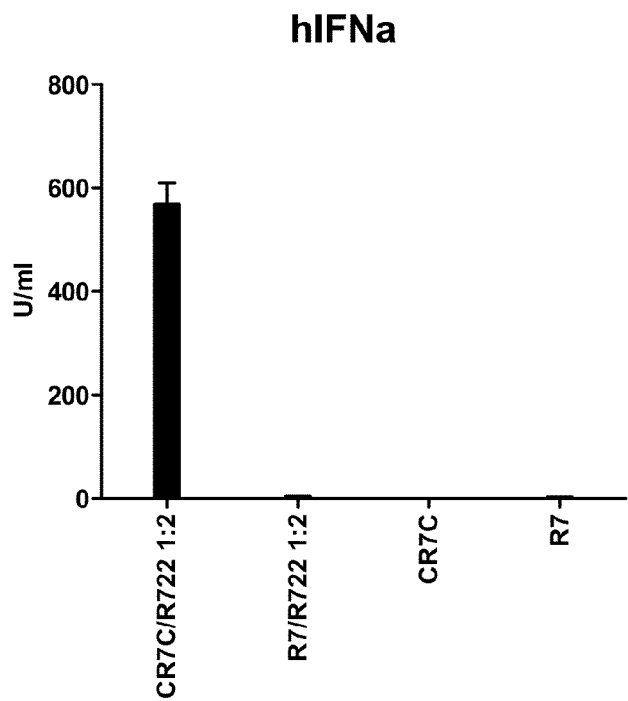
Figure 9:
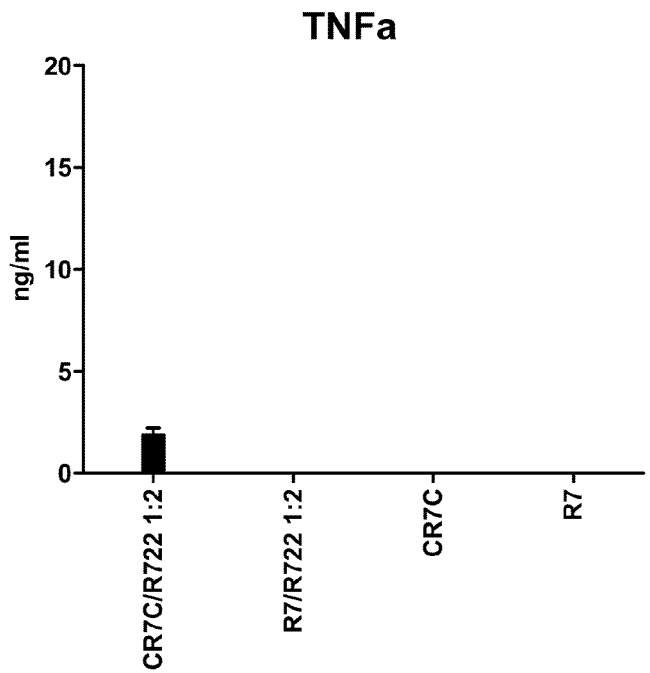

FIG. 9A: shows the secretion of hIFNa cytokine (in vitro) in hPBMCs after stimulation with polymeric carrier cargo complexes formed by the disulfide-crosslinked cationic peptide $CR_7C$ and the long non-coding GU-rich isRNA R722 as nucleic acid cargo according to the invention. As can be seen, the inventive polymeric carrier cargo complexes ($CR_7C$/R722) lead to an increase of hIFNa cytokine release in hPBMCs compared to non-inventive carrier cargo complexes ($R_7$/R722) formed by the non-polymerized peptide $R_7$.

FIG. 9B: shows the secretion of hTNFa cytokine (in vitro) in hPBMCs after stimulation with polymeric carrier cargo complexes formed by the disulfide-crosslinked cationic peptide $CR_7C$ and the long non-coding GU-rich isRNA R722 as nucleic acid cargo according to the invention. As can be seen, the inventive polymeric carrier cargo complexes ($CR_7C$/R722) only leads to a weak increase of hTNFa cytokine release in hPBMCs compared to non-inventive carrier cargo complexes ($R_7$/R722) formed by the non-polymerized peptide $R_7$.

Figure 10:
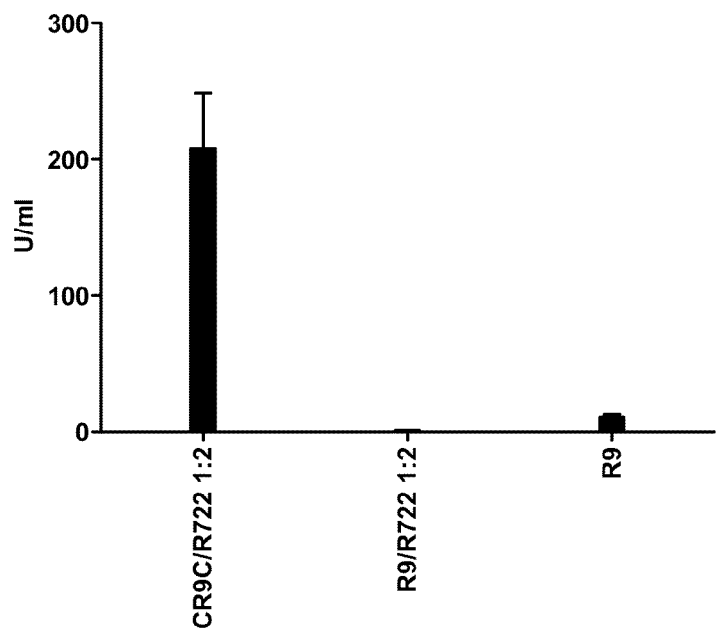
Figure 10:
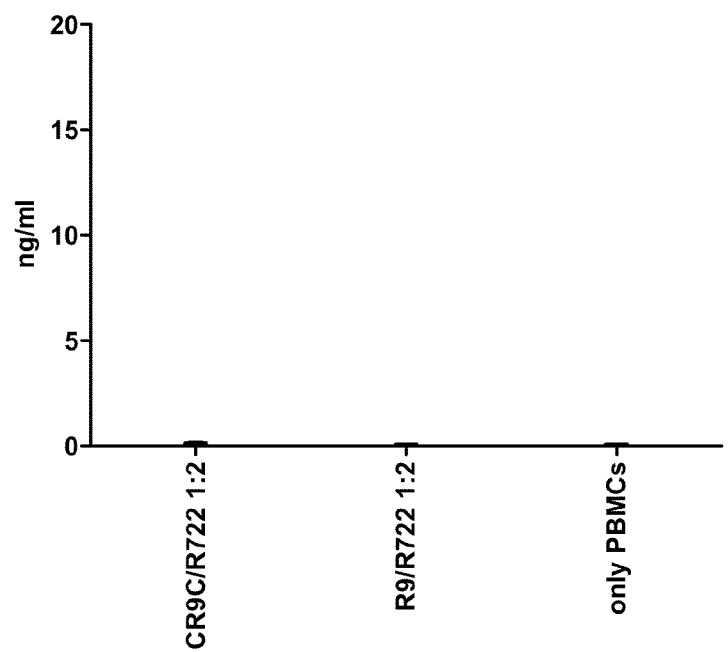

FIG. 10A: shows the secretion of hIFNa cytokine (in vitro) in hPBMCs after stimulation with polymeric carrier cargo complexes formed by the disulfide-crosslinked cationic peptide $CR_9C$ and the long non-coding GU-rich isRNA R722 as nucleic acid cargo according to the invention. As can be seen, the inventive polymeric carrier cargo complexes ($CR_9C$/R722) lead to an increase of hIFNa cytokine release in hPBMCs compared to non-inventive carrier cargo complexes ($R_9$/R722) formed by the non-polymerized peptide $R_9$.

FIG. 10B: shows the secretion of hTNFa cytokine (in vitro) in hPBMCs after stimulation with polymeric carrier cargo complexes formed by the disulfide-crosslinked cationic peptide $CR_9C$ and the long non-coding GU-rich isRNA R722 as nucleic acid cargo according to the invention. As can be seen, the inventive polymeric carrier cargo complexes ($CR_9C$/R722) do not lead to an increase of hTNFa cytokine release in hPBMCs compared to non-inventive carrier cargo complexes ($R_9$/R722) formed by the non-polymerized peptide $R_9$.

Figure 11:
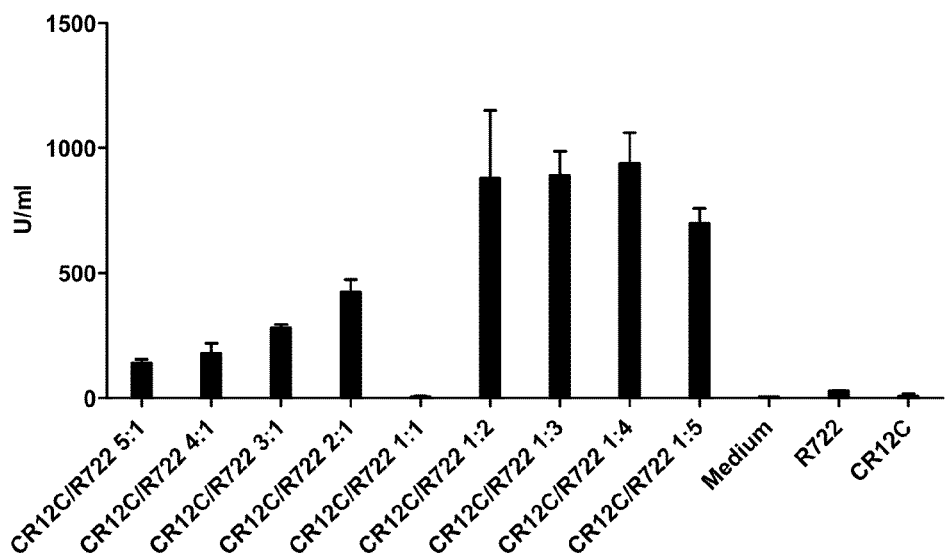
Figure 11:
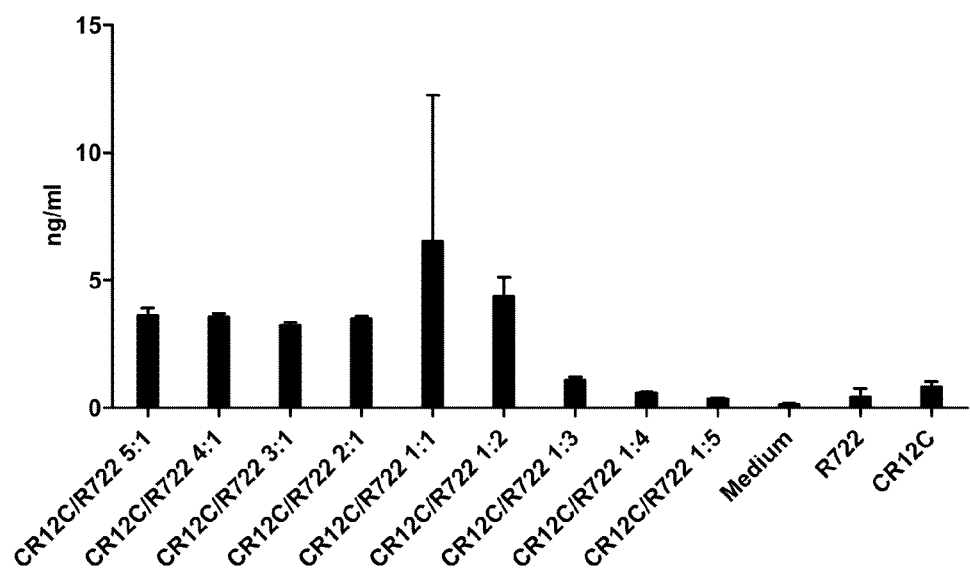

FIG. 11A: shows the secretion of hIFNa cytokine (in vitro) in hPBMCs after stimulation with polymeric carrier cargo complexes formed by the disulfide-crosslinked cationic peptide $CR_{12}C$ and the isRNA R722 as nucleic acid cargo at different w/w ratios according to the invention. As can be seen, the inventive polymeric carrier cargo complexes lead to an increase in hIFNa cytokine release in hPBMCs compared to the nucleic acid cargo alone or the cationic peptide alone.

FIG. 11B: shows the secretion of hTNFa cytokine (in vitro) in hPBMCs after stimulation with polymeric carrier cargo complexes formed by the disulfide-crosslinked cationic peptide $CR_{12}C$ and the isRNA R722 as nucleic acid cargo at different w/w ratios according to the invention. As can be seen, the inventive polymeric carrier cargo complexes lead to an increase in hTNFa cytokine release in hPBMCs compared to the nucleic acid cargo alone or the cationic peptide alone.

Figure 12:
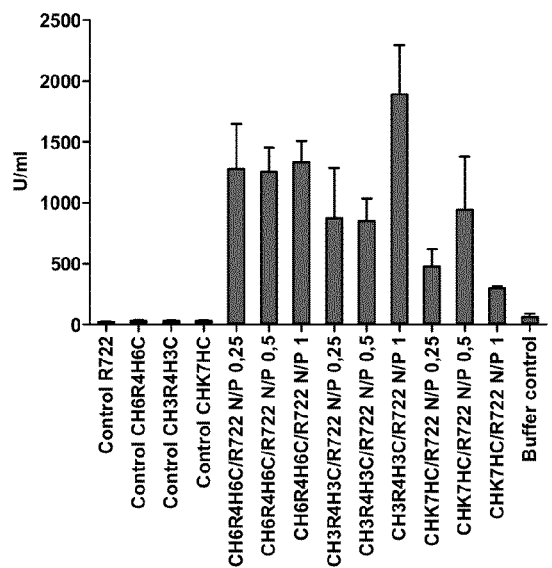
Figure 12:
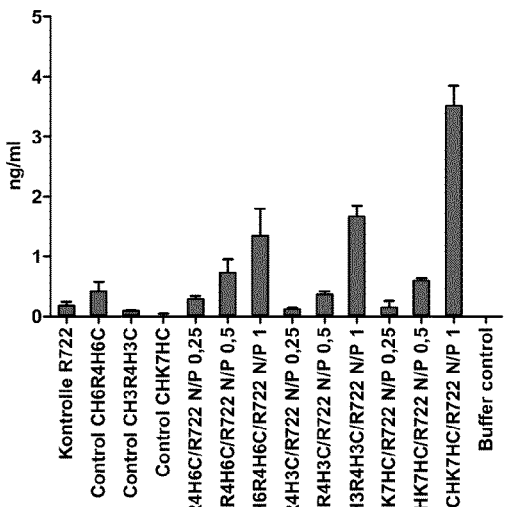

FIG. 12A: shows the secretion of hIFNa cytokine (in vitro) in hPBMCs after stimulation with polymeric carrier complexes formed by the cationic peptides $CH_6R_4H_6C$, $CH_3R_4H_3C$ and $CHK_7HC$ and the isRNA R722 as nucleic acid cargo at different N/P ratios according to the invention. As can be seen, the inventive polymeric carrier cargo complexes lead to an increase in hIFNa cytokine release in hPBMCs compared to the nucleic acid cargo alone or the cationic peptide alone.

FIG. 12B: shows the secretion of hTNFa cytokine (in vitro) in hPBMCs after stimulation with polymeric carrier complexes formed by the disulfide-crosslinked cationic peptides $CH_6R_4H_6C$, $CH_3R_4H_3C$ and $CHK_7HC$ and the isRNA R722 as nucleic acid cargo at different N/P ratios according to the invention. As can be seen, the inventive polymeric carrier cargo complexes lead to an increase in hTNFa cytokine release in hPBMCs compared to the nucleic acid cargo alone or the cationic peptide alone. Particularly inventive polymeric cargo complexes with an N/P ratio greater or equal 1 result in TNFalpha secretion.

Figure 13:
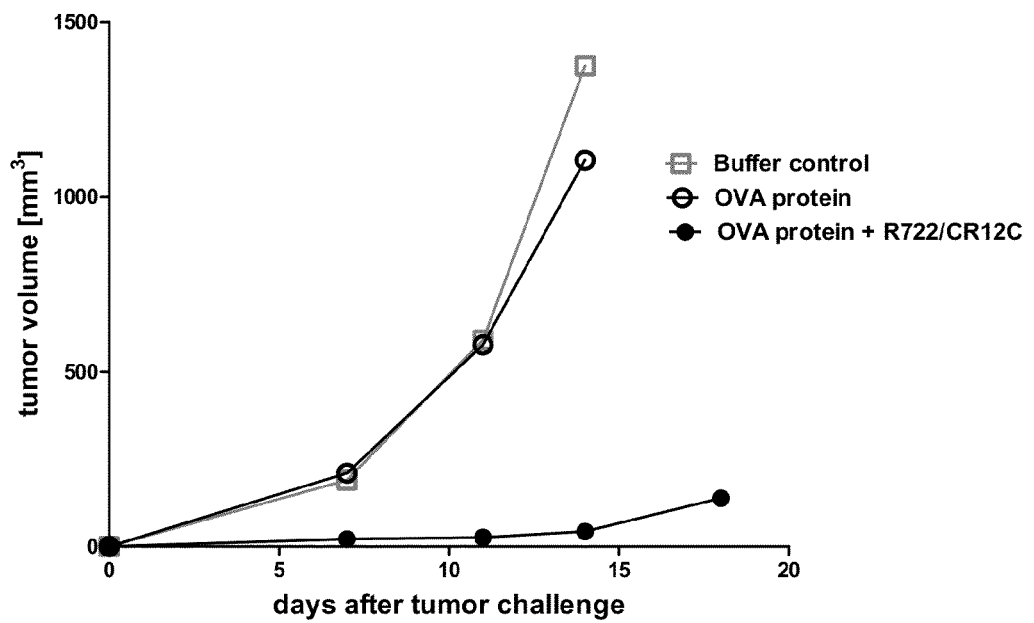

FIG. 13: shows the (in vivo) effect of the addition of the inventive polymeric carrier cargo complex formed by the disulfide-crosslinked cationic peptide $CR_{12}C$ as carrier and the isRNA R722 as nucleic acid cargo to the protein vaccine Ovalbumine (OVA protein) for the use as an adjuvant in tumour challenge experiments. As can be seen, the inventive polymeric carrier cargo complex extremely decelaterates the tumour growth compared to the protein vaccine alone, which has no effect on tumor growth in comparison to the buffer control.

Figure 14:
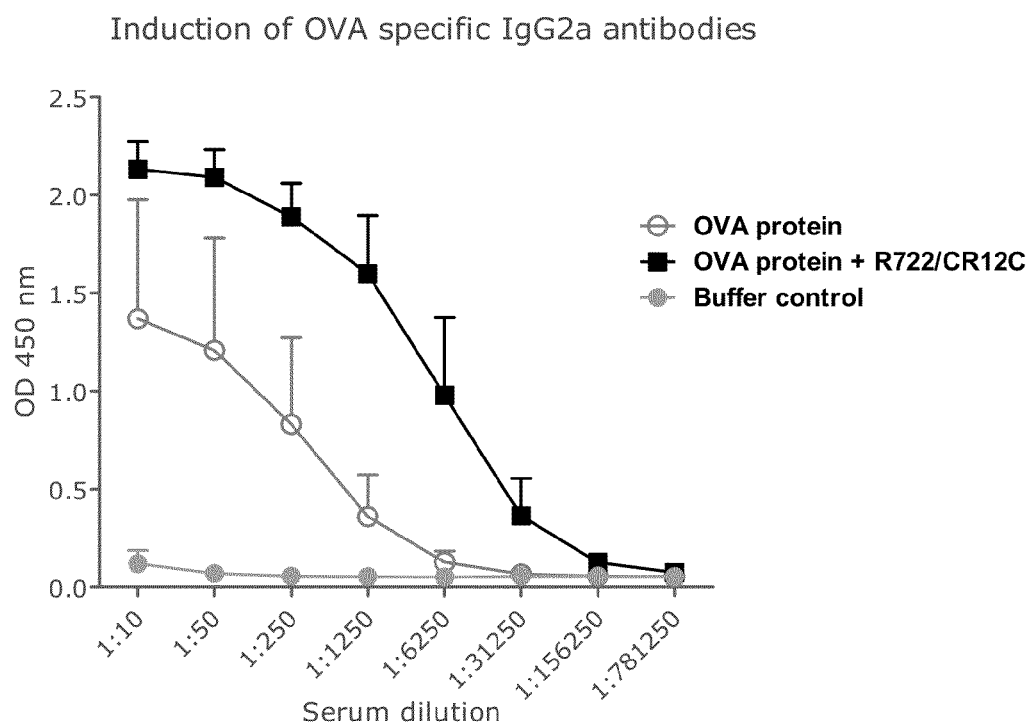

FIG. 14: shows the (in vivo) effect of the addition of the inventive polymeric carrier cargo complex formed by the disulfide-crosslinked cationic peptide $CR_{12}C$ as carrier and the isRNA R722 as nucleic acid cargo to the protein vaccine Ovalbumine (OVA protein) for the use as an adjuvant on the induction of Ovalbumine-specific IgG2a antibodies. As can be seen, the inventive polymeric carrier cargo complex strongly increases the B-cell response, which proofs the beneficial adjuvant properties of the inventive polymeric carrier cargo complexes, particularly in regard to the induction of a Th1-shifted immune response.

Figure 15:
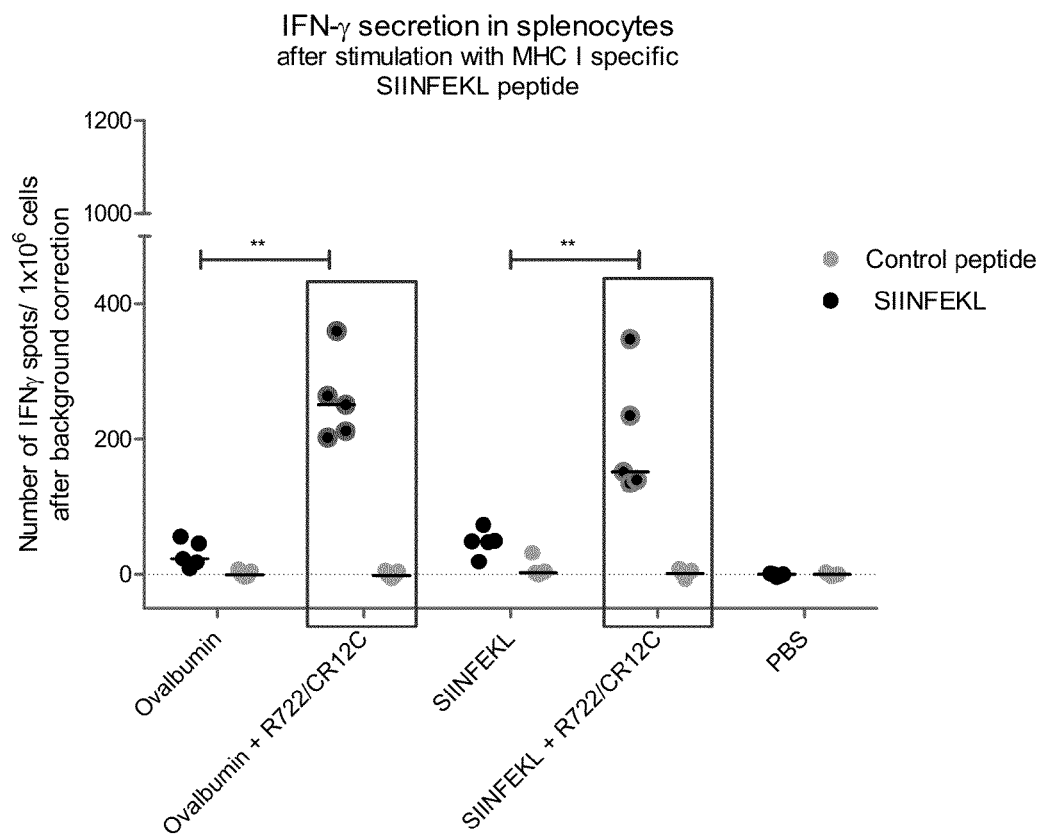

FIG. 15: shows the (in vivo) effect of the addition of the inventive polymeric carrier cargo complex formed by the disulfide-crosslinked cationic peptide $CR_{12}C$ as carrier and the isRNA R722 as nucleic acid cargo to the protein vaccine Ovalbumine (OVA protein) or the Ovalbumine-specific peptide vaccine SIINFEKL for the use as an adjuvant on the induction of Ovalbumine-specific cytotoxic T cells. As can be seen, the inventive polymeric carrier cargo complex strongly increases the induction of Ovalbumin-specific cytotoxic T cells compared to the vaccination with protein or peptide alone, which further proofs the beneficial adjuvant properties of the inventive polymeric carrier cargo complex, particularly in regard to the induction of a Th1-shifted immune response.

EXAMPLES

The following examples are intended to illustrate the invention further. They are not intended to limit the subject matter of the invention thereto.

1. Reagents:
Cationic Peptides as Cationic Component:

$R_7$:
Arg-Arg-Arg-Arg-Arg-Arg-Arg ($Arg_7$)

$CR_7C$:
Cys-Arg-Arg-Arg-Arg-Arg-Arg-Arg-Cys ($CysArg_7Cys$)

$R_9$:
Arg-Arg-Arg-Arg-Arg-Arg-Arg-Arg-Arg ($Arg_9$)

$R_{12}$:
Arg-Arg-Arg-Arg-Arg-Arg-Arg-Arg-Arg-Arg-Arg-Arg ($Arg_{12}$)

$CR_9C$:
Cys-Arg-Arg-Arg-Arg-Arg-Arg-Arg-Arg-Arg-Cys ($Cys-Arg_9-Cys$)

$CR_{12}C$:
Cys-Arg-Arg-Arg-Arg-Arg-Arg-Arg-Arg-Arg-Arg-Arg-Arg (Cys-$Arg_{12}$-Cys)

Nucleic Acids as Cargo:
R1180: mRNA coding for luciferase (SEQ ID NO. 384)
R722: long non-coding is GU-rich RNA (SEQ ID NO. 385)
R491: mRNA coding for luciferase (SEQ ID NO. 386)
CpG 2216: CpG oligonucleotide (SEQ ID NO. 387)
Short GU rich: GU-rich RNA oligonucleotide (SEQ ID NO. 369)

2. Preparation of Nucleic Acid Sequences:

For the present examples nucleic acid sequences as indicated in example 1 were prepared and used for formation of the inventive polymerized polymeric carrier cargo complexes or for non-polymerized carrier cargo complexes for comparison. These polymeric carrier cargo complexes were used for in vitro and in vivo transaction, for in vitro immunostimulation and for particle characterizations.

According to a first preparation, the DNA sequences, coding for the corresponding RNA sequences R1180, R722 and R491 sequences were prepared. The sequences of the corresponding RNAs are shown in the sequence listing (SEQ ID NOs: 384, 385 and 386).

The short GU rich sequences and the CpG 2216 oligonucleotides were prepared by automatic solid-phase synthesis by means of phosphoramidite chemistry. The sequences are shown in the sequence listing (SEQ ID NOs: 387 and 369).

2. In Vitro Transcription:

The respective DNA plasmids prepared according to Example 2 for R1180, R722 and R491 were transcribed in vitro using T7-Polymerase (T7-Opti mRNA Kit, CureVac, Tübingen, Germany) following the manufactures instructions. Subsequently the mRNA was purified using PureMessenger® (CureVac, Tübingen, Germany).

3. Synthesis of Polymeric Carrier Cargo Complexes:

The nucleic acid sequences defined above in Example 1 were mixed with the cationic components as defined in Example 1. Therefore, the indicated amount of nucleic acid sequence was mixed with the respective cationic component in mass ratios as indicated, thereby forming a complex. If polymerizing cationic components were used according to the present invention polymerization of the cationic components took place simultaneously to complexation of the nucleic acid cargo. Afterwards the resulting solution was adjusted with water to a final volume of 50 µl and incubated for 30 min at room temperature. The different ratios of cationic component/nucleic acid used in the experiments are shown in Table 1.

TABLE 1

| Sample (cationic peptide/nucleic acid) | Mass ratio | N/P ratio | Molar ratio |
|---|---|---|---|
| $CR_{12}C/R_{1180}$ | 1:2 | 0.9 | 44:1 |
| $CR_{12}C/R_{1180}$ | 2:1 | 3.6 | 185:1 |
| $R_{12}/R_{1180}$ | 1:2 | 0.7 | 48:1 |
| $R_{12}/R_{1180}$ | 2:1 | 2.5 | 146:1 |
| $CR_9C/R_{1180}$ | 2:1 | 0.9 | 55:1 |
| $R_9/R_{1180}$ | 2:1 | 1.1 | 65:1 |
| $CR_7C$ | 1:2 | 0.8 | 70:1 |
| $R_7$ | 1:2 | 1.0 | 85:1 |
| $CR_{12}C/CpG$ | 1:2.5 | 4.9 | 8:1 |
| $CR_{12}C/R_{491}$ | 1:2 | 0.9 | 150:1 |
| $CR_{12}C$/short GU-rich | 1:2.5 | 4.9 | 8:1 |
| $CR_{12}C/R_{722}$ | 5:1 | 9.6 | 444:1 |
| $CR_{12}C/R_{722}$ | 4:1 | 7.6 | 355:1 |
| $CR_{12}C/R_{722}$ | 3:1 | 5.7 | 266:1 |
| $CR_{12}C/R_{722}$ | 2:1 | 3.8 | 177:1 |
| $CR_{12}C/R_{722}$ | 1:1 | 1.9 | 88:1 |
| $CR_{12}C/R_{722}$ | 1:2 | 0.9 | 44:1 |

TABLE 1-continued

| Sample (cationic peptide/nucleic acid) | Mass ratio | N/P ratio | Molar ratio |
|---|---|---|---|
| $CR_{12}C/R_{722}$ | 1:3 | 0.6 | 29:1 |
| $CR_{12}C/R_{722}$ | 1:4 | 0.5 | 22:1 |
| $CR_{12}C/R_{722}$ | 1:5 | 0.4 | 17:1 |

N/P ratio = is a measure of the ionic charge of the cationic component of the polymeric carrier or of the polymeric carrier as such. In the case that the cationic properties of the cationic component are provided by nitrogen atoms the N/P ratio is the ratio of basic nitrogen atoms to phosphate residues, considering that nitrogen atoms confer to positive charges and phosphate of the phosphate backbone of the nucleic acid confers to the negative charge.

N/P is preferably calculated by the following formula:

$$N/P = \frac{\text{pmol [RNA]} * \text{ratio} * \text{cationic AS}}{\mu g \text{ RNA} * 3 * 1000}$$

As an example the RNA $R_{722}$ according to SEQ ID NO: 385 was applied, which has a molecular weight of 186 kDa. Therefore 1 µg $R_{722}$ RNA confers to 5.38 pmol RNA.

4. Transfection of HepG2 and B16F10 Cells:

Polymeric carrier cargo complexes containing 5 µg mRNA coding for luciferase (R1180) were prepared as indicated in Example 3. HepG2 or B16F10 cells ($150 \times 10^3$/well) were seeded 1 day prior to transfection on 24-well microtiter plates leading to a 70% confluence when transfection was carried out. For transfection 50 µl of the polymeric carrier cargo complex solution were mixed with 250 µl serum free medium and added to the cells (final RNA concentration: 13 µg/ml). Prior to addition of the serum free transfection solution the cells were washed gently and carefully 2 times with 1 ml OPTI-MEM (Invitrogen) per well. Then, the transfection solution (300 µl per well) was added to the cells and the cells were incubated for 4 h at 37° C. Subsequently 100 µl RPMI-medium (Camprex) containing 10% FCS was added per well and the cells were incubated for additional 20 h at 37° C. The transfection solution was sucked off 24 h after transfection and the cells were lysed in 300 µl lysis buffer (25 mM Tris-$PO_4$, 2 mM EDTA, 10% glycerol, 1% Triton-X 100, 2 mM DTT). The supernatants were then mixed with luciferin buffer (25 mM Glycylglycin, 15 mM $MgSO_4$, 5 mM ATP, 62.5 µM luciferin) and luminiscence was detected using a luminometer (Lumat LB 9507 (Berthold Technologies, Bad Wildbad, Germany)).

5. Expression of Luciferase In Vivo:

Polymeric carrier cargo complexes containing 5 µg mRNA coding for luciferase (R1180) were prepared as indicated in Example 3. Afterwards the resulting solution was adjusted with Ringer Lactate solution to a final volume of 100 µl and incubated for 30 minutes at room temperature, yielding a solution with a 0.1 g/l concentration of polymeric carrier cargo complexes. 100 µl of this solution was administrated intradermally (in the back) of 7 week old BALB/c mice. After 24 h the mice were sacrificed and the samples (skin from the back) were collected, frozen at −78° C. and lysed for 3 Minutes at full speed in a tissue lyser (Qiagen, Hilden, Germany). Afterwards 600 µl of lysis buffer were added and the resulting solutions were subjected another 6 minutes at full speed in the tissue lyser. After 10 minutes centrifugation at 13500 rpm at 4° C. the supernatants were mixed with luciferin buffer (25 mM Glycylglycin, 15 mM $MgSO_4$, 5 mM ATP, 62.5 µM luciferin) and luminiscence was detected using a luminometer (Lumat LB 9507 (Berthold Technologies, Bad Wildbad, Germany)).

6. Cytokine Stimulation in hPBMCs:

HPBMC cells from peripheral blood of healthy donors were isolated using a Ficoll gradient and washed subsequently with 1 (PBS (phophate-buffered saline). The cells were then seeded on 96-well microtiter plates ($200 \times 10^3$/well). The hPBMC cells were incubated for 24 h with 10 µl of the inventive polymeric carrier cargo complex from Example 3 containing the indicated amount of nucleic acid in X-VIVO 15 Medium (BioWhittaker). The immunostimulatory effect was measured by detecting the cytokine production of the hPBMCs (Tumour necrose factor alpha and Interferon alpha). Therefore, ELISA microtiter plates (Nunc MAXISORP) were incubated over night (o/n) with binding buffer (0.02% $NaN_3$, 15 mM $Na_2CO_3$, 15 mM $NaHCO_3$, pH 9.7), additionally containing a specific cytokine antibody. Cells were then blocked with 1×PBS, containing 1% BSA (bovine serum albumin). The cell supernatant was added and incubated for 4 h at 37° C. Subsequently, the microtiter plate was washed with 1×PBS, containing 0.05% TWEEN-20 and then incubated with a Biotin-labelled secondary antibody (BD Pharmingen, Heidelberg, Germany). Streptavidin-coupled horseraddish peroxidase was added to the plate. Then, the plate was again washed with 1×PBS, containing 0.05% TWEEN-20 and ABTS (2,2'-azino-bis(3-ethyl-benzthiazoline-6-sulfonic acid) was added as a substrate. The amount of cytokine was determined by measuring the absorption at 405 nm (OD 405) using a standard curve with recombinant cytokines (BD Pharmingen, Heidelberg, Germany) with the SUNRISE ELISA-Reader from Tecan (Crailsheim, Germany).

7. Zetapotential Measurements:

The Zeta potential of the polymeric carrier cargo complexes was evaluated by the laser Doppler electrophoresis method using a Zetasizer Nano (Malvern Instruments, Malvern, UK). The measurement was performed at 25° C. and a scattering angle of 173° was used.

8. Stability of Complexes after Lyophilization

The hydrodynamic diameters of polymeric carrier cargo complexes as prepared above were measured by dynamic light scattering using a Zetasizer Nano (Malvern Instruments, Malvern, UK) according to the manufacturer's instructions. The measurements were performed at 25° C. in buffer analysed by a cumulant method to obtain the hydrodynamic diameters and polydispersity indices of the polymeric carrier cargo complexes. Polymeric carrier cargo complexes were formed as indicated in Example 3 and the hydrodynamic diameters were measured with fresh prepared complexes and with reconstituted complexes after lyophilization.

9. Immunization Experiments:

For immunization the vaccines Ovalbumine protein (OVA) (5 µg) or Ovalbumin-specific peptide SIINFEKL (50 µg) were combined with the inventive polymeric cargo complexes R722/$CR_{12}C$ (in a ratio of 2:1 w/w) (30 µg R722/15 µg $CR_{12}C$). as adjuvant and injected intradermally into female C57BL/6 mice (7 mice per group for tumour challenge and 5 mice per group for detection of an immune response). The vaccination was repeated 2 times in 2 weeks. For comparison mice were injected without the inventive polymeric cargo complexes.

10. Detection of an Antigen-Specific Immune Response (B-Cell Immune Response):

Detection of an antigen specific immune response (B-cell immune response) was carried out by detecting antigen specific antibodies. Therefore, blood samples were taken from vaccinated mice 5 days after the last vaccination and sera were prepared. MaxiSorb plates (Nalgene Nunc International) were coated with *Gallus gallus* ovalbumine protein. After blocking with 1×PBS containing 0.05% TWEEN-20 and 1% BSA the plates were incubated with diluted mouse serum. Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured.

11. Detection of an Antigen Specific Cellular Immune Response by ELISPOT:

5 days after the last vaccination mice were sacrificed, the spleens were removed and the splenocytes were isolated. For detection of INFgamma a coat multiscreen plate (Millipore) was incubated overnight with coating buffer (0.1 M Carbonat-Bicarbonat Buffer pH 9.6, 10.59 g/l Na2CO3, 8.4 g/l NaHCO3) comprising antibody against INFy (BD Pharmingen, Heidelberg, Germany). The next day 1×106 cells/well were added and re-stimulated with 1 μg/well of relevant peptide (SIINFEKL of ovalbumine); irrelevant peptide (Connexin=control peptide) or buffer without peptide. Afterwards the cells are incubated for 24 h at 37° C. The next day the plates were washed 3 times with PBS, once with water and once with PBS/0.05% TWEEN-20 and afterwards incubated with a biotin-coupled secondary antibody for 11-24 h at 4° C. Then the plates were washed with PBS/0.05% TWEEN-20 and incubated for 2 h at room temperature with alkaline phosphatase coupled to streptavidin in blocking buffer. After washing with PBS/0.05% TWEEN-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction.

12. Tumour Challenge:

One week after the last vaccination $1\times10^6$ E.G$_7$-OVA cells (tumour cells which stably express ovalbumine) were implanted subcutaneously in the vaccinated mice. Tumour growth was monitored by measuring the tumour size in 3 dimensions using a calliper.

The invention claimed is:

1. A method of stimulating, enhancing or increasing TNFα and/or INFα expression in a subject in need thereof comprising administering to the subject a polymeric carrier cargo complex comprising:
   (a) as a carrier a polymeric carrier formed by disulfide-crosslinked cationic peptides or proteins selected from the group consisting of $CR_{12}C$ (SEQ ID NO: 6), $CR_9C$ (SEQ ID NO: 3), $CR_7C$ (SEQ ID NO: 1), $CH_6R_4H_6C$ (SEQ ID NO: 388), $CHK_7HC$ (SEQ ID NO: 389) and $CH_3R_4H_3C$ (SEQ ID NO: 390), said polymeric carrier comprising at least 2 of said cationic peptides or proteins which are disulfide crosslinked, and
   (b) as a cargo at least one nucleic acid molecule,
   thereby stimulating, enhancing or increasing TNFα and/or INFα expression in the subject.

2. The method of claim 1, wherein the at least one nucleic acid molecule is an RNA.

3. The method of claim 2, wherein the RNA is a GU rich RNA.

4. The method of claim 1, wherein the at least one nucleic acid molecule is an immunostimulatory nucleic acid.

5. The method of claim 1, wherein the at least one nucleic acid molecule is an immunostimulatory RNA (is RNA) or an mRNA.

6. The method of claim 1, wherein the nitrogen/phosphate (N/P) ratio of the cationic components of the polymeric carrier to the at least one nucleic acid molecule is in the range of 0.1-20.

7. The method of claim 6, wherein the nitrogen/phosphate (N/P) ratio of the cationic components of the polymeric carrier to the at least one nucleic acid molecule is in the range of 0.1-5.

8. The method of claim 7, wherein the nitrogen/phosphate (N/P) ratio of the cationic components of the polymeric carrier to the at least one nucleic acid molecule is in the range of 0.1-1.

9. The method of claim 1, wherein the polymeric carrier further comprises functional peptides or proteins.

10. The method of claim 9, wherein the functional peptides or proteins are peptide or protein antigens or antigen epitopes.

11. The method of claim 1, wherein the polymeric carrier further comprises a ligand.

12. The method of claim 11, wherein the ligand is mannose.

13. The method of claim 1, wherein disulfide-bonds are formed by the N- and C-terminal cysteine residues in the cationic peptides or proteins.

14. The method of claim 1, wherein the subject has a cancer, a cardiovascular disease, an infectious disease, an autoimmune disease or an allergy.

15. The method of claim 1, wherein the polymeric carrier cargo complex does not comprise a polyethylene glycol (PEG) polymer chain.

16. The method of claim 1, wherein the cationic peptides or proteins are $CR_{12}C$ (SEQ ID NO: 6), $CR_9C$ (SEQ ID NO: 3), $CR_7C$ (SEQ ID NO: 1), $CH_6R_4H_6C$ (SEQ ID NO: 388), or $CH_3R_4H_3C$ (SEQ ID NO: 390).

* * * * *

UNITED STATES PATENT AND TRADEMARK OFFICE
CERTIFICATE OF CORRECTION

PATENT NO. : 8,968,746 B2  
APPLICATION NO. : 13/203653  
DATED : March 3, 2015  
INVENTOR(S) : Patrick Baumhof et al.

It is certified that error appears in the above-identified patent and that said Letters Patent is hereby corrected as shown below:

In title page, item (30) Foreign Application Priority Data, insert
--Jul. 30, 2010     (EP)...........10007992.0--.

In the Claims

In claim 5, column 221, line 49, delete "is RNA" and insert --isRNA-- therefor.

Signed and Sealed this
Eleventh Day of August, 2015

Michelle K. Lee
*Director of the United States Patent and Trademark Office*

SEQUENCE LISTING

```
<160> NUMBER OF SEQ ID NOS: 390

<210> SEQ ID NO 1
<211> LENGTH: 9
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 1

Cys Arg Arg Arg Arg Arg Arg Arg Cys
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 2

Cys Arg Arg Arg Arg Arg Arg Arg Arg Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 3

Cys Arg Arg Arg Arg Arg Arg Arg Arg Arg Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Sequence: cationic or
      polycationic peptide of formula (Ib):
```

Cys {(Arg)l;(Lys)m;(His)n;(Orn)o;(Xaa)x} Cys

<400> SEQUENCE: 4

Cys Arg Arg Arg Arg Arg Arg Arg Arg Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 5

Cys Arg Arg Arg Arg Arg Arg Arg Arg Arg Arg Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 6

Cys Arg Arg Arg Arg Arg Arg Arg Arg Arg Arg Arg Cys
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 7

Cys Arg Arg Arg Arg Arg Arg Arg Arg Arg Arg Arg Arg Cys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 8

Cys Arg Arg Arg Arg Arg Arg Arg Arg Arg Arg Arg Arg Arg Cys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 9

```
Cys Arg Arg Arg Arg Arg Arg Arg Arg Arg Arg Arg Arg Arg Arg
1               5                   10                  15

Cys

<210> SEQ ID NO 10
<211> LENGTH: 18
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 10

Cys Arg Arg Arg Arg Arg Arg Arg Arg Arg Arg Arg Arg Arg Arg
1               5                   10                  15

Arg Cys

<210> SEQ ID NO 11
<211> LENGTH: 19
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 11

Cys Arg Arg Arg Arg Arg Arg Arg Arg Arg Arg Arg Arg Arg Arg
1               5                   10                  15

Arg Arg Cys

<210> SEQ ID NO 12
<211> LENGTH: 20
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 12

Cys Arg Arg Arg Arg Arg Arg Arg Arg Arg Arg Arg Arg Arg Arg
1               5                   10                  15

Arg Arg Arg Cys
            20

<210> SEQ ID NO 13
<211> LENGTH: 21
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 13

Cys Arg Arg Arg Arg Arg Arg Arg Arg Arg Arg Arg Arg Arg Arg
1               5                   10                  15

Arg Arg Arg Arg Cys
            20

<210> SEQ ID NO 14
<211> LENGTH: 22
<212> TYPE: PRT
```

```
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 14

Cys Arg Arg Arg Arg Arg Arg Arg Arg Arg Arg Arg Arg
1               5                   10                  15

Arg Arg Arg Arg Arg Cys
            20

<210> SEQ ID NO 15
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 15

Trp Tyr
1

<210> SEQ ID NO 16
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 16

Tyr Trp
1

<210> SEQ ID NO 17
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 17

Trp Trp
1

<210> SEQ ID NO 18
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 18

Tyr Tyr
1

<210> SEQ ID NO 19
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 19

Trp Tyr Trp
1
```

```
<210> SEQ ID NO 20
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 20

Tyr Trp Tyr
1

<210> SEQ ID NO 21
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 21

Trp Trp Trp
1

<210> SEQ ID NO 22
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 22

Tyr Tyr Tyr
1

<210> SEQ ID NO 23
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 23

Trp Tyr Trp Tyr
1

<210> SEQ ID NO 24
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 24

Tyr Trp Tyr Trp
1

<210> SEQ ID NO 25
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 25

Trp Trp Trp Trp
1
```

```
<210> SEQ ID NO 26
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 26

Phe Tyr
1

<210> SEQ ID NO 27
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 27

Tyr Phe
1

<210> SEQ ID NO 28
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 28

Phe Phe
1

<210> SEQ ID NO 29
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 29

Phe Tyr Phe
1

<210> SEQ ID NO 30
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 30

Tyr Phe Tyr
1

<210> SEQ ID NO 31
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 31

Phe Phe Phe
1

<210> SEQ ID NO 32
```

```
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 32

Phe Tyr Phe Tyr
1

<210> SEQ ID NO 33
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 33

Tyr Phe Tyr Phe
1

<210> SEQ ID NO 34
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 34

Phe Phe Phe Phe
1

<210> SEQ ID NO 35
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 35

Phe Trp
1

<210> SEQ ID NO 36
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 36

Trp Phe
1

<210> SEQ ID NO 37
<211> LENGTH: 2
<212> TYPE: PRT
<213> ORGANISM: Artificial Sequence
<220> FEATURE:
<223> OTHER INFORMATION: Exemplary aromatic amino acid component (AA)

<400> SEQUENCE: 37

Phe Phe
1

<210> SEQ ID NO 38
<211> LENGTH: 3
```

```
<212> TYPE: PRT
<213> ORGANISM: Artificial Sequence
<220> FEATURE:
<223> OTHER INFORMATION: Exemplary aromatic amino acid component (AA)

<400> SEQUENCE: 38

Phe Trp Phe
1

<210> SEQ ID NO 39
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 39

Trp Phe Trp
1

<210> SEQ ID NO 40
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 40

Phe Trp Phe Trp
1

<210> SEQ ID NO 41
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 41

Trp Phe Trp Phe
1

<210> SEQ ID NO 42
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 42

Tyr Tyr Tyr Tyr
1

<210> SEQ ID NO 43
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 43

Cys Tyr Cys
1

<210> SEQ ID NO 44
<211> LENGTH: 3
<212> TYPE: PRT
```

```
<213> ORGANISM: Artificial Sequence
<220> FEATURE:
<223> OTHER INFORMATION: Exemplary aromatic amino acid component (AA)

<400> SEQUENCE: 44

Cys Trp Cys
1

<210> SEQ ID NO 45
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 45

Cys Trp Tyr Cys
1

<210> SEQ ID NO 46
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 46

Cys Tyr Trp Cys
1

<210> SEQ ID NO 47
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 47

Cys Trp Trp Cys
1

<210> SEQ ID NO 48
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 48

Cys Tyr Tyr Cys
1

<210> SEQ ID NO 49
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 49

Cys Trp Tyr Trp Cys
1               5

<210> SEQ ID NO 50
<211> LENGTH: 5
<212> TYPE: PRT
<213> ORGANISM: Artificial Sequence
```

<220> FEATURE:
<223> OTHER INFORMATION: Exemplary aromatic amino acid component (AA)

<400> SEQUENCE: 50

Cys Tyr Trp Tyr Cys
1               5

<210> SEQ ID NO 51
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 51

Cys Trp Trp Trp Cys
1               5

<210> SEQ ID NO 52
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 52

Cys Tyr Tyr Tyr Cys
1               5

<210> SEQ ID NO 53
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 53

Cys Trp Tyr Trp Tyr Cys
1               5

<210> SEQ ID NO 54
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 54

Cys Tyr Trp Tyr Trp Cys
1               5

<210> SEQ ID NO 55
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 55

Cys Trp Trp Trp Trp Cys
1               5

<210> SEQ ID NO 56
<211> LENGTH: 6
<212> TYPE: PRT
<213> ORGANISM: Artificial Sequence
<220> FEATURE:

<223> OTHER INFORMATION: Exemplary aromatic amino acid component (AA)

<400> SEQUENCE: 56

Cys Tyr Tyr Tyr Tyr Cys
1               5

<210> SEQ ID NO 57
<211> LENGTH: 3
<212> TYPE: PRT
<213> ORGANISM: Artificial Sequence
<220> FEATURE:
<223> OTHER INFORMATION: Exemplary aromatic amino acid component (AA)

<400> SEQUENCE: 57

Cys Phe Cys
1

<210> SEQ ID NO 58
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 58

Cys Phe Tyr Cys
1

<210> SEQ ID NO 59
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 59

Cys Tyr Phe Cys
1

<210> SEQ ID NO 60
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 60

Cys Phe Phe Cys
1

<210> SEQ ID NO 61
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 61

Cys Tyr Tyr Cys
1

<210> SEQ ID NO 62
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 62

Cys Phe Tyr Phe Cys
1               5

<210> SEQ ID NO 63
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 63

Cys Tyr Phe Tyr Cys
1               5

<210> SEQ ID NO 64
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 64

Cys Phe Phe Phe Cys
1               5

<210> SEQ ID NO 65
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 65

Cys Tyr Tyr Tyr Cys
1               5

<210> SEQ ID NO 66
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 66

Cys Phe Tyr Phe Tyr Cys
1               5

<210> SEQ ID NO 67
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 67

Cys Tyr Phe Tyr Phe
1               5

<210> SEQ ID NO 68
<211> LENGTH: 6
<212> TYPE: PRT
<213> ORGANISM: Artificial Sequence
<220> FEATURE:
<223> OTHER INFORMATION: Exemplary aromatic amino acid component (AA)

```
<400> SEQUENCE: 68

Cys Phe Phe Phe Phe Cys
1               5

<210> SEQ ID NO 69
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 69

Cys Phe Trp Cys
1

<210> SEQ ID NO 70
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 70

Cys Trp Phe Cys
1

<210> SEQ ID NO 71
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 71

Cys Phe Phe Cys
1

<210> SEQ ID NO 72
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 72

Cys Phe Trp Phe Cys
1               5

<210> SEQ ID NO 73
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 73

Cys Trp Phe Trp Cys
1               5

<210> SEQ ID NO 74
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 74
```

```
Cys Phe Trp Phe Trp Cys
1               5

<210> SEQ ID NO 75
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 75

Cys Trp Phe Trp Phe Cys
1               5

<210> SEQ ID NO 76
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 76

Ser Thr
1

<210> SEQ ID NO 77
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 77

Thr Ser
1

<210> SEQ ID NO 78
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 78

Ser Ser
1

<210> SEQ ID NO 79
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 79

Thr Thr
1

<210> SEQ ID NO 80
<211> LENGTH: 3
<212> TYPE: PRT
<213> ORGANISM: Artificial Sequence
<220> FEATURE:
```

<223> OTHER INFORMATION: Exemplary hydrophilic (and preferably non
      charged polar) amino acid component (AA)

<400> SEQUENCE: 80

Ser Thr Ser
1

<210> SEQ ID NO 81
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 81

Thr Ser Thr
1

<210> SEQ ID NO 82
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 82

Ser Ser Ser
1

<210> SEQ ID NO 83
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 83

Thr Thr Thr
1

<210> SEQ ID NO 84
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 84

Ser Thr Ser Thr
1

<210> SEQ ID NO 85
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 85

Thr Ser Thr Ser
1

```
<210> SEQ ID NO 86
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 86

Ser Ser Ser Ser
1

<210> SEQ ID NO 87
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 87

Thr Thr Thr Thr
1

<210> SEQ ID NO 88
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 88

Gln Asn
1

<210> SEQ ID NO 89
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 89

Asn Gln
1

<210> SEQ ID NO 90
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 90

Gln Gln
1

<210> SEQ ID NO 91
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 91
```

Asn Asn
1

<210> SEQ ID NO 92
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 92

Gln Asn Gln
1

<210> SEQ ID NO 93
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 93

Asn Gln Asn
1

<210> SEQ ID NO 94
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 94

Gln Gln Gln
1

<210> SEQ ID NO 95
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 95

Asn Asn Asn
1

<210> SEQ ID NO 96
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 96

Gln Asn Gln Asn
1

<210> SEQ ID NO 97
<211> LENGTH: 4
<212> TYPE: PRT
<213> ORGANISM: Artificial Sequence

```
<220> FEATURE:
<223> OTHER INFORMATION: Exemplary hydrophilic (and preferably non
      charged polar) amino acid component (AA)

<400> SEQUENCE: 97

Asn Gln Asn Gln
1

<210> SEQ ID NO 98
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 98

Gln Gln Gln Gln
1

<210> SEQ ID NO 99
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 99

Asn Asn Asn Asn
1

<210> SEQ ID NO 100
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 100

Ser Asn
1

<210> SEQ ID NO 101
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 101

Asn Ser
1

<210> SEQ ID NO 102
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 102

Ser Ser
1
```

<210> SEQ ID NO 103
<211> LENGTH: 2
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 103

Asn Asn
1

<210> SEQ ID NO 104
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 104

Ser Asn Ser
1

<210> SEQ ID NO 105
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 105

Asn Ser Asn
1

<210> SEQ ID NO 106
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 106

Ser Ser Ser
1

<210> SEQ ID NO 107
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 107

Asn Asn Asn
1

<210> SEQ ID NO 108
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

```
<400> SEQUENCE: 108

Ser Asn Ser Asn
1

<210> SEQ ID NO 109
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 109

Asn Ser Asn Ser
1

<210> SEQ ID NO 110
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 110

Ser Ser Ser Ser
1

<210> SEQ ID NO 111
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 111

Asn Asn Asn Asn
1

<210> SEQ ID NO 112
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 112

Cys Thr Cys
1

<210> SEQ ID NO 113
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 113

Cys Ser Cys
1

<210> SEQ ID NO 114
<211> LENGTH: 4
<212> TYPE: PRT
```

```
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 114

Cys Ser Thr Cys
1

<210> SEQ ID NO 115
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 115

Cys Thr Ser Cys
1

<210> SEQ ID NO 116
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 116

Cys Ser Ser Cys
1

<210> SEQ ID NO 117
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 117

Cys Thr Thr Cys
1

<210> SEQ ID NO 118
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 118

Cys Ser Thr Ser Cys
1               5

<210> SEQ ID NO 119
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 119

Cys Thr Ser Thr Cys
1               5
```

<210> SEQ ID NO 120
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 120

Cys Ser Ser Ser Cys
1               5

<210> SEQ ID NO 121
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 121

Cys Thr Thr Thr Cys
1               5

<210> SEQ ID NO 122
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 122

Cys Ser Thr Ser Thr Cys
1               5

<210> SEQ ID NO 123
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 123

Cys Thr Ser Thr Ser Cys
1               5

<210> SEQ ID NO 124
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 124

Cys Ser Ser Ser Ser Cys
1               5

<210> SEQ ID NO 125
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

```
<400> SEQUENCE: 125

Cys Thr Thr Thr Thr Cys
1               5

<210> SEQ ID NO 126
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 126

Cys Asn Cys
1

<210> SEQ ID NO 127
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 127

Gln Cys Gln
1

<210> SEQ ID NO 128
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 128

Cys Gln Asn Cys
1

<210> SEQ ID NO 129
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 129

Cys Asn Gln Cys
1

<210> SEQ ID NO 130
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 130

Cys Gln Gln Cys
1

<210> SEQ ID NO 131
<211> LENGTH: 4
```

```
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 131

Cys Asn Asn Cys
1

<210> SEQ ID NO 132
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 132

Cys Gln Asn Gln Cys
1               5

<210> SEQ ID NO 133
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 133

Cys Asn Gln Asn Cys
1               5

<210> SEQ ID NO 134
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 134

Cys Gln Gln Gln Cys
1               5

<210> SEQ ID NO 135
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 135

Cys Asn Asn Asn Cys
1               5

<210> SEQ ID NO 136
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 136

Cys Gln Asn Gln Asn Cys
```

```
1               5
```

<210> SEQ ID NO 137
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 137

```
Cys Asn Gln Asn Gln Cys
1               5
```

<210> SEQ ID NO 138
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 138

```
Cys Gln Gln Gln Gln Cys
1               5
```

<210> SEQ ID NO 139
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 139

```
Cys Asn Asn Asn Asn Cys
1               5
```

<210> SEQ ID NO 140
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 140

```
Cys Asn Cys
1
```

<210> SEQ ID NO 141
<211> LENGTH: 3
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 141

```
Cys Ser Cys
1
```

<210> SEQ ID NO 142
<211> LENGTH: 4
<212> TYPE: PRT
<213> ORGANISM: Artificial Sequence
<220> FEATURE:
<223> OTHER INFORMATION: Exemplary hydrophilic (and preferably non charged polar) amino acid component (AA)

<400> SEQUENCE: 142

Cys Ser Asn Cys
1

<210> SEQ ID NO 143
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 143

Cys Asn Ser Cys
1

<210> SEQ ID NO 144
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 144

Cys Ser Ser Cys
1

<210> SEQ ID NO 145
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 145

Cys Asn Asn Cys
1

<210> SEQ ID NO 146
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 146

Cys Ser Asn Ser Cys
1               5

<210> SEQ ID NO 147
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 147

Cys Asn Ser Asn Cys
1               5

<210> SEQ ID NO 148

```
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 148

Cys Ser Ser Ser Cys
1               5

<210> SEQ ID NO 149
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 149

Cys Asn Asn Asn Cys
1               5

<210> SEQ ID NO 150
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 150

Cys Ser Asn Ser Asn Cys
1               5

<210> SEQ ID NO 151
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 151

Cys Asn Ser Asn Ser Cys
1               5

<210> SEQ ID NO 152
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 152

Cys Ser Ser Ser Ser Cys
1               5

<210> SEQ ID NO 153
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 153
```

-continued

Cys Asn Asn Asn Asn Cys
1               5

<210> SEQ ID NO 154
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 154

Leu Val
1

<210> SEQ ID NO 155
<211> LENGTH: 1
<212> TYPE: PRT
<213> ORGANISM: Artificial Sequence
<220> FEATURE:
<223> OTHER INFORMATION: Exemplary lipophilic amino acid component (AA)

<400> SEQUENCE: 155

Leu
1

<210> SEQ ID NO 156
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 156

Leu Leu
1

<210> SEQ ID NO 157

<400> SEQUENCE: 157

000

<210> SEQ ID NO 158
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 158

Leu Val Leu
1

<210> SEQ ID NO 159
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 159

Val Leu Val
1

<210> SEQ ID NO 160
<211> LENGTH: 3
<212> TYPE: PRT

```
<213> ORGANISM: Artificial Sequence
<220> FEATURE:
<223> OTHER INFORMATION: Exemplary lipophilic amino acid component (AA)

<400> SEQUENCE: 160

Leu Leu Leu
1

<210> SEQ ID NO 161
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 161

Val Val Val
1

<210> SEQ ID NO 162
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 162

Leu Val Leu Val
1

<210> SEQ ID NO 163
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 163

Val Leu Val Leu
1

<210> SEQ ID NO 164
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 164

Leu Leu Leu Leu
1

<210> SEQ ID NO 165
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 165

Val Val Val Val
1

<210> SEQ ID NO 166
<211> LENGTH: 2
<212> TYPE: PRT
<213> ORGANISM: Artificial Sequence
```

<220> FEATURE:
<223> OTHER INFORMATION: Exemplary lipophilic amino acid component (AA)

<400> SEQUENCE: 166

Ile Ala
1

<210> SEQ ID NO 167
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 167

Ala Ile
1

<210> SEQ ID NO 168
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 168

Ile Ile
1

<210> SEQ ID NO 169
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 169

Ala Ala
1

<210> SEQ ID NO 170
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 170

Ile Ala Ile
1

<210> SEQ ID NO 171
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 171

Ala Ile Ala
1

<210> SEQ ID NO 172
<211> LENGTH: 3
<212> TYPE: PRT
<213> ORGANISM: Artificial Sequence
<220> FEATURE:

-continued

<223> OTHER INFORMATION: Exemplary lipophilic amino acid component (AA)

<400> SEQUENCE: 172

Ile Ile Ile
1

<210> SEQ ID NO 173
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 173

Ala Ala Ala
1

<210> SEQ ID NO 174
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 174

Ile Ala Ile Ala
1

<210> SEQ ID NO 175
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 175

Ala Ile Ala Ile
1

<210> SEQ ID NO 176
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 176

Ile Ile Ile Ile
1

<210> SEQ ID NO 177
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 177

Ala Ala Ala Ala
1

<210> SEQ ID NO 178
<211> LENGTH: 2
<212> TYPE: PRT
<213> ORGANISM: Artificial Sequence
<220> FEATURE:
<223> OTHER INFORMATION: Exemplary lipophilic amino acid component (AA)

```
<400> SEQUENCE: 178

Met Ala
1

<210> SEQ ID NO 179
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 179

Ala Met
1

<210> SEQ ID NO 180
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 180

Met Met
1

<210> SEQ ID NO 181
<211> LENGTH: 2
<212> TYPE: PRT
<213> ORGANISM: Artificial Sequence
<220> FEATURE:
<223> OTHER INFORMATION: Exemplary lipophilic amino acid component (AA)

<400> SEQUENCE: 181

Ala Ala
1

<210> SEQ ID NO 182
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 182

Met Ala Met
1

<210> SEQ ID NO 183
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 183

Ala Met Ala
1

<210> SEQ ID NO 184
<211> LENGTH: 3
<212> TYPE: PRT
<213> ORGANISM: Artificial Sequence
<220> FEATURE:
<223> OTHER INFORMATION: Exemplary lipophilic amino acid component (AA)
```

```
<400> SEQUENCE: 184

Met Met Met
1

<210> SEQ ID NO 185
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 185

Ala Ala Ala
1

<210> SEQ ID NO 186
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 186

Met Ala Met Ala
1

<210> SEQ ID NO 187
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 187

Ala Met Ala Met
1

<210> SEQ ID NO 188
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 188

Met Met Met Met
1

<210> SEQ ID NO 189
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 189

Cys Val Cys
1

<210> SEQ ID NO 190
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 190
```

Cys Leu Cys
1

<210> SEQ ID NO 191
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 191

Cys Leu Val Cys
1

<210> SEQ ID NO 192
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 192

Cys Val Leu Cys
1

<210> SEQ ID NO 193
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 193

Cys Leu Leu Cys
1

<210> SEQ ID NO 194
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 194

Cys Val Val Cys
1

<210> SEQ ID NO 195
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 195

Cys Leu Val Leu Cys
1               5

<210> SEQ ID NO 196
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 196

-continued

Cys Val Leu Val Cys
1               5

<210> SEQ ID NO 197
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 197

Cys Leu Leu Leu Cys
1               5

<210> SEQ ID NO 198
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 198

Cys Val Val Val Cys
1               5

<210> SEQ ID NO 199
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 199

Cys Leu Val Leu Val Cys
1               5

<210> SEQ ID NO 200
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 200

Cys Val Leu Val Leu Cys
1               5

<210> SEQ ID NO 201
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 201

Cys Leu Leu Leu Leu Cys
1               5

<210> SEQ ID NO 202
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 202

Cys Val Val Val Val Cys

```
1               5
```

<210> SEQ ID NO 203
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 203

Cys Ala Cys
1

<210> SEQ ID NO 204
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 204

Cys Ile Cys
1

<210> SEQ ID NO 205
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 205

Cys Ile Ala Cys
1

<210> SEQ ID NO 206
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 206

Cys Ala Ile Cys
1

<210> SEQ ID NO 207
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 207

Cys Ile Ile Cys
1

<210> SEQ ID NO 208
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 208

Cys Ala Ala Cys
1

```
<210> SEQ ID NO 209
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 209

Cys Ile Ala Ile Cys
1               5

<210> SEQ ID NO 210
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 210

Cys Ala Ile Ala Cys
1               5

<210> SEQ ID NO 211
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 211

Cys Ile Ile Ile Cys
1               5

<210> SEQ ID NO 212
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 212

Cys Ala Ala Ala Cys
1               5

<210> SEQ ID NO 213
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 213

Cys Ile Ala Ile Ala Cys
1               5

<210> SEQ ID NO 214
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 214

Cys Ala Ile Ala Ile Cys
1               5
```

```
<210> SEQ ID NO 215
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 215

Cys Ile Ile Ile Ile Cys
1               5

<210> SEQ ID NO 216
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 216

Cys Ala Ala Ala Ala Cys
1               5

<210> SEQ ID NO 217
<211> LENGTH: 3
<212> TYPE: PRT
<213> ORGANISM: Artificial Sequence
<220> FEATURE:
<223> OTHER INFORMATION: Exemplary lipophilic amino acid component (AA)

<400> SEQUENCE: 217

Cys Met Cys
1

<210> SEQ ID NO 218
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 218

Cys Met Ala Cys
1

<210> SEQ ID NO 219
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 219

Cys Ala Met Cys
1

<210> SEQ ID NO 220
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 220

Cys Met Met Cys
1
```

```
<210> SEQ ID NO 221
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 221

Cys Ala Ala Cys
1

<210> SEQ ID NO 222
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 222

Cys Met Ala Met Cys
1               5

<210> SEQ ID NO 223
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 223

Cys Ala Met Ala Cys
1               5

<210> SEQ ID NO 224
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 224

Cys Met Met Met Cys
1               5

<210> SEQ ID NO 225
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 225

Cys Ala Ala Ala Cys
1               5

<210> SEQ ID NO 226
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 226

Cys Met Ala Met Ala Cys
1               5

<210> SEQ ID NO 227
```

```
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 227

Cys Ala Met Ala Met Cys
1               5

<210> SEQ ID NO 228
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 228

Cys Met Met Met Met Cys
1               5

<210> SEQ ID NO 229
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 229

Cys Ala Ala Ala Ala Cys
1               5

<210> SEQ ID NO 230
<211> LENGTH: 2
<212> TYPE: PRT
<213> ORGANISM: Artificial Sequence
<220> FEATURE:
<223> OTHER INFORMATION: Exemplary weak basic amino acid component (AA)

<400> SEQUENCE: 230

Asp His
1

<210> SEQ ID NO 231
<211> LENGTH: 2
<212> TYPE: PRT
<213> ORGANISM: Artificial Sequence
<220> FEATURE:
<223> OTHER INFORMATION: Exemplary weak basic amino acid component (AA)

<400> SEQUENCE: 231

His Asp
1

<210> SEQ ID NO 232
<211> LENGTH: 2
<212> TYPE: PRT
<213> ORGANISM: Artificial Sequence
<220> FEATURE:
<223> OTHER INFORMATION: Exemplary weak basic amino acid component (AA)

<400> SEQUENCE: 232

Asp Asp
1

<210> SEQ ID NO 233
<211> LENGTH: 2
```

```
<212> TYPE: PRT
<213> ORGANISM: Artificial Sequence
<220> FEATURE:
<223> OTHER INFORMATION: Exemplary weak basic amino acid component (AA)

<400> SEQUENCE: 233

His His
1

<210> SEQ ID NO 234
<211> LENGTH: 3
<212> TYPE: PRT
<213> ORGANISM: Artificial Sequence
<220> FEATURE:
<223> OTHER INFORMATION: Exemplary weak basic amino acid component (AA)

<400> SEQUENCE: 234

Asp His Asp
1

<210> SEQ ID NO 235
<211> LENGTH: 3
<212> TYPE: PRT
<213> ORGANISM: Artificial Sequence
<220> FEATURE:
<223> OTHER INFORMATION: Exemplary weak basic amino acid component (AA)

<400> SEQUENCE: 235

His Asp His
1

<210> SEQ ID NO 236
<211> LENGTH: 3
<212> TYPE: PRT
<213> ORGANISM: Artificial Sequence
<220> FEATURE:
<223> OTHER INFORMATION: Exemplary weak basic amino acid component (AA)

<400> SEQUENCE: 236

Asp Asp Asp
1

<210> SEQ ID NO 237
<211> LENGTH: 3
<212> TYPE: PRT
<213> ORGANISM: Artificial Sequence
<220> FEATURE:
<223> OTHER INFORMATION: Exemplary weak basic amino acid component (AA)

<400> SEQUENCE: 237

His His His
1

<210> SEQ ID NO 238
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 238

Asp His Asp His
1

<210> SEQ ID NO 239
<211> LENGTH: 4
<212> TYPE: PRT
```

```
<213> ORGANISM: Artificial Sequence
<220> FEATURE:
<223> OTHER INFORMATION: Exemplary weak basic amino acid component (AA)

<400> SEQUENCE: 239

His Asp His Asp
1

<210> SEQ ID NO 240
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 240

Asp Asp Asp Asp
1

<210> SEQ ID NO 241
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 241

His His His His
1

<210> SEQ ID NO 242
<211> LENGTH: 3
<212> TYPE: PRT
<213> ORGANISM: Artificial Sequence
<220> FEATURE:
<223> OTHER INFORMATION: Exemplary weak basic amino acid component (AA)

<400> SEQUENCE: 242

Cys His Cys
1

<210> SEQ ID NO 243
<211> LENGTH: 3
<212> TYPE: PRT
<213> ORGANISM: Artificial Sequence
<220> FEATURE:
<223> OTHER INFORMATION: Exemplary weak basic amino acid component (AA)

<400> SEQUENCE: 243

Cys Asp Cys
1

<210> SEQ ID NO 244
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 244

Cys Asp His Cys
1

<210> SEQ ID NO 245
<211> LENGTH: 4
<212> TYPE: PRT
<213> ORGANISM: Artificial Sequence
```

```
<220> FEATURE:
<223> OTHER INFORMATION: Exemplary weak basic amino acid component (AA)

<400> SEQUENCE: 245

Cys His Asp Cys
1

<210> SEQ ID NO 246
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 246

Cys Asp Asp Cys
1

<210> SEQ ID NO 247
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 247

Cys His His Cys
1

<210> SEQ ID NO 248
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 248

Cys Asp His Asp Cys
1               5

<210> SEQ ID NO 249
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 249

Cys His Asp His Cys
1               5

<210> SEQ ID NO 250
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 250

Cys Asp Asp Asp Cys
1               5

<210> SEQ ID NO 251
<211> LENGTH: 5
<212> TYPE: PRT
<213> ORGANISM: Artificial Sequence
<220> FEATURE:
```

```
<223> OTHER INFORMATION: Exemplary weak basic amino acid component (AA)

<400> SEQUENCE: 251

Cys His His His Cys
1               5

<210> SEQ ID NO 252
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 252

Cys Asp His Asp His Cys
1               5

<210> SEQ ID NO 253
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 253

Cys His Asp His Asp Cys
1               5

<210> SEQ ID NO 254
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 254

Cys Asp Asp Asp Asp Cys
1               5

<210> SEQ ID NO 255
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 255

Cys His His His His Cys
1               5

<210> SEQ ID NO 256
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 256

Lys Asp Glu Leu
1

<210> SEQ ID NO 257
<211> LENGTH: 4
<212> TYPE: PRT
<213> ORGANISM: Artificial Sequence
<220> FEATURE:
```

```
<223> OTHER INFORMATION: Description of sequence: signal peptide,
      localization signal or sequence or nuclear localization signal

<400> SEQUENCE: 257

Asp Asp Glu Leu
1

<210> SEQ ID NO 258
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 258

Asp Glu Glu Leu
1

<210> SEQ ID NO 259
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 259

Gln Glu Asp Leu
1

<210> SEQ ID NO 260
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 260

Arg Asp Glu Leu
1

<210> SEQ ID NO 261
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 261

Gly Gln Asn Leu Ser Thr Ser Asn
1               5

<210> SEQ ID NO 262
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 262

Pro Lys Lys Lys Arg Lys Val
1               5
```

```
<210> SEQ ID NO 263
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 263

Pro Gln Lys Lys Ile Lys Ser
1               5

<210> SEQ ID NO 264
<211> LENGTH: 5
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 264

Gln Pro Lys Lys Pro
1               5

<210> SEQ ID NO 265
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 265

Arg Lys Lys Arg
1

<210> SEQ ID NO 266
<211> LENGTH: 12
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 266

Arg Lys Lys Arg Arg Gln Arg Arg Arg Ala His Gln
1               5                   10

<210> SEQ ID NO 267
<211> LENGTH: 16
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 267

Arg Gln Ala Arg Arg Asn Arg Arg Arg Trp Arg Glu Arg Gln Arg
1               5                   10                  15

<210> SEQ ID NO 268
<211> LENGTH: 19
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 268
```

```
Met Pro Leu Thr Arg Arg Pro Ala Ala Ser Gln Ala Leu Ala Pro
1               5                   10                  15

Pro Thr Pro

<210> SEQ ID NO 269
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 269

Gly Ala Ala Leu Thr Ile Leu Val
1               5

<210> SEQ ID NO 270
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 270

Gly Ala Ala Leu Thr Leu Leu Gly
1               5

<210> SEQ ID NO 271
<211> LENGTH: 15
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 271

Met Asp Asp Gln Arg Asp Leu Ile Ser Asn Asn Glu Gln Leu Pro
1               5                   10                  15

<210> SEQ ID NO 272
<211> LENGTH: 32
<212> TYPE: PRT
<213> ORGANISM: Artificial Sequence
<220> FEATURE:
<223> OTHER INFORMATION: Description of sequence: signal peptide,
      localization signal or sequence or nuclear localization signal
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 272

Met Leu Phe Asn Leu Arg Xaa Xaa Leu Asn Asn Ala Ala Phe Arg His
1               5                   10                  15

Gly His Asn Phe Met Val Arg Asn Phe Arg Cys Gly Gln Pro Leu Xaa
                20                  25                  30

<210> SEQ ID NO 273
<211> LENGTH: 8
<212> TYPE: PRT
<213> ORGANISM: Artificial Sequence
<220> FEATURE:
```

<223> OTHER INFORMATION: Description of sequence: signal peptide,
      localization signal or sequence or nuclear localization signal

<400> SEQUENCE: 273

Gly Cys Val Cys Ser Ser Asn Pro
1               5

<210> SEQ ID NO 274
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 274

Gly Gln Thr Val Thr Thr Pro Leu
1               5

<210> SEQ ID NO 275
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 275

Gly Gln Glu Leu Ser Gln His Glu
1               5

<210> SEQ ID NO 276
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 276

Gly Asn Ser Pro Ser Tyr Asn Pro
1               5

<210> SEQ ID NO 277
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 277

Gly Val Ser Gly Ser Lys Gly Gln
1               5

<210> SEQ ID NO 278
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 278

Gly Gln Thr Ile Thr Thr Pro Leu
1               5

```
<210> SEQ ID NO 279
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 279

Gly Gln Thr Leu Thr Thr Pro Leu
1               5

<210> SEQ ID NO 280
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 280

Gly Gln Ile Phe Ser Arg Ser Ala
1               5

<210> SEQ ID NO 281
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 281

Gly Gln Ile His Gly Leu Ser Pro
1               5

<210> SEQ ID NO 282
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 282

Gly Ala Arg Ala Ser Val Leu Ser
1               5

<210> SEQ ID NO 283
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 283

Gly Cys Thr Leu Ser Ala Glu Glu
1               5

<210> SEQ ID NO 284
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 284
```

```
Gly Ala Gln Val Ser Ser Gln Lys
1               5

<210> SEQ ID NO 285
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 285

Gly Ala Gln Leu Ser Arg Asn Thr
1               5

<210> SEQ ID NO 286
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 286

Gly Asn Ala Ala Ala Ala Lys Lys
1               5

<210> SEQ ID NO 287
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 287

Gly Asn Glu Ala Ser Tyr Pro Leu
1               5

<210> SEQ ID NO 288
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 288

Gly Ser Ser Lys Ser Lys Pro Lys
1               5

<210> SEQ ID NO 289
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 289
gguuuuuuuu uuuuuuuggg                                              20

<210> SEQ ID NO 290
<211> LENGTH: 20
<212> TYPE: RNA
<213> ORGANISM: Artificial
<220> FEATURE:
<223> OTHER INFORMATION: nucleic acid sequence according to formula (II)
```

```
<400> SEQUENCE: 290 gggggu uuuu uuuuugggg                                         20

<210> SEQ ID NO 291
<211> LENGTH: 40
<212> TYPE: RNA
<213> ORGANISM: Artificial
<220> FEATURE:
<223> OTHER INFORMATION: nucleic acid sequence according to formula (II)

<400> SEQUENCE: 291 gggggu uuuu uuuuuuuuuu uuuuuuuuuu uuuuugggg                   40

<210> SEQ ID NO 292
<211> LENGTH: 39
<212> TYPE: RNA
<213> ORGANISM: Artificial
<220> FEATURE:
<223> OTHER INFORMATION: nucleic acid sequence according to formula (II)

<400> SEQUENCE: 292
gugugugugu guuuuuuuuu uuuuuuugug ugugugugu                    39

<210> SEQ ID NO 293
<211> LENGTH: 39
<212> TYPE: RNA
<213> ORGANISM: Artificial
<220> FEATURE:
<223> OTHER INFORMATION: nucleic acid sequence according to formula (II)

<400> SEQUENCE: 293
gguugguugg uuuuuuuuuu uuuuuuuggu ugguugguu                    39

<210> SEQ ID NO 294
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 294 ggggggggu uugggggggg                                          20

<210> SEQ ID NO 295
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 295
gggggggguu uugggggggg                                         20

<210> SEQ ID NO 296
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 296
gggggggguu uugggggggg                                         20

<210> SEQ ID NO 297
```

```
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 297 gggggggüuuu uuuugggggg                                              20

<210> SEQ ID NO 298
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 298
gggggguuuu uuuuggggggg                                              20

<210> SEQ ID NO 299
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 299
gggggguuuu uuuuugggggg                                              20

<210> SEQ ID NO 300
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 300
gggggguuuu uuuuuuggggg                                              20

<210> SEQ ID NO 301
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 301 gggggüuuuu uuuuuugggg                                               20

<210> SEQ ID NO 302
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 302 gggggüuuuu uuuuuuuggg                                               20

<210> SEQ ID NO 303
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 303
```

```
ggggguuuuuu uuuuuuuggg                                          20

<210> SEQ ID NO 304
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 304
gggguuuuuu uuuuuuuugg                                           20

<210> SEQ ID NO 305
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 305
gguuuuuuuu uuuuuuuugg                                           20

<210> SEQ ID NO 306
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 306
guuuuuuuuu uuuuuuuuug                                           20

<210> SEQ ID NO 307
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 307
gggggggggg uuugggggggg gg                                       22

<210> SEQ ID NO 308
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 308 ggggggggggu uuugggggggg gg                                      22

<210> SEQ ID NO 309
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 309 ggggggggguu uuugggggggg gg                                      22

<210> SEQ ID NO 310
<211> LENGTH: 22
<212> TYPE: RNA
```

```
<213> ORGANISM: Artificial
<220> FEATURE:
<223> OTHER INFORMATION: nucleic acid sequence according to formula (II)

<400> SEQUENCE: 310
gggggggguu uuuuugggg gg                                              22

<210> SEQ ID NO 311
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 311
gggggggguu uuuuggggg gg                                              22

<210> SEQ ID NO 312
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 312
ggggggguuu uuuuugggg gg                                              22

<210> SEQ ID NO 313
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 313
ggggggguuu uuuuuuggg gg                                              22

<210> SEQ ID NO 314
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 314
gggggguuuu uuuuuuggg gg                                              22

<210> SEQ ID NO 315
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 315
gggggguuuu uuuuuuugg gg                                              22

<210> SEQ ID NO 316
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 316
ggggguuuuu uuuuuuugg gg                                              22
```

```
<210> SEQ ID NO 317
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 317
ggggguuuuu uuuuuuuug gg                                              22

<210> SEQ ID NO 318
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 318
ggguuuuuuu uuuuuuuug gg                                              22

<210> SEQ ID NO 319
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 319
gguuuuuuuu uuuuuuuuu gg                                              22

<210> SEQ ID NO 320
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 320
gggggggggg guuuggggggg gggg                                          24

<210> SEQ ID NO 321
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 321
gggggggggg uuugggggg gggg                                            24

<210> SEQ ID NO 322
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 322 ggggggggggu uuuugggggg gggg                                          24

<210> SEQ ID NO 323
<211> LENGTH: 24
<212> TYPE: RNA
<213> ORGANISM: Artificial
<220> FEATURE:
```

-continued

<223> OTHER INFORMATION: nucleic acid sequence according to formula (II)

<400> SEQUENCE: 323
gggggggggu uuuuugggg gggg                                              24

<210> SEQ ID NO 324
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 324 ggggggggguu uuuuugggg gggg                                             24

<210> SEQ ID NO 325
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 325 ggggggggguu uuuuuuggg gggg                                             24

<210> SEQ ID NO 326
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 326 ggggggggguu uuuuuuugg gggg                                             24

<210> SEQ ID NO 327
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 327 gggggggguuu uuuuuuugg gggg                                             24

<210> SEQ ID NO 328
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 328 gggggggguuu uuuuuuuug gggg                                             24

<210> SEQ ID NO 329
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 329
gggggguuuu uuuuuuuug gggg                                              24

```
<210> SEQ ID NO 330
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 330
gggggguuuu uuuuuuuuu gggg                                          24

<210> SEQ ID NO 331
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 331
gggguuuuuu uuuuuuuuuu gggg                                         24

<210> SEQ ID NO 332
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 332
ggguuuuuuu uuuuuuuuuu uggg                                         24

<210> SEQ ID NO 333
<211> LENGTH: 32
<212> TYPE: RNA
<213> ORGANISM: Artificial
<220> FEATURE:
<223> OTHER INFORMATION: nucleic acid sequence according to formula (II)

<400> SEQUENCE: 333
guuuuuuuuu uuuuuuuuuu uuuuuuuuuu ug                                32

<210> SEQ ID NO 334
<211> LENGTH: 34
<212> TYPE: RNA
<213> ORGANISM: Artificial
<220> FEATURE:
<223> OTHER INFORMATION: nucleic acid sequence according to formula (II)

<400> SEQUENCE: 334
gguuuuuuuu uuuuuuuuuu uuuuuuuuuu uugg                              34

<210> SEQ ID NO 335
<211> LENGTH: 36
<212> TYPE: RNA
<213> ORGANISM: Artificial
<220> FEATURE:
<223> OTHER INFORMATION: nucleic acid sequence according to formula (II)

<400> SEQUENCE: 335
ggguuuuuuu uuuuuuuuuu uuuuuuuuuu uuuggg                            36

<210> SEQ ID NO 336
<211> LENGTH: 37
<212> TYPE: RNA
<213> ORGANISM: Artificial
<220> FEATURE:
<223> OTHER INFORMATION: nucleic acid sequence according to formula (II)
```

```
<400> SEQUENCE: 336
ggggutuuuu uuuuuuuuuu uuuuuuuuuu uuuuggg                                    37

<210> SEQ ID NO 337
<211> LENGTH: 39
<212> TYPE: RNA
<213> ORGANISM: Artificial
<220> FEATURE:
<223> OTHER INFORMATION: nucleic acid sequence according to formula (II)

<400> SEQUENCE: 337
gggggutuuu uuuuuuuuuu uuuuuuuuuu uuuugggg                                   39

<210> SEQ ID NO 338
<211> LENGTH: 41
<212> TYPE: RNA
<213> ORGANISM: Artificial
<220> FEATURE:
<223> OTHER INFORMATION: nucleic acid sequence according to formula (II)

<400> SEQUENCE: 338
ggggggutuu uuuuuuuuuu uuuuuuuuuu uuuuuggggg g                               41

<210> SEQ ID NO 339
<211> LENGTH: 43
<212> TYPE: RNA
<213> ORGANISM: Artificial
<220> FEATURE:
<223> OTHER INFORMATION: nucleic acid sequence according to formula (II)

<400> SEQUENCE: 339
gggggggutu uuuuuuuuuu uuuuuuuuuu uuuuuuggg ggg                              43

<210> SEQ ID NO 340
<211> LENGTH: 45
<212> TYPE: RNA
<213> ORGANISM: Artificial
<220> FEATURE:
<223> OTHER INFORMATION: nucleic acid sequence according to formula (II)

<400> SEQUENCE: 340
ggggggggut uuuuuuuuuu uuuuuuuuuu uuuuuuugg ggggg                            45

<210> SEQ ID NO 341
<211> LENGTH: 47
<212> TYPE: RNA
<213> ORGANISM: Artificial
<220> FEATURE:
<223> OTHER INFORMATION: nucleic acid sequence according to formula (II)

<400> SEQUENCE: 341 ggggggggu uuuuuuuuu uuuuuuuuu uuuuuuuug gggggggg                            47

<210> SEQ ID NO 342
<211> LENGTH: 7
<212> TYPE: RNA
<213> ORGANISM: Artificial
<220> FEATURE:
<223> OTHER INFORMATION: nucleic acid sequence according to formula (II)

<400> SEQUENCE: 342 gguuugg                                                                      7

<210> SEQ ID NO 343
<211> LENGTH: 8
```

```
<212> TYPE: RNA
<213> ORGANISM: Artificial
<220> FEATURE:
<223> OTHER INFORMATION: nucleic acid sequence according to formula (II)

<400> SEQUENCE: 343 gguuuugg                                                              8

<210> SEQ ID NO 344
<211> LENGTH: 9
<212> TYPE: RNA
<213> ORGANISM: Artificial
<220> FEATURE:
<223> OTHER INFORMATION: nucleic acid sequence according to formula (II)

<400> SEQUENCE: 344 gguuuuugg                                                             9

<210> SEQ ID NO 345
<211> LENGTH: 10
<212> TYPE: RNA
<213> ORGANISM: Artificial
<220> FEATURE:
<223> OTHER INFORMATION: nucleic acid sequence according to formula (II)

<400> SEQUENCE: 345
gguuuuuugg                                                           10

<210> SEQ ID NO 346
<211> LENGTH: 11
<212> TYPE: RNA
<213> ORGANISM: Artificial
<220> FEATURE:
<223> OTHER INFORMATION: nucleic acid sequence according to formula (II)

<400> SEQUENCE: 346
gguuuuuuug g                                                         11

<210> SEQ ID NO 347
<211> LENGTH: 12
<212> TYPE: RNA
<213> ORGANISM: Artificial
<220> FEATURE:
<223> OTHER INFORMATION: nucleic acid sequence according to formula (II)

<400> SEQUENCE: 347
gguuuuuuuu gg                                                        12

<210> SEQ ID NO 348
<211> LENGTH: 13
<212> TYPE: RNA
<213> ORGANISM: Artificial
<220> FEATURE:
<223> OTHER INFORMATION: nucleic acid sequence according to formula (II)

<400> SEQUENCE: 348
gguuuuuuuu ugg                                                       13

<210> SEQ ID NO 349
<211> LENGTH: 14
<212> TYPE: RNA
<213> ORGANISM: Artificial
<220> FEATURE:
<223> OTHER INFORMATION: nucleic acid sequence according to formula (II)

<400> SEQUENCE: 349
```

```
gguuuuuuuu uugg                                                          14

<210> SEQ ID NO 350
<211> LENGTH: 15
<212> TYPE: RNA
<213> ORGANISM: Artificial
<220> FEATURE:
<223> OTHER INFORMATION: nucleic acid sequence according to formula (II)

<400> SEQUENCE: 350
gguuuuuuuu uuugg                                                         15

<210> SEQ ID NO 351
<211> LENGTH: 16
<212> TYPE: RNA
<213> ORGANISM: Artificial
<220> FEATURE:
<223> OTHER INFORMATION: nucleic acid sequence according to formula (II)

<400> SEQUENCE: 351
gguuuuuuuu uuuugg                                                        16

<210> SEQ ID NO 352
<211> LENGTH: 17
<212> TYPE: RNA
<213> ORGANISM: Artificial
<220> FEATURE:
<223> OTHER INFORMATION: nucleic acid sequence according to formula (II)

<400> SEQUENCE: 352
gguuuuuuuu uuuuugg                                                       17

<210> SEQ ID NO 353
<211> LENGTH: 18
<212> TYPE: RNA
<213> ORGANISM: Artificial
<220> FEATURE:
<223> OTHER INFORMATION: nucleic acid sequence according to formula (II)

<400> SEQUENCE: 353
gguuuuuuuu uuuuuugg                                                      18

<210> SEQ ID NO 354
<211> LENGTH: 19
<212> TYPE: RNA
<213> ORGANISM: Artificial
<220> FEATURE:
<223> OTHER INFORMATION: nucleic acid sequence according to formula (II)

<400> SEQUENCE: 354
gguuuuuuuu uuuuuuugg                                                     19

<210> SEQ ID NO 355
<211> LENGTH: 9
<212> TYPE: RNA
<213> ORGANISM: Artificial
<220> FEATURE:
<223> OTHER INFORMATION: nucleic acid sequence according to formula (II)

<400> SEQUENCE: 355 ggguuuggg                                                                 9

<210> SEQ ID NO 356
<211> LENGTH: 10
<212> TYPE: RNA
<213> ORGANISM: Artificial
```

-continued

```
<220> FEATURE:
<223> OTHER INFORMATION: nucleic acid sequence according to formula (II)

<400> SEQUENCE: 356
ggguuuuggg                                                                10

<210> SEQ ID NO 357
<211> LENGTH: 11
<212> TYPE: RNA
<213> ORGANISM: Artificial
<220> FEATURE:
<223> OTHER INFORMATION: nucleic acid sequence according to formula (II)

<400> SEQUENCE: 357
ggguuuuugg g                                                              11

<210> SEQ ID NO 358
<211> LENGTH: 12
<212> TYPE: RNA
<213> ORGANISM: Artificial
<220> FEATURE:
<223> OTHER INFORMATION: nucleic acid sequence according to formula (II)

<400> SEQUENCE: 358
ggguuuuuug gg                                                             12

<210> SEQ ID NO 359
<211> LENGTH: 13
<212> TYPE: RNA
<213> ORGANISM: Artificial
<220> FEATURE:
<223> OTHER INFORMATION: nucleic acid sequence according to formula (II)

<400> SEQUENCE: 359
ggguuuuuuu ggg                                                            13

<210> SEQ ID NO 360
<211> LENGTH: 14
<212> TYPE: RNA
<213> ORGANISM: Artificial
<220> FEATURE:
<223> OTHER INFORMATION: nucleic acid sequence according to formula (II)

<400> SEQUENCE: 360
ggguuuuuuu uggg                                                           14

<210> SEQ ID NO 361
<211> LENGTH: 15
<212> TYPE: RNA
<213> ORGANISM: Artificial
<220> FEATURE:
<223> OTHER INFORMATION: nucleic acid sequence according to formula (II)

<400> SEQUENCE: 361
ggguuuuuuu uuggg                                                          15

<210> SEQ ID NO 362
<211> LENGTH: 16
<212> TYPE: RNA
<213> ORGANISM: Artificial
<220> FEATURE:
<223> OTHER INFORMATION: nucleic acid sequence according to formula (II)

<400> SEQUENCE: 362
ggguuuuuuu uuuggg                                                         16
```

```
<210> SEQ ID NO 363
<211> LENGTH: 17
<212> TYPE: RNA
<213> ORGANISM: Artificial
<220> FEATURE:
<223> OTHER INFORMATION: nucleic acid sequence according to formula (II)

<400> SEQUENCE: 363
ggguuuuuuu uuuuggg                                                    17

<210> SEQ ID NO 364
<211> LENGTH: 18
<212> TYPE: RNA
<213> ORGANISM: Artificial
<220> FEATURE:
<223> OTHER INFORMATION: nucleic acid sequence according to formula (II)

<400> SEQUENCE: 364
ggguuuuuuu uuuuuggg                                                   18

<210> SEQ ID NO 365
<211> LENGTH: 19
<212> TYPE: RNA
<213> ORGANISM: Artificial
<220> FEATURE:
<223> OTHER INFORMATION: nucleic acid sequence according to formula (II)

<400> SEQUENCE: 365
ggguuuuuuu uuuuuuggg                                                  19

<210> SEQ ID NO 366
<211> LENGTH: 57
<212> TYPE: RNA
<213> ORGANISM: Artificial
<220> FEATURE:
<223> OTHER INFORMATION: nucleic acid sequence according to formula (II)

<400> SEQUENCE: 366
ggguuuuuuu uuuuuuuugg guuuuuuuuu uuuuugggu uuuuuuuuu uuuggg           57

<210> SEQ ID NO 367
<211> LENGTH: 42
<212> TYPE: RNA
<213> ORGANISM: Artificial
<220> FEATURE:
<223> OTHER INFORMATION: nucleic acid sequence according to formula (II)

<400> SEQUENCE: 367
ggguuuuuuu uuuuuuuugg ggggguuuuu uuuuuuuuug gg                        42

<210> SEQ ID NO 368
<211> LENGTH: 51
<212> TYPE: RNA
<213> ORGANISM: Artificial
<220> FEATURE:
<223> OTHER INFORMATION: nucleic acid sequence according to formula
      (III)

<400> SEQUENCE: 368 ggguuuggggu uugggguuugg guuugggguu gggguugggu uugggguugg g            51

<210> SEQ ID NO 369
<211> LENGTH: 20
<212> TYPE: RNA
<213> ORGANISM: Artificial Sequence
<220> FEATURE:
```

```
<223> OTHER INFORMATION: nucleic acid sequence according to formula
      (II) - Short GU rich

<400> SEQUENCE: 369
gguuuuuuuu uuuuuuuggg                                              20

<210> SEQ ID NO 370
<211> LENGTH: 57
<212> TYPE: RNA
<213> ORGANISM: Artificial
<220> FEATURE:
<223> OTHER INFORMATION: nucleic acid sequence according to formula
      (III)

<400> SEQUENCE: 370 cccuuuuuu uuuuuuuucc cuuuuuuuuu uuuuuccccu uuuuuuuuuu uuuccc       57

<210> SEQ ID NO 371
<211> LENGTH: 51
<212> TYPE: RNA
<213> ORGANISM: Artificial
<220> FEATURE:
<223> OTHER INFORMATION: nucleic acid sequence according to formula
      (III)

<400> SEQUENCE: 371
cccuuucccu uucccuuucc cuuucccuuu cccuuucccu uucccuuucc c           51

<210> SEQ ID NO 372
<211> LENGTH: 42
<212> TYPE: RNA
<213> ORGANISM: Artificial
<220> FEATURE:
<223> OTHER INFORMATION: nucleic acid sequence according to formula
      (III)

<400> SEQUENCE: 372
cccuuuuuuu uuuuuuuucc ccccuuuuuu uuuuuuuuc cc                      42

<210> SEQ ID NO 373
<211> LENGTH: 60
<212> TYPE: RNA
<213> ORGANISM: Artificial Sequence
<220> FEATURE:
<223> OTHER INFORMATION: nucleic acid sequence according to formula (IV)

<400> SEQUENCE: 373
uagcgaagcu cuuggaccua gguuuuuuuu uuuuuuuggg ugcguuccua gaaguacacg  60

<210> SEQ ID NO 374
<211> LENGTH: 120
<212> TYPE: RNA
<213> ORGANISM: Artificial Sequence
<220> FEATURE:
<223> OTHER INFORMATION: nucleic acid sequence according to formula (IV)

<400> SEQUENCE: 374
uagcgaagcu cuuggaccua gguuuuuuuu uuuuuuuggg ugcguuccua gaaguacacg  60
aucgcuucga gaaccuggau ccaaaaaaaa aaaaaaccc acgcaaggau cuucaugugc  120

<210> SEQ ID NO 375
<211> LENGTH: 229
<212> TYPE: RNA
<213> ORGANISM: Artificial Sequence
<220> FEATURE:
<223> OTHER INFORMATION: nucleic acid sequence according to formula (IV)
```

<400> SEQUENCE: 375

```
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagauc               229
```

<210> SEQ ID NO 376
<211> LENGTH: 547
<212> TYPE: RNA
<213> ORGANISM: Artificial Sequence
<220> FEATURE:
<223> OTHER INFORMATION: nucleic acid sequence according to formula (IV)

<400> SEQUENCE: 376

```
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240
cuggaaggag caggaguagu guucuugcuc uaaguaccga gugugcccaa uacccgauca   300
gcuuauuaac gaacggcucc uccucuuaga cugcagcgua agugcggaau cggggauca   360
aauuacugac ugccuggauu acccucggac auauaaccuu guagcacgcu guugcuguau   420
aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuag                                                             547
```

<210> SEQ ID NO 377
<211> LENGTH: 1083
<212> TYPE: RNA
<213> ORGANISM: Artificial Sequence
<220> FEATURE:
<223> OTHER INFORMATION: nucleic acid sequence according to formula (IV)

<400> SEQUENCE: 377

```
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240
cuggaaggag caggaguagu guucuugcuc uaaguaccga gugugcccaa uacccgauca   300
gcuuauuaac gaacggcucc uccucuuaga cugcagcgua agugcggaau cggggauca   360
aauuacugac ugccuggauu acccucggac auauaaccuu guagcacgcu guugcuguau   420
aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuagagc uacgcagguu cgcaauaaaa gcguugauua gugugcauag aacagaccuc   600
uuauucggug aaacgccaga augcuaaauu ccaauaacuc uucccaaaac gcguacggcc   660
gaagacgcgc gcuuaucuug uguacguucu cgcacaugga agaaucagcg ggcaugguug   720
uagggcaaua ggggagcugg guagcagcga aaaagggccc cugcgcacgu agcuucgcug   780
uucgucugaa acaacccggc auccguugua gcgauccgu uacagugguu auucuugugc   840
```

| | |
|---|---|
| gcacuaagau ucauggugua gucgacaaua acagcgucuu ggcagauucu ggucacgugc | 900 |
| ccuaugcccg ggcuugugcc ucucaggugc acagcgauac uuaaagccuu caagguacuc | 960 |
| gacgugggua ccgauucgug acacuuccua agauuauucc acuguuuag ccccgcaccg | 1020 |
| ccgaccuaaa cugguccaau guauacgcau ucgcugagcg gaucgauaau aaaagcuuga | 1080 |
| auu | 1083 |

<210> SEQ ID NO 378
<211> LENGTH: 229
<212> TYPE: RNA
<213> ORGANISM: Artificial Sequence
<220> FEATURE:
<223> OTHER INFORMATION: nucleic acid sequence according to formula (IV)

<400> SEQUENCE: 378

| | |
|---|---|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuu | 180 |
| uuuuuaguaa augcgucuac ugaauccagc gaugaugcug gcccagauc | 229 |

<210> SEQ ID NO 379
<211> LENGTH: 546
<212> TYPE: RNA
<213> ORGANISM: Artificial Sequence
<220> FEATURE:
<223> OTHER INFORMATION: nucleic acid sequence according to formula (IV)

<400> SEQUENCE: 379

| | |
|---|---|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuu | 180 |
| uuuuuaguaa augcgucuac ugaauccagc gaugaugcug gcccagaucu ucgaccacaa | 240 |
| gugcauauag uagucaucga ggucgcccuu uuuuuuuuu uuuuuuuuuu uggcccaguu | 300 |
| cugagacuuc gcuagagacu acaguuacag cugcaguagu aaccacugcg gcuauugcag | 360 |
| gaaauccggu ucagguuuuu uuuuuuuuu uuuuuccgc ucacuaugau uaagaaccag | 420 |
| guggagraguc acugcucucg aggucucacg agagcgcucg auacaguccu uggaagaauc | 480 |
| uuuuuuuuuu uuuuuuuuuu uugugcgacg aucacagaga acuucuauuc augcaggucu | 540 |
| gcucua | 546 |

<210> SEQ ID NO 380
<211> LENGTH: 1083
<212> TYPE: RNA
<213> ORGANISM: Artificial Sequence
<220> FEATURE:
<223> OTHER INFORMATION: nucleic acid sequence according to formula (IV)

<400> SEQUENCE: 380

| | |
|---|---|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuu | 180 |
| uuuuuaguaa augcgucuac ugaauccagc gaugaugcug gcccagaucu ucgaccacaa | 240 |
| gugcauauag uagucaucga ggucgcccuu uuuuuuuuu uuuuuuuuuu uggcccaguu | 300 |
| cugagacuuc gcuagagacu acaguuacag cugcaguagu aaccacugcg gcuauugcag | 360 |

-continued

```
gaaaucccgu ucagguuuuu uuuuuuuuuu uuuuuuccgc ucacuaugau uaagaaccag        420
guggaguguc acugcucucg aggucucacg agagcgcucg auacaguccu uggaagaauc        480
uuuuuuuuuu uuuuuuuuuu uugugcgacg aucacagaga acuucuauuc augcaggucu        540
gcucuagaac gaacugaccu gacgccugaa cuuaugagcg ugcguauuuu uuuuuuuuu        600 uuuuuuuuuc ucccaacaa augucgauca auagcugggc uguuggagac gcucagcaa        660 augccguggc uccauaggac guguagacuu cuauuuuuuu uuuuuuuuuu uuucccggg        720 accacaaaua auauucuugc uugguuggc gcaagggccc cguaucaggu cauaaacggg        780
uacauguugc acaggcuccu uuuuuuuuuu uuuuuuuuuu uucgcugagu uauuccgguc        840
ucaaaagacg gcagacguca gucgacaaca cggucuaaag cagugcuaca aucugccgug        900
uucguguuuu uuuuuuuuuu uuuuuuguga accacacgg cgugcacugu aguucgcaau        960
ucauagggua ccggcucaga guuaugccuu gguugaaaac ugcccagcau acuuuuuuuu       1020
uuuuuuuuuu uucauauucc caugcuaagc aagggaugcc gcgagucaug uuaagcuga       1080 auu                                                                    1083
```

<210> SEQ ID NO 381
<211> LENGTH: 59
<212> TYPE: RNA
<213> ORGANISM: Artificial Sequence
<220> FEATURE:
<223> OTHER INFORMATION: nucleic acid sequence according to formula (V)

<400> SEQUENCE: 381

```
uagcgaagcu cuuggaccua ccuuuuuuuu uuuuuucccu gcguuccuag aaguacacg         59
```

<210> SEQ ID NO 382
<211> LENGTH: 120
<212> TYPE: RNA
<213> ORGANISM: Artificial Sequence
<220> FEATURE:
<223> OTHER INFORMATION: nucleic acid sequence according to formula (V)

<400> SEQUENCE: 382

```
uagcgaagcu cuuggaccua ccuuuuuuuu uuuuuuccc ugcguuccua gaaguacacg         60
aucgcuucga gaaccuggau ggaaaaaaaa aaaaaaggg acgcaaggau cuucaugugc        120
```

<210> SEQ ID NO 383
<211> LENGTH: 15
<212> TYPE: RNA
<213> ORGANISM: Artificial
<220> FEATURE:
<223> OTHER INFORMATION: Description of sequence: generic stabilizing
      sequence of the formula (C/U)CCANxCCC(U/A)PyxUC(C/U)CC
<220> FEATURE:
<221> NAME/KEY: variation
<222> LOCATION: (1)..(1)
<223> OTHER INFORMATION: /replace="cytosine" /replace="uracile"
<220> FEATURE:
<221> NAME/KEY: misc_feature
<222> LOCATION: (1)..(1)
<223> OTHER INFORMATION: nucleic acid = cytosine or uracil
<220> FEATURE:
<221> NAME/KEY: misc_feature
<222> LOCATION: (5)..(5)
<223> OTHER INFORMATION: Nx = a, g, c or u or any other nucleic acid
<220> FEATURE:
<221> NAME/KEY: variation
<222> LOCATION: (5)..(5)
<223> OTHER INFORMATION: /replace="cytosine" /replace="uracile"
      /replace="guanosine" /replace="adenosine", or any other nucleic
      acid

```
<220> FEATURE:
<221> NAME/KEY: repeat_unit
<222> LOCATION: (5)..(5)
<223> OTHER INFORMATION: x = any number
<220> FEATURE:
<221> NAME/KEY: misc_feature
<222> LOCATION: (9)..(9)
<223> OTHER INFORMATION: nucleic acid = uracil or adenosine
<220> FEATURE:
<221> NAME/KEY: variation
<222> LOCATION: (9)..(9)
<223> OTHER INFORMATION: /replace="uracile" /replace="adonosine"
<220> FEATURE:
<221> NAME/KEY: misc_feature
<222> LOCATION: (10)..(10)
<223> OTHER INFORMATION: Py = pyrimidine
<220> FEATURE:
<221> NAME/KEY: repeat_unit
<222> LOCATION: (10)..(10)
<223> OTHER INFORMATION: x = any number
<220> FEATURE:
<221> NAME/KEY: variation
<222> LOCATION: (10)..(10)
<223> OTHER INFORMATION: /replace="pyrimidine"
<220> FEATURE:
<221> NAME/KEY: misc_feature
<222> LOCATION: (13)..(13)
<223> OTHER INFORMATION: nucleic acid = cytosine or uracil
<220> FEATURE:
<221> NAME/KEY: variation
<222> LOCATION: (13)..(13)
<223> OTHER INFORMATION: /replace="cytosine" /replace="uracile"

<400> SEQUENCE: 383 nccanccnn ucncc                                                       15

<210> SEQ ID NO 384
<211> LENGTH: 1845
<212> TYPE: DNA
<213> ORGANISM: Artificial Sequence
<220> FEATURE:
<223> OTHER INFORMATION: R1180 - exemplary nucleic acid cargo

<400> SEQUENCE: 384
gggagaaagc uugaggaugg aggacgccaa gaacaucaag aagggcccgg cgcccuucua       60
cccgcuggag gacgggaccg ccggcgagca gcuccacaag gccaugaagc gguacgcccu      120
ggugccgggc acgaucgccu ucaccgacgc ccacaucgag gucgacauca ccuacgcgga      180
guacuucgag augagcgugc gccuggccga ggccaugaag cgguacggcc ugaacaccaa      240
ccaccggauc gugguguccu cggagaacag ccugcaguuc uucaugccgg ugcugggcgc      300
ccucuucauc ggcguggccg ucgccccggc gaacgacauc uacaacgagc gggagcugcu      360
gaacagcaug gggaucagcc agccgaccgu ggguucgug agcaagaagg ccugcagaa       420 gauccugaac gugcagaaga agcugcccau cauccagaag aucaucauca uggacagcaa      480
gaccgacuac cagggcuucc agucgaugua cacguucgug accagccacc ucccgccggg      540
cuucaacgag uacgacuucg ucccggagag cuucgaccgg acaagacca ucgcccugau      600 caugaacagc agcggcagca ccggccugcc gaaggggug gccugccgc accggaccgc       660 cugcgugcgc uucucgcacg cccgggaccc caucuucggc aaccagauca ucccggacac      720
cgccauccug agcguggugc cguuccacca cggcuucggc auguucacga cccgggcua       780 ccucaucugc ggcuuccggg ugguccugau guaccgguuc gaggaggagc uguuccugcg      840
gagccugcag gacuacaaga uccagagcgc gcucucgug ccgacccugu ucagcuucuu      900
cgccaagagc acccugaucg acaaguacga ccugucgaac cugcacgaga ucgccagcgg      960
```

-continued

```
gggcgccccg cugagcaagg aggugggcga ggccguggcc aagcgguucc accucccggg   1020
cauccgccag ggcuacggcc ugaccgagac cacgagcgcg auccugauca ccccccgaggg  1080 ggacgacaag ccgggcgccg ugggcaaggu gguccccguuc uucgaggcca aggugguuga  1140
ccuggacacc ggcaagaccc uggggcgugaa ccagcggggc gagcugugcg ugcggggggcc  1200 gaugaucaug agcggcuacg ugaacaaccc ggaggccacc aacgcccuca ucgacaagga  1260
cggcuggcug cacagcggcg acaucgccua cugggacgag gacgagcacu cuuucaucgu  1320
cgaccggcug aagucgcuga ucaaguacaa gggcuaccag guggcgccgg ccgagcugga  1380
gagcauccug cuccagcacc ccaacaucuu cgacgccggc guggccgggc ugccggacga  1440
cgacgccggc gagcugccgg ccgcgguggu ggugcuggag cacggcaaga ccaugacgga  1500
gaaggagauc gucgacuacg uggccagcca ggugaccacc gccaagaagc ugcggggcgg  1560 cguggguguuc guggacgagg ucccgaaggg ccugaccggg aagcucgacg cccggaagau  1620
ccgcgagauc cugaucaagg ccaagaaggg cggcaagauc gccguguaag acuaguuaua  1680
agacugacua gcccgauggg ccucccaacg ggccccuccuc cccuccuugc accgagauua  1740
auaaaaaaaa aaaaaaaaaa aaaaaaaaaa aaaaaaaaaa aaaaaaaaaa aaaaaaaaaa  1800
aaaaaauauu ccccccccccc ccccccccccc cccccccccc ucuag                1845
```

<210> SEQ ID NO 385
<211> LENGTH: 547
<212> TYPE: DNA
<213> ORGANISM: Artificial Sequence
<220> FEATURE:
<223> OTHER INFORMATION: R722 - exemplary nucleic acid cargo

<400> SEQUENCE: 385

```
gggagaaagc ucaagcuuau ccaaguaggc uggucaccug uacaacguag ccgguauuuu    60
uuuuuuuuuu uuuuuuuga ccgucucaag guccaaguua gucugccuau aaaggugcgg   120
auccacagcu gaugaaagac uugugcgua cgguuaaucu ccccuuuuuu uuuuuuuuu   180 uuuuuaguaa augcgucuac ugaauccagc gaugaugcug gcccagaucu ucgaccacaa   240
gugcauauag uagucaucga gggucgccuu uuuuuuuuuu uuuuuuuuuu uggcccaguu   300
cugagacuuc gcuagagacu acaguuacag cugcaguagu aaccacgcg gcuauugcag    360 gaaaucccgu ucagguuuuu uuuuuuuuuu uuuuuccgc ucacuaugau uaagaaccag    420
guggaguguc acugcucucg aggucucacg agagcgcucg auacaguccu uggaagaauc    480
uuuuuuuuuu uuuuuuuuuu uugugcgacg aucacagaga acuucuauuc augcaggucu    540
gcucuag                                                             547
```

<210> SEQ ID NO 386
<211> LENGTH: 1857
<212> TYPE: DNA
<213> ORGANISM: Artificial Sequence
<220> FEATURE:
<223> OTHER INFORMATION: R491 - exemplary nucleic acid cargo

<400> SEQUENCE: 386

```
gggagaaagc uugaggaugg aggacgccaa gaacaucaag aagggcccgg cgcccuucua    60
cccgcuggag gacgggaccg ccggcgagca gcuccacaag gccaugaagc gguacgcccu   120
ggugccgggc acgaucgccu ucaccgacgc ccacaucgag gucgacauca ccuacgcgga   180
guacuucgag augagcgugc gccuggcgga ggccaugaag cgguacggcc ugaacaccaa   240
ccaccggauc guggugugcu cggagaacag ccugcaguuc uucaugccgg ugcugggcgc   300
```

```
ccucuucauc ggcguggccg ucgccccggc gaacgacauc uacaacgagc gggagcugcu      360
gaacagcaug gggaucagcc agccgaccgu ggucuucgug agcaagaagg gccugcagaa      420
gauccugaac gugcagaaga agcugcccau cauccagaag aucaucauca uggacagcaa      480
gaccgacuac cagggcuucc agucgaugua cacguucgug accagccacc ucccgccggg      540
cuucaacgag uacgacuucg ucccggagag cuucgaccgg gacaagacca ucgcccugau      600
caugaacagc agcggcagca ccggccugcc gaaggggggug gcccugccgc accgaccgc      660 cugcgugcgc uucucgcacg cccgggaccc caucuucggc aaccagauca ucccggacac      720
cgccauccug agcguggugc cguuccacca cggcuucggc auguuacga cccugggcua      780 ccucaucugc ggcuuccggg ugguccugau guaccgguuc gaggaggagc uguuccugcg      840
gagccugcag gacuacaaga uccagagcgc gcugcucgug ccgacccugu ucagcuucuu      900
cgccaagagc acccugaucg acaaguacga ccugucgaac cugcacgaga ucgccagcgg      960
gggcgccccg cugagcaagg agugggcga ggccguggcc aagcgguucc accucccggg      1020
cauccgccag ggcuacggcc ugaccgagac cacgagcgcg auccugauca cccccgaggg      1080
ggacgacaag ccgggcgccg ugggcaaggu gguccguuc uucgaggcca aggugguga      1140 ccuggacacc ggcaagaccc ugggcgugaa ccagcggggc gagcugugcg ugcggggggc      1200
gaugaucaug agcggcuacg ugaacaaccc ggaggccacc aacgcccuca ucgacaagga      1260
cggcuggcug cacagcggcg acaucgccua cugggacgag gacgagcacu ucuucaucgu      1320
cgaccggcug aagucgcuga ucaaguacaa gggcuaccag guggcgccgg ccgagcugga      1380
gagcauccug cuccagcacc ccaacaucuu cgacgccggc guggccgggc ugccggacga      1440
cgacgccggc gagcugccgg ccgcggugu ggugcuggag cacggcaaga ccaugacgga      1500
gaaggagauc gucgacuacg uggccagcca ggugaccacc gccaagaagc ugcggggcgg      1560
cguggucuuc guggacgagg ucccgaaggg ccugaccggg aagcucgacg cccggaagau      1620
ccgcgagauc cugaucaagg ccaagaaggg cggcaagauc gccguguaag acuaguuaua      1680
agacugacua gcccgauggg ccucccaacg ggcccuccuc ccucccuugc accgagauua      1740
auaaaaaaaa aaaaaaaaaa aaaaaaaaaa aaaaaaaaaa aaaaaaaaaa aaaaaaaaaa      1800
aaaaaauauu cccccccccc cccccccccc cccccccccc ucuagacaau uggaauu        1857

<210> SEQ ID NO 387
<211> LENGTH: 20
<212> TYPE: DNA
<213> ORGANISM: Artificial Sequence
<220> FEATURE:
<223> OTHER INFORMATION: CpG 2216 - exemplary nucleic acid cargo

<400> SEQUENCE: 387
gggggacgat cgtcgggggg                                                  20

<210> SEQ ID NO 388
<211> LENGTH: 18
<212> TYPE: PRT
<213> ORGANISM: Artificial sequence
<220> FEATURE:
<223> OTHER INFORMATION: Synthetic peptide

<400> SEQUENCE: 388

Cys His His His His His His Arg Arg Arg Arg His His His His His
1               5                   10                  15

His Cys
```

```
<210> SEQ ID NO 389
<211> LENGTH: 11
<212> TYPE: PRT
<213> ORGANISM: Artificial sequence
<220> FEATURE:
<223> OTHER INFORMATION: Synthetic peptide

<400> SEQUENCE: 389

Cys His Lys Lys Lys Lys Lys Lys Lys His Cys
1               5                   10

<210> SEQ ID NO 390
<211> LENGTH: 12
<212> TYPE: PRT
<213> ORGANISM: Artificial sequence
<220> FEATURE:
<223> OTHER INFORMATION: Synthetic peptide

<400> SEQUENCE: 390

Cys His His His Arg Arg Arg Arg His His His Cys
1               5                   10
```